US011103730B2

(12) United States Patent
Zwart et al.

(10) Patent No.: US 11,103,730 B2
(45) Date of Patent: Aug. 31, 2021

(54) AUTOMATED TREATMENT IN PARTICLE THERAPY

(71) Applicant: Mevion Medical Systems, Inc., Littleton, MA (US)

(72) Inventors: Gerrit Townsend Zwart, Durham, NH (US); Mark R. Jones, Reading, MA (US); James Cooley, Andover, MA (US); Stanley J. Rosenthal, Wayland, MA (US)

(73) Assignee: MEVION MEDICAL SYSTEMS, INC., Littleton, MA (US)

( * ) Notice: Subject to any disclaimer, the term of this patent is extended or adjusted under 35 U.S.C. 154(b) by 325 days.

(21) Appl. No.: 15/441,170

(22) Filed: Feb. 23, 2017

(65) Prior Publication Data
US 2018/0236268 A1     Aug. 23, 2018

(51) Int. Cl.
*A61N 5/10*     (2006.01)

(52) U.S. Cl.
CPC ........... *A61N 5/1067* (2013.01); *A61N 5/107* (2013.01); *A61N 5/1043* (2013.01);
(Continued)

(58) Field of Classification Search
CPC .......... A61N 2005/1087; A61N 5/1049; A61N 2005/1061; A61N 5/1071; A61N 5/1043;
(Continued)

(56) References Cited

U.S. PATENT DOCUMENTS

| 463,291 A | 11/1891 | Dodson |
| 773,508 A | 10/1904 | Leblanc |

(Continued)

FOREIGN PATENT DOCUMENTS

| CA | 2629333 A1 | 5/2007 |
| CN | 1377521 A | 10/2002 |

(Continued)

OTHER PUBLICATIONS

18th Japan Conference on Radiation and Radioisotopes [Japanese], Nov. 25-27, 1987, 9 pages.
(Continued)

*Primary Examiner* — Christine H Matthews
(74) *Attorney, Agent, or Firm* — Burns & Levinson LLP

(57) ABSTRACT

An example particle therapy system includes a particle beam output device to direct output of a particle beam; a treatment couch to support a patient containing an irradiation target, with the treatment couch being configured for movement; a movable device on which the particle beam output device is mounted for movement relative to the treatment couch; and a control system to provide automated control of at least one of the movable device or the treatment couch to position at least one of the particle beam or the irradiation target for treatment of the irradiation target with the particle beam and, following the treatment of the irradiation target with the particle beam, to provide automated control of at least one of the movable device or the treatment couch to reposition at least one of the particle beam or the irradiation target for additional treatment of the irradiation target with the particle beam.

62 Claims, 15 Drawing Sheets

(52) U.S. Cl.
CPC ......... *A61N 5/1045* (2013.01); *A61N 5/1049* (2013.01); *A61N 5/1065* (2013.01); *A61N 5/1069* (2013.01); *A61N 5/1081* (2013.01); *A61N 2005/1087* (2013.01); *A61N 2005/1095* (2013.01)

(58) Field of Classification Search
CPC .... A61N 5/1067; A61N 5/1069; A61N 5/107; A61N 5/1081
See application file for complete search history.

(56) References Cited

U.S. PATENT DOCUMENTS

| | | |
|---|---|---|
| 2,280,606 A | 4/1942 | Roberts |
| 2,492,324 A | 12/1949 | Salisbury |
| 2,615,129 A | 10/1952 | Mcmillan |
| 2,616,042 A | 10/1952 | Weeks |
| 2,659,000 A | 11/1953 | Salisbury |
| 2,701,304 A | 2/1955 | Paladino |
| 2,789,222 A | 4/1957 | Martin et al. |
| 2,958,327 A | 11/1960 | Geissmann |
| 3,024,379 A | 3/1962 | Verster |
| 3,175,131 A | 3/1965 | Burleigh et al. |
| 3,432,721 A | 3/1969 | Naydan et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,868,522 A | 2/1975 | Bigham et al. |
| 3,886,367 A | 5/1975 | Castle, Jr. |
| 3,925,676 A | 12/1975 | Bigham et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Taumann et al. |
| 4,230,129 A | 10/1980 | LeVeen |
| 4,256,966 A | 3/1981 | Heinz |
| 4,293,772 A | 10/1981 | Stieber |
| 4,336,505 A | 6/1982 | Meyer |
| 4,342,060 A | 7/1982 | Gibson |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,736,106 A | 4/1988 | Kashy et al. |
| 4,736,173 A | 4/1988 | Basil, Jr. et al. |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,763,483 A | 8/1988 | Olsen |
| 4,767,930 A | 8/1988 | Stieber et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,845,371 A | 7/1989 | Stieber |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,896,206 A | 1/1990 | Denham |
| 4,902,993 A | 2/1990 | Krevet |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,945,478 A | 7/1990 | Merickel et al. |
| 4,968,915 A | 11/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,006,759 A | 4/1991 | Krispel |
| 5,010,562 A | 4/1991 | Hernandez et al. |
| 5,012,111 A | 4/1991 | Ueda |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,046,078 A | 9/1991 | Hernandez et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,144,647 A | 9/1992 | Kikuchi |
| 5,148,032 A | 9/1992 | Hernandez |
| 5,166,531 A | 11/1992 | Huntzinger |
| 5,189,687 A | 2/1993 | Bova et al. |
| 5,191,706 A | 3/1993 | Cosden |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,285,166 A | 2/1994 | Hiramoto et al. |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,401,973 A | 3/1995 | McKeown et al. |
| 5,405,235 A | 4/1995 | Lebre et al. |
| 5,434,420 A | 7/1995 | McKeown et al. |
| 5,440,133 A | 8/1995 | Moyers et al. |
| 5,451,794 A | 9/1995 | McKeown et al. |
| 5,461,773 A | 10/1995 | Kawaguchi |
| 5,463,291 A | 10/1995 | Carroll et al. |
| 5,464,411 A | 11/1995 | Schulte et al. |
| 5,492,922 A | 2/1996 | Palkowitz |
| 5,511,549 A | 4/1996 | Legg et al. |
| 5,521,469 A | 5/1996 | Laisne |
| 5,538,942 A | 7/1996 | Koyama et al. |
| 5,549,616 A | 8/1996 | Schulte et al. |
| 5,561,697 A | 10/1996 | Takafuji et al. |
| 5,585,642 A | 12/1996 | Britton et al. |
| 5,633,747 A | 5/1997 | Nikoonahad |
| 5,635,721 A | 6/1997 | Bardi et al. |
| 5,668,371 A | 9/1997 | Deasy et al. |
| 5,672,878 A | 9/1997 | Yao |
| 5,691,679 A | 11/1997 | Ackermann et al. |
| 5,726,448 A | 3/1998 | Smith et al. |
| 5,727,554 A | 3/1998 | Kalend et al. |
| 5,730,745 A | 3/1998 | Schulte et al. |
| 5,748,703 A | 5/1998 | Cosman |
| 5,751,781 A | 5/1998 | Brown et al. |
| 5,764,723 A | 6/1998 | Weinberger et al. |

(56) References Cited

U.S. PATENT DOCUMENTS

| | | |
|---|---|---|
| 5,778,047 A | 7/1998 | Mansfield et al. |
| 5,783,914 A | 7/1998 | Hiramoto et al. |
| 5,784,431 A | 7/1998 | Kalend et al. |
| 5,797,924 A | 8/1998 | Schulte et al. |
| 5,811,944 A | 9/1998 | Sampayan et al. |
| 5,818,058 A | 10/1998 | Nakanishi et al. |
| 5,821,705 A | 10/1998 | Caporaso et al. |
| 5,825,845 A | 10/1998 | Blair et al. |
| 5,841,237 A | 11/1998 | Alton |
| 5,846,043 A | 12/1998 | Spath |
| 5,851,182 A | 12/1998 | Sahadevan |
| 5,866,912 A | 2/1999 | Slater et al. |
| 5,874,811 A | 2/1999 | Finlan et al. |
| 5,895,926 A | 4/1999 | Britton et al. |
| 5,920,601 A | 7/1999 | Nigg et al. |
| 5,929,458 A | 7/1999 | Nemezawa et al. |
| 5,963,615 A | 10/1999 | Egley et al. |
| 5,986,274 A | 11/1999 | Akiyama et al. |
| 5,993,373 A | 11/1999 | Nonaka et al. |
| 6,008,499 A | 12/1999 | Hiramoto et al. |
| 6,034,377 A | 3/2000 | Pu |
| 6,057,655 A | 5/2000 | Jongen |
| 6,061,426 A | 5/2000 | Linders et al. |
| 6,064,807 A | 5/2000 | Arai et al. |
| 6,066,851 A | 5/2000 | Madono et al. |
| 6,080,992 A | 6/2000 | Nonaka et al. |
| 6,087,670 A | 7/2000 | Hiramoto et al. |
| 6,087,672 A | 7/2000 | Matsuda et al. |
| 6,094,760 A | 8/2000 | Nonaka et al. |
| 6,118,848 A | 9/2000 | Reiffel |
| 6,140,021 A | 10/2000 | Nakasuji et al. |
| 6,144,875 A | 11/2000 | Schweikard et al. |
| 6,158,708 A | 12/2000 | Egley et al. |
| 6,207,952 B1 | 3/2001 | Kan et al. |
| 6,219,403 B1 | 4/2001 | Nishihara |
| 6,222,905 B1 | 4/2001 | Yoda et al. |
| 6,241,671 B1 | 6/2001 | Ritter et al. |
| 6,246,066 B1 | 6/2001 | Yuehu |
| 6,256,591 B1 | 7/2001 | Yoda et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riaziat et al. |
| 6,307,914 B1 | 10/2001 | Kunieda et al. |
| 6,316,776 B1 | 11/2001 | Hiramoto et al. |
| 6,366,021 B1 | 4/2002 | Meddaugh et al. |
| 6,369,585 B2 | 4/2002 | Yao |
| 6,380,545 B1 | 4/2002 | Yan |
| 6,407,505 B1 | 6/2002 | Bertsche |
| 6,417,634 B1 | 7/2002 | Bergstrom |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,441,569 B1 | 8/2002 | Janzow |
| 6,443,349 B1 | 9/2002 | Van Der Burg |
| 6,459,769 B1 | 10/2002 | Cosman |
| 6,465,957 B1 | 10/2002 | Whitham et al. |
| 6,472,834 B2 | 10/2002 | Hiramoto et al. |
| 6,476,403 B1 | 11/2002 | Dolinskii et al. |
| 6,492,922 B1 | 12/2002 | New |
| 6,493,424 B2 | 12/2002 | Whitham |
| 6,498,444 B1 | 12/2002 | Hanna et al. |
| 6,501,981 B1 | 12/2002 | Schweikard et al. |
| 6,519,316 B1 | 2/2003 | Collins |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,617,598 B1 | 9/2003 | Matsuda |
| 6,621,889 B1 | 9/2003 | Mostafavi |
| 6,630,675 B2 | 10/2003 | Ghelmansarai |
| 6,639,234 B1 | 10/2003 | Badura et al. |
| 6,646,383 B2 | 11/2003 | Bertsche et al. |
| 6,670,618 B1 | 12/2003 | Hartmann et al. |
| 6,683,162 B2 | 1/2004 | Scheinberg et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,714,620 B2 | 3/2004 | Caflisch et al. |
| 6,717,162 B1 | 4/2004 | Jongen |
| 6,745,072 B1 | 6/2004 | Badura et al. |
| 6,769,806 B2 | 8/2004 | Moyers |
| 6,774,383 B2 | 8/2004 | Norimine et al. |
| 6,777,689 B2 | 8/2004 | Nelson |
| 6,777,700 B2 | 8/2004 | Yanagisawa et al. |
| 6,780,149 B1 | 8/2004 | Schulte |
| 6,792,078 B2 | 9/2004 | Kato et al. |
| 6,799,068 B1 | 9/2004 | Hartmann et al. |
| 6,800,866 B2 | 10/2004 | Amemiya et al. |
| 6,803,591 B2 | 10/2004 | Muramatsu et al. |
| 6,814,694 B1 | 11/2004 | Pedroni |
| 6,819,743 B2 | 11/2004 | Kato et al. |
| 6,822,244 B2 | 11/2004 | Beloussov et al. |
| 6,823,045 B2 | 11/2004 | Kato et al. |
| 6,853,142 B2 | 2/2005 | Chistyakov |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,873,123 B2 | 3/2005 | Marchand et al. |
| 6,878,951 B2 | 4/2005 | Ma |
| 6,891,177 B1 | 5/2005 | Kraft et al. |
| 6,891,924 B1 | 5/2005 | Yoda et al. |
| 6,894,300 B2 | 5/2005 | Reimoser et al. |
| 6,897,451 B2 | 5/2005 | Kaercher et al. |
| 6,914,396 B1 | 7/2005 | Symons et al. |
| 6,931,100 B2 | 8/2005 | Kato et al. |
| 6,936,832 B2 | 8/2005 | Norimine et al. |
| 6,953,943 B2 | 10/2005 | Yanagisawa et al. |
| 6,965,116 B1 | 11/2005 | Wagner et al. |
| 6,969,194 B1 | 11/2005 | Nafstadius |
| 6,979,832 B2 | 12/2005 | Yanagisawa et al. |
| 6,984,835 B2 | 1/2006 | Harada |
| 6,992,312 B2 | 1/2006 | Yanagisawa et al. |
| 6,993,112 B2 | 1/2006 | Hesse |
| 6,998,604 B2 | 2/2006 | Nishizawa et al. |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,781 B2 | 5/2006 | Adamec et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| 7,060,997 B2 | 6/2006 | Norimine et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,091,478 B2 | 8/2006 | Haberer |
| 7,102,144 B2 | 9/2006 | Matsuda et al. |
| 7,122,811 B2 | 10/2006 | Matsuda et al. |
| 7,122,966 B2 | 10/2006 | Norling et al. |
| 7,122,978 B2 | 10/2006 | Nakanishi et al. |
| 7,135,678 B2 | 11/2006 | Wang et al. |
| 7,138,771 B2 | 11/2006 | Bechthold et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |

(56) References Cited

U.S. PATENT DOCUMENTS

| | | |
|---|---|---|
| 7,227,161 B2 | 6/2007 | Matsuda et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,424 B2 | 8/2007 | Moriyama et al. |
| 7,262,565 B2 | 8/2007 | Fujisawa |
| 7,268,358 B2 | 9/2007 | Ma et al. |
| 7,274,018 B2 | 9/2007 | Adamec et al. |
| 7,280,633 B2 | 10/2007 | Cheng et al. |
| 7,295,649 B2 | 11/2007 | Johnsen |
| 7,297,967 B2 | 11/2007 | Yanagisawa et al. |
| 7,301,162 B2 | 11/2007 | Matsuda et al. |
| 7,307,264 B2 | 12/2007 | Brusasco et al. |
| 7,317,192 B2 | 1/2008 | Ma |
| 7,318,805 B2 | 1/2008 | Schweikard et al. |
| 7,319,231 B2 | 1/2008 | Moriyama et al. |
| 7,319,336 B2 | 1/2008 | Baur et al. |
| 7,331,713 B2 | 2/2008 | Moyers |
| 7,332,880 B2 | 2/2008 | Ina et al. |
| 7,345,291 B2 | 3/2008 | Kats |
| 7,345,292 B2 | 3/2008 | Moriyama et al. |
| 7,348,557 B2 | 3/2008 | Armit |
| 7,348,579 B2 | 3/2008 | Pedroni |
| 7,351,988 B2 | 4/2008 | Naumann et al. |
| 7,355,189 B2 | 4/2008 | Yanagisawa et al. |
| 7,368,740 B2 | 5/2008 | Beloussov et al. |
| 7,372,053 B2 | 5/2008 | Yamashita et al. |
| 7,378,672 B2 | 5/2008 | Harada |
| 7,381,979 B2 | 6/2008 | Yamashita et al. |
| 7,386,099 B1 | 6/2008 | Kasper et al. |
| 7,397,054 B2 | 7/2008 | Natori et al. |
| 7,397,901 B1 | 7/2008 | Johnsen |
| 7,398,309 B2 | 7/2008 | Baumann et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,402,963 B2 | 7/2008 | Sliski et al. |
| 7,405,407 B2 | 7/2008 | Hiramoto et al. |
| 7,425,717 B2 | 9/2008 | Matsuda et al. |
| 7,432,516 B2 | 10/2008 | Peggs et al. |
| 7,439,528 B2 | 10/2008 | Nishiuchi et al. |
| 7,446,328 B2 | 11/2008 | Rigney et al. |
| 7,446,490 B2 | 11/2008 | Jongen et al. |
| 7,449,701 B2 | 11/2008 | Fujimaki et al. |
| 7,453,076 B2 | 11/2008 | Welch et al. |
| 7,465,944 B2 | 12/2008 | Ueno et al. |
| 7,466,085 B2 | 12/2008 | Nutt |
| 7,468,506 B2 | 12/2008 | Rogers et al. |
| 7,473,913 B2 | 1/2009 | Hermann et al. |
| 7,476,867 B2 | 1/2009 | Fritsch et al. |
| 7,476,883 B2 | 1/2009 | Nutt |
| 7,482,606 B2 | 1/2009 | Groezinger et al. |
| 7,492,556 B2 | 2/2009 | Atkins et al. |
| 7,507,975 B2 | 3/2009 | Mohr |
| 7,525,104 B2 | 4/2009 | Harada |
| 7,531,818 B2 | 5/2009 | Brahme |
| 7,541,905 B2 | 6/2009 | Antaya |
| 7,547,901 B2 | 6/2009 | Guertin et al. |
| 7,554,096 B2 | 6/2009 | Ward et al. |
| 7,554,097 B2 | 6/2009 | Ward et al. |
| 7,554,275 B2 | 6/2009 | Amaldi |
| 7,555,103 B2 | 6/2009 | Johnsen |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 7,560,698 B2 | 7/2009 | Rietzel |
| 7,560,715 B2 | 7/2009 | Pedroni |
| 7,560,717 B2 | 7/2009 | Matsuda et al. |
| 7,567,694 B2 | 7/2009 | Lu et al. |
| 7,574,251 B2 | 8/2009 | Lu et al. |
| 7,576,499 B2 | 8/2009 | Caporaso et al. |
| 7,579,603 B2 | 8/2009 | Birgy et al. |
| 7,579,610 B2 | 8/2009 | Grozinger et al. |
| 7,582,866 B2 | 9/2009 | Furuhashi et al. |
| 7,582,885 B2 | 9/2009 | Katagiri et al. |
| 7,582,886 B2 | 9/2009 | Trbojevic |
| 7,586,112 B2 | 9/2009 | Chiba et al. |
| 7,598,497 B2 | 10/2009 | Yamamoto et al. |
| 7,609,009 B2 | 10/2009 | Tanaka et al. |
| 7,609,809 B2 | 10/2009 | Kapatoes et al. |
| 7,609,811 B1 | 10/2009 | Siljamaki et al. |
| 7,615,942 B2 | 11/2009 | Sanders et al. |
| 7,626,347 B2 | 12/2009 | Sliski et al. |
| 7,629,598 B2 | 12/2009 | Harada |
| 7,629,599 B2 | 12/2009 | Hashimoto |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,656,258 B1 | 2/2010 | Antaya et al. |
| 7,659,521 B2 | 2/2010 | Pedroni |
| 7,659,528 B2 | 2/2010 | Uematsu |
| 7,668,291 B2 | 2/2010 | Nord et al. |
| 7,672,429 B2 | 3/2010 | Urano et al. |
| 7,679,049 B2 | 3/2010 | Rietzel |
| 7,679,073 B2 | 3/2010 | Urano et al. |
| 7,682,078 B2 | 3/2010 | Rietzel |
| 7,692,166 B2 | 4/2010 | Muraki et al. |
| 7,692,168 B2 | 4/2010 | Moriyama et al. |
| 7,696,499 B2 | 4/2010 | Miller et al. |
| 7,696,847 B2 | 4/2010 | Antaya |
| 7,701,677 B2 | 4/2010 | Schultz et al. |
| 7,709,818 B2 | 5/2010 | Matsuda et al. |
| 7,710,051 B2 | 5/2010 | Caporaso et al. |
| 7,718,982 B2 | 5/2010 | Sliski et al. |
| 7,723,036 B2 | 5/2010 | Racila et al. |
| 7,728,311 B2 | 6/2010 | Gall |
| 7,746,978 B2 | 6/2010 | Cheng et al. |
| 7,755,068 B2 | 7/2010 | Ma et al. |
| 7,755,305 B2 | 7/2010 | Umezawa et al. |
| 7,759,642 B2 | 7/2010 | Nir |
| 7,763,867 B2 | 7/2010 | Birgy et al. |
| 7,763,873 B2 | 7/2010 | Flynn et al. |
| 7,767,988 B2 | 8/2010 | Kaiser et al. |
| 7,770,231 B2 | 8/2010 | Prater et al. |
| 7,772,577 B2 | 8/2010 | Saito et al. |
| 7,773,723 B2 | 8/2010 | Nord et al. |
| 7,773,788 B2 | 8/2010 | Lu et al. |
| 7,778,488 B2 | 8/2010 | Nord et al. |
| 7,783,010 B2 | 8/2010 | Clayton |
| 7,784,124 B2 | 8/2010 | Long et al. |
| 7,784,127 B2 | 8/2010 | Kuro et al. |
| 7,786,433 B2 | 8/2010 | Gunzert-Marx et al. |
| 7,786,451 B2 | 8/2010 | Ward et al. |
| 7,786,452 B2 | 8/2010 | Ward et al. |
| 7,789,560 B2 | 9/2010 | Moyers |
| 7,791,051 B2 | 9/2010 | Beloussov et al. |
| 7,796,731 B2 | 9/2010 | Nord et al. |
| 7,801,269 B2 | 9/2010 | Cravens et al. |
| 7,801,270 B2 | 9/2010 | Nord et al. |
| 7,801,988 B2 | 9/2010 | Baumann et al. |
| 7,807,982 B2 | 10/2010 | Nishiuchi et al. |
| 7,809,107 B2 | 10/2010 | Nord et al. |
| 7,812,319 B2 | 10/2010 | Diehl et al. |
| 7,812,326 B2 | 10/2010 | Grozinger et al. |
| 7,816,657 B2 | 10/2010 | Hansmann et al. |
| 7,817,778 B2 | 10/2010 | Nord et al. |
| 7,817,836 B2 | 10/2010 | Chao et al. |
| 7,818,045 B2 | 10/2010 | Rietzel |
| 7,825,388 B2 | 11/2010 | Nihongi et al. |
| 7,826,593 B2 | 11/2010 | Svensson et al. |
| 7,834,334 B2 | 11/2010 | Grozinger et al. |
| 7,834,336 B2 | 11/2010 | Boeh et al. |
| 7,835,494 B2 | 11/2010 | Nord et al. |
| 7,835,502 B2 | 11/2010 | Spence et al. |
| 7,839,972 B2 | 11/2010 | Ruchala et al. |
| 7,839,973 B2 | 11/2010 | Nord et al. |
| 7,848,488 B2 | 12/2010 | Mansfield |
| 7,857,756 B2 | 12/2010 | Warren et al. |
| 7,858,592 B2 | 12/2010 | Shames et al. |
| 7,860,216 B2 | 12/2010 | Jongen et al. |
| 7,860,550 B2 | 12/2010 | Saracen et al. |
| 7,868,301 B2 | 1/2011 | Diehl |
| 7,875,846 B2 | 1/2011 | Gunzert-Marx et al. |

(56) References Cited

U.S. PATENT DOCUMENTS

| | | |
|---|---|---|
| 7,875,861 B2 | 1/2011 | Huttenberger et al. |
| 7,875,868 B2 | 1/2011 | Moriyama et al. |
| 7,881,431 B2 | 2/2011 | Aoi et al. |
| 7,894,574 B1 | 2/2011 | Nord et al. |
| 7,903,781 B2 | 3/2011 | Foland et al. |
| 7,906,769 B2 | 3/2011 | Blasche et al. |
| 7,907,987 B2 | 3/2011 | Dempsey |
| 7,914,734 B2 | 3/2011 | Livingston |
| 7,919,765 B2 | 4/2011 | Timmer |
| 7,920,040 B2 | 4/2011 | Antaya et al. |
| 7,920,675 B2 | 4/2011 | Lomax et al. |
| 7,928,415 B2 | 4/2011 | Bert et al. |
| 7,934,869 B2 | 5/2011 | Ivanov et al. |
| 7,939,809 B2 | 5/2011 | Balakin |
| 7,940,881 B2 | 5/2011 | Jongen et al. |
| 7,940,894 B2 | 5/2011 | Balakin |
| 7,943,913 B2 | 5/2011 | Balakin |
| 7,947,969 B2 | 5/2011 | Pu |
| 7,949,096 B2 | 5/2011 | Cheng et al. |
| 7,950,587 B2 | 5/2011 | Henson et al. |
| 7,953,205 B2 | 5/2011 | Balakin |
| 7,957,508 B2 | 6/2011 | Brooks et al. |
| 7,960,710 B2 | 6/2011 | Kruip et al. |
| 7,961,844 B2 | 6/2011 | Takeda et al. |
| 7,977,648 B2 | 7/2011 | Westerly et al. |
| 7,977,656 B2 | 7/2011 | Fujimaki et al. |
| 7,977,657 B2 | 7/2011 | Flynn et al. |
| 7,982,198 B2 | 7/2011 | Nishiuchi et al. |
| 7,982,416 B2 | 7/2011 | Tanaka et al. |
| 7,984,715 B2 | 7/2011 | Moyers |
| 7,986,768 B2 | 7/2011 | Nord et al. |
| 7,987,053 B2 | 7/2011 | Schaffner |
| 7,989,785 B2 | 8/2011 | Emhofer et al. |
| 7,990,524 B2 | 8/2011 | Jureller et al. |
| 7,997,553 B2 | 8/2011 | Sloan et al. |
| 8,002,466 B2 | 8/2011 | Von Neubeck et al. |
| 8,003,964 B2 | 8/2011 | Stark et al. |
| 8,009,803 B2 | 8/2011 | Nord et al. |
| 8,009,804 B2 | 8/2011 | Siljamaki et al. |
| 8,016,336 B2 | 9/2011 | Messinger et al. |
| 8,039,822 B2 | 10/2011 | Rietzel |
| 8,041,006 B2 | 10/2011 | Boyden et al. |
| 8,044,364 B2 | 10/2011 | Yamamoto |
| 8,045,679 B2 | 10/2011 | Balakin |
| 8,049,187 B2 | 11/2011 | Tachikawa |
| 8,053,508 B2 | 11/2011 | Korkut et al. |
| 8,053,739 B2 | 11/2011 | Rietzel |
| 8,053,745 B2 | 11/2011 | Moore |
| 8,053,746 B2 | 11/2011 | Timmer et al. |
| 8,063,381 B2 | 11/2011 | Tsoupas et al. |
| 8,067,748 B2 | 11/2011 | Balakin |
| 8,069,675 B2 | 12/2011 | Radovinsky et al. |
| 8,071,966 B2 | 12/2011 | Kaiser et al. |
| 8,080,801 B2 | 12/2011 | Safai |
| 8,085,899 B2 | 12/2011 | Nord et al. |
| 8,089,054 B2 | 1/2012 | Balakin |
| 8,090,074 B2 | 1/2012 | Filiberti et al. |
| 8,093,564 B2 | 1/2012 | Balakin |
| 8,093,568 B2 | 1/2012 | MacKie et al. |
| 8,111,125 B2 | 2/2012 | Antaya et al. |
| 8,129,694 B2 | 3/2012 | Balakin |
| 8,129,699 B2 | 3/2012 | Balakin |
| 8,144,832 B2 | 3/2012 | Balakin |
| 8,153,989 B2 | 4/2012 | Tachikawa et al. |
| 8,154,001 B2 | 4/2012 | Flynn et al. |
| 8,163,709 B2 | 4/2012 | Kodym et al. |
| 8,173,981 B2 | 5/2012 | Trbojevic |
| 8,178,859 B2 | 5/2012 | Balakin |
| 8,183,541 B2 | 5/2012 | Wilkens et al. |
| 8,188,688 B2 | 5/2012 | Balakin |
| 8,189,889 B2 | 5/2012 | Pearlstein et al. |
| 8,190,233 B2 | 5/2012 | Dempsey |
| 8,198,607 B2 | 6/2012 | Balakin |
| 8,207,656 B2 | 6/2012 | Baumgartner et al. |
| 8,222,613 B2 | 7/2012 | Tajiri et al. |
| 8,227,768 B2 | 7/2012 | Smick et al. |
| 8,229,072 B2 | 7/2012 | Balakin |
| 8,232,536 B2 | 7/2012 | Harada |
| 8,238,513 B2 | 8/2012 | Ma |
| 8,253,121 B2 | 8/2012 | Gnutzmann et al. |
| 8,254,521 B2 | 8/2012 | Brooks et al. |
| 8,263,954 B2 | 9/2012 | Iwata |
| 8,283,645 B2 | 10/2012 | Guneysel |
| 8,288,742 B2 | 10/2012 | Balakin |
| 8,291,717 B2 | 10/2012 | Radovinsky et al. |
| 8,294,127 B2 | 10/2012 | Tachibana |
| 8,304,725 B2 | 11/2012 | Komuro et al. |
| 8,304,750 B2 | 11/2012 | Preikszas et al. |
| 8,309,941 B2 | 11/2012 | Balakin |
| 8,330,132 B2 | 12/2012 | Guertin et al. |
| 8,334,520 B2 | 12/2012 | Otaka et al. |
| 8,335,397 B2 | 12/2012 | Takane et al. |
| 8,344,340 B2 | 1/2013 | Gall et al. |
| 8,350,214 B2 | 1/2013 | Otaki et al. |
| 8,351,571 B2 | 1/2013 | Brinks et al. |
| 8,354,656 B2 | 1/2013 | Beloussov et al. |
| 8,368,038 B2 | 2/2013 | Balakin |
| 8,368,043 B2 | 2/2013 | Havelange et al. |
| 8,373,143 B2 | 2/2013 | Balakin |
| 8,373,145 B2 | 2/2013 | Balakin |
| 8,373,146 B2 | 2/2013 | Balakin |
| 8,374,314 B2 | 2/2013 | Balakin |
| 8,378,299 B2 | 2/2013 | Frosien |
| 8,378,311 B2 | 2/2013 | Balakin |
| 8,378,312 B1 | 2/2013 | Gordon et al. |
| 8,378,321 B2 | 2/2013 | Balakin |
| 8,382,943 B2 | 2/2013 | Clark |
| 8,384,053 B2 | 2/2013 | Balakin |
| 8,389,949 B2 | 3/2013 | Harada et al. |
| 8,399,866 B2 | 3/2013 | Balakin |
| 8,405,042 B2 | 3/2013 | Honda et al. |
| 8,405,056 B2 | 3/2013 | Amaldi et al. |
| 8,415,643 B2 | 4/2013 | Balakin |
| 8,416,918 B2 | 4/2013 | Nord et al. |
| 8,421,041 B2 | 4/2013 | Balakin |
| 8,426,833 B2 | 4/2013 | Trbojevic |
| 8,436,323 B2 | 5/2013 | Iseki et al. |
| 8,436,325 B2 | 5/2013 | Noda et al. |
| 8,436,327 B2 | 5/2013 | Balakin |
| 8,440,987 B2 | 5/2013 | Stephani et al. |
| 8,445,872 B2 | 5/2013 | Behrens et al. |
| 8,459,714 B2 | 6/2013 | Pomper et al. |
| 8,461,559 B2 | 6/2013 | Lomax |
| 8,466,441 B2 | 6/2013 | Iwata et al. |
| 8,472,583 B2 | 6/2013 | Star-Lack et al. |
| 8,481,951 B2 | 7/2013 | Jongen et al. |
| 8,483,357 B2 | 7/2013 | Siljamaki et al. |
| 8,487,278 B2 | 7/2013 | Balakin |
| 8,487,282 B2 | 7/2013 | Iseki et al. |
| 8,507,195 B2 | 8/2013 | Richer et al. |
| 8,519,365 B2 | 8/2013 | Balakin |
| 8,525,419 B2 | 9/2013 | Smith et al. |
| 8,525,447 B2 | 9/2013 | Antaya |
| 8,525,448 B2 | 9/2013 | Tanaka et al. |
| 8,536,548 B2 | 9/2013 | Otani et al. |
| 8,541,762 B2 | 9/2013 | Claereboudt et al. |
| 8,546,769 B2 | 10/2013 | Uno |
| 8,552,406 B2 | 10/2013 | Phaneuf et al. |
| 8,552,408 B2 | 10/2013 | Hanawa et al. |
| 8,558,461 B2 | 10/2013 | Poehlmann-Martins et al. |
| 8,558,485 B2 | 10/2013 | Antaya |
| 8,565,377 B2 | 10/2013 | Robar et al. |
| 8,569,717 B2 | 10/2013 | Balakin |
| 8,575,563 B2 | 11/2013 | Cameron et al. |
| 8,575,564 B2 | 11/2013 | Iwata |
| 8,575,579 B2 | 11/2013 | Moskvin et al. |
| 8,581,215 B2 | 11/2013 | Balakin |
| 8,581,218 B2 | 11/2013 | Fujimoto et al. |
| 8,581,523 B2 | 11/2013 | Gall et al. |
| 8,581,525 B2 | 11/2013 | Antaya et al. |
| 8,586,948 B2 | 11/2013 | Pu et al. |
| 8,598,543 B2 | 12/2013 | Balakin |
| 8,601,116 B2 | 12/2013 | Baumann et al. |
| 8,604,454 B2 | 12/2013 | Guertin et al. |

(56) References Cited

U.S. PATENT DOCUMENTS

| | | |
|---|---|---|
| 8,613,694 B2 | 12/2013 | Walsh |
| 8,614,554 B2 | 12/2013 | Balakin |
| 8,614,612 B2 | 12/2013 | Antaya et al. |
| 8,618,519 B2 | 12/2013 | Ueda |
| 8,618,521 B2 | 12/2013 | Loo et al. |
| 8,619,242 B2 | 12/2013 | Suzuki |
| 8,624,528 B2 | 1/2014 | Balakin |
| 8,625,739 B2 | 1/2014 | Balakin |
| 8,627,822 B2 | 1/2014 | Balakin |
| 8,632,448 B1 | 1/2014 | Schulte et al. |
| 8,633,160 B2 | 1/2014 | Belmares et al. |
| 8,637,818 B2 | 1/2014 | Balakin |
| 8,637,839 B2 | 1/2014 | Brauer |
| 8,642,978 B2 | 2/2014 | Balakin |
| 8,643,314 B2 | 2/2014 | Touchi |
| 8,644,571 B1 | 2/2014 | Schulte et al. |
| 8,653,314 B2 | 2/2014 | Pelati et al. |
| 8,653,473 B2 | 2/2014 | Yajima |
| 8,657,354 B2 | 2/2014 | Pomper et al. |
| 8,657,743 B2 | 2/2014 | Rietzel et al. |
| 8,688,197 B2 | 4/2014 | Balakin |
| 8,702,578 B2 | 4/2014 | Fahrig et al. |
| 8,710,462 B2 | 4/2014 | Balakin |
| 8,712,011 B2 | 4/2014 | Robar et al. |
| 8,716,663 B2 | 5/2014 | Brusasco et al. |
| 8,718,231 B2 | 5/2014 | Balakin |
| 8,735,848 B2 | 5/2014 | Asaba |
| 8,748,852 B2 | 6/2014 | Jongen |
| 8,750,453 B2 | 6/2014 | Cheng et al. |
| 8,754,386 B2 | 6/2014 | Iwata |
| 8,766,217 B2 | 7/2014 | Balakin |
| 8,766,218 B2 | 7/2014 | Jongen |
| 8,771,754 B2 | 7/2014 | Hallahan |
| 8,791,435 B2 | 7/2014 | Balakin |
| 8,791,656 B1 | 7/2014 | Zwart et al. |
| 8,796,648 B2 | 8/2014 | Fujimoto et al. |
| 8,822,965 B2 | 9/2014 | Asaba |
| 8,835,885 B2 | 9/2014 | Ogasawara |
| 8,847,179 B2 | 9/2014 | Fujitaka et al. |
| 8,859,264 B2 | 10/2014 | Bert et al. |
| 8,866,109 B2 | 10/2014 | Sasai |
| 8,890,097 B2 | 11/2014 | Iwata |
| 8,896,239 B2 | 11/2014 | Balakin |
| 8,897,857 B2 | 11/2014 | Tome et al. |
| 8,901,509 B2 | 12/2014 | Balakin |
| 8,901,520 B2 | 12/2014 | Tachibana et al. |
| 8,907,309 B2 | 12/2014 | Spotts |
| 8,907,311 B2 | 12/2014 | Gall et al. |
| 8,907,594 B2 | 12/2014 | Begg et al. |
| 8,916,838 B2 | 12/2014 | Claereboudt et al. |
| 8,916,841 B2 | 12/2014 | Totake et al. |
| 8,916,843 B2 | 12/2014 | Gall et al. |
| 8,927,946 B2 | 1/2015 | Behrens et al. |
| 8,927,950 B2 | 1/2015 | Gall et al. |
| 8,933,650 B2 | 1/2015 | O'Neal, III et al. |
| 8,941,083 B2 | 1/2015 | Stark et al. |
| 8,941,084 B2 | 1/2015 | Balakin |
| 8,941,086 B2 | 1/2015 | Yajima |
| 8,947,021 B2 | 2/2015 | Tsutsui |
| 8,948,341 B2 | 2/2015 | Beckman |
| 8,952,343 B2 | 2/2015 | Stephani et al. |
| 8,952,634 B2 | 2/2015 | Sliski et al. |
| 8,957,396 B2 | 2/2015 | Balakin |
| 8,963,111 B2 | 2/2015 | Claereboudt et al. |
| 8,963,112 B1 | 2/2015 | Balakin |
| 8,964,936 B2 | 2/2015 | Brooks et al. |
| 8,969,834 B2 | 3/2015 | Balakin |
| 8,970,137 B2 | 3/2015 | Gall et al. |
| 8,971,363 B2 | 3/2015 | Levecq et al. |
| 8,975,600 B2 | 3/2015 | Balakin |
| 8,975,602 B2 | 3/2015 | Huber et al. |
| 8,975,836 B2 | 3/2015 | Bromberg et al. |
| 8,986,186 B2 | 3/2015 | Zhang et al. |
| 8,993,522 B2 | 3/2015 | Vidyasagar et al. |
| 9,006,693 B2 | 4/2015 | Sasai |
| 9,007,740 B2 | 4/2015 | Touchi |
| 9,012,832 B2 | 4/2015 | Bert et al. |
| 9,012,866 B2 | 4/2015 | Benna et al. |
| 9,012,873 B2 | 4/2015 | Fujimoto et al. |
| 9,018,601 B2 | 4/2015 | Balakin |
| 9,018,603 B2 | 4/2015 | Loo et al. |
| 9,024,256 B2 | 5/2015 | Ruan et al. |
| 9,029,760 B2 | 5/2015 | Beddar et al. |
| 9,044,600 B2 | 6/2015 | Balakin |
| 9,056,199 B2 | 6/2015 | Balakin |
| 9,058,910 B2 | 6/2015 | Balakin |
| 9,060,998 B2 | 6/2015 | Stockfleth |
| 9,061,142 B2 | 6/2015 | Vilsmeier |
| 9,061,143 B2 | 6/2015 | Sasai et al. |
| 9,084,887 B2 | 7/2015 | Schulte et al. |
| 9,084,890 B2 | 7/2015 | Iwata |
| 9,089,696 B2 | 7/2015 | Verhaegen et al. |
| 9,093,209 B2 | 7/2015 | Jongen |
| 9,095,040 B2 | 7/2015 | Balakin |
| 9,108,050 B2 | 8/2015 | Bula et al. |
| 9,114,253 B2 | 8/2015 | Dempsey |
| 9,142,385 B1 | 9/2015 | Iwanaga |
| 9,155,186 B2 | 10/2015 | Zwart et al. |
| 9,155,908 B2 | 10/2015 | Meltsner et al. |
| 9,185,789 B2 | 11/2015 | Zwart et al. |
| 9,186,525 B2 | 11/2015 | Prieels et al. |
| 9,188,685 B2 | 11/2015 | Takayanagi et al. |
| 9,196,082 B2 | 11/2015 | Pearlstein et al. |
| 9,220,920 B2 | 12/2015 | Schulte et al. |
| 9,220,923 B2 | 12/2015 | Yajima et al. |
| 9,237,640 B2 | 1/2016 | Abs et al. |
| 9,237,642 B2 | 1/2016 | Kleeven |
| 9,245,336 B2 | 1/2016 | Mallya et al. |
| 9,254,396 B2 | 2/2016 | Mihaylov |
| 9,259,155 B2 | 2/2016 | Bharat et al. |
| 9,271,385 B2 | 2/2016 | Verbruggen et al. |
| 9,283,406 B2 | 3/2016 | Prieels |
| 9,283,407 B2 | 3/2016 | Benna et al. |
| 9,289,140 B2 | 3/2016 | Ross et al. |
| 9,289,624 B2 | 3/2016 | Jongen |
| 9,297,912 B2 | 3/2016 | Campbell et al. |
| 9,301,384 B2 | 3/2016 | Zwart et al. |
| 9,302,121 B2 | 4/2016 | Totake et al. |
| 9,305,742 B2 | 4/2016 | Aptaker et al. |
| 9,355,784 B2 | 5/2016 | Abs |
| 9,364,688 B2 | 6/2016 | Pausch et al. |
| 9,370,089 B2 | 6/2016 | Ungaro et al. |
| 9,381,379 B2 | 7/2016 | Beckman |
| 9,393,443 B2 | 7/2016 | Fujimoto et al. |
| 9,417,302 B2 | 8/2016 | Kuhn |
| 9,451,688 B2 | 9/2016 | Jongen |
| 9,451,689 B2 | 9/2016 | Tsutsui |
| 9,452,300 B2 | 9/2016 | Anferov |
| 9,452,301 B2 | 9/2016 | Gall et al. |
| 9,468,608 B2 | 10/2016 | Lin et al. |
| 9,492,684 B2 | 11/2016 | Takayanagi et al. |
| 2001/0022502 A1 | 9/2001 | Akiyama et al. |
| 2002/0058007 A1 | 5/2002 | Scheinberg et al. |
| 2002/0101959 A1 | 8/2002 | Kato et al. |
| 2002/0172317 A1 | 11/2002 | Maksimchuk et al. |
| 2003/0048080 A1 | 3/2003 | Amemiya et al. |
| 2003/0125622 A1 | 7/2003 | Schweikard et al. |
| 2003/0136924 A1 | 7/2003 | Kraft et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0234369 A1 | 12/2003 | Glukhoy |
| 2004/0000650 A1 | 1/2004 | Yanagisawa et al. |
| 2004/0017888 A1 | 1/2004 | Seppi et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0155206 A1 | 8/2004 | Marchand et al. |
| 2004/0159795 A1 | 8/2004 | Kaercher et al. |

(56) References Cited

U.S. PATENT DOCUMENTS

| | | |
|---|---|---|
| 2004/0164254 A1 | 8/2004 | Beloussov et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0190680 A1 | 9/2004 | Chang |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |
| 2004/0232356 A1 | 11/2004 | Norimine et al. |
| 2004/0240626 A1 | 12/2004 | Moyers |
| 2005/0029472 A1 | 2/2005 | Ueno et al. |
| 2005/0051740 A1 | 3/2005 | Yanagisawa et al. |
| 2005/0058245 A1 | 3/2005 | Ein-Gal |
| 2005/0072940 A1 | 4/2005 | Beloussov et al. |
| 2005/0079235 A1 | 4/2005 | Stockfleth |
| 2005/0087700 A1 | 4/2005 | Tadokoro et al. |
| 2005/0089141 A1 | 4/2005 | Brown |
| 2005/0099145 A1 | 5/2005 | Nishiuchi et al. |
| 2005/0113327 A1 | 5/2005 | Roiz et al. |
| 2005/0127306 A1 | 6/2005 | Yanagisawa et al. |
| 2005/0139787 A1 | 6/2005 | Chiba et al. |
| 2005/0161618 A1 | 7/2005 | Pedroni |
| 2005/0167616 A1 | 8/2005 | Yanagisawa et al. |
| 2005/0171396 A1* | 8/2005 | Pankratov ............ A61N 5/1049 600/1 |
| 2005/0184686 A1 | 8/2005 | Caporaso et al. |
| 2005/0186179 A1 | 8/2005 | Harats et al. |
| 2005/0205806 A1 | 9/2005 | Tadokoro et al. |
| 2005/0228255 A1 | 10/2005 | Saracen et al. |
| 2005/0234327 A1 | 10/2005 | Saracen et al. |
| 2005/0247890 A1 | 11/2005 | Norimine et al. |
| 2005/0259779 A1 | 11/2005 | Abraham-Fuchs et al. |
| 2005/0281374 A1 | 12/2005 | Cheng et al. |
| 2006/0017015 A1 | 1/2006 | Sliski et al. |
| 2006/0067468 A1 | 3/2006 | Rietzel |
| 2006/0126792 A1 | 6/2006 | Li |
| 2006/0127879 A1 | 6/2006 | Fuccione |
| 2006/0145088 A1 | 7/2006 | Ma |
| 2006/0175991 A1 | 8/2006 | Fujisawa |
| 2006/0192146 A1 | 8/2006 | Yanagisawa et al. |
| 2006/0204478 A1 | 9/2006 | Harats et al. |
| 2006/0219948 A1 | 10/2006 | Ueno et al. |
| 2006/0284562 A1 | 12/2006 | Hruby et al. |
| 2007/0001128 A1 | 1/2007 | Sliski et al. |
| 2007/0013273 A1 | 1/2007 | Albert et al. |
| 2007/0014654 A1 | 1/2007 | Haverfield et al. |
| 2007/0018120 A1 | 1/2007 | Beloussov et al. |
| 2007/0023699 A1 | 2/2007 | Yamashita et al. |
| 2007/0029510 A1 | 2/2007 | Hermann et al. |
| 2007/0031337 A1 | 2/2007 | Schulte |
| 2007/0034812 A1 | 2/2007 | Ma et al. |
| 2007/0051904 A1 | 3/2007 | Kaiser et al. |
| 2007/0053484 A1 | 3/2007 | Chiba et al. |
| 2007/0059387 A1 | 3/2007 | Stockfleth |
| 2007/0075273 A1 | 4/2007 | Birgy et al. |
| 2007/0083101 A1 | 4/2007 | Rietzel |
| 2007/0092812 A1 | 4/2007 | Caporaso et al. |
| 2007/0108922 A1 | 5/2007 | Amaldi |
| 2007/0114464 A1 | 5/2007 | Birgy et al. |
| 2007/0114471 A1 | 5/2007 | Birgy et al. |
| 2007/0114945 A1 | 5/2007 | Mattaboni et al. |
| 2007/0145916 A1 | 6/2007 | Caporaso et al. |
| 2007/0171015 A1 | 7/2007 | Antaya |
| 2007/0181519 A1 | 8/2007 | Khoshnevis |
| 2007/0217575 A1 | 9/2007 | Kaiser et al. |
| 2007/0262269 A1 | 11/2007 | Trbojevic |
| 2007/0284548 A1 | 12/2007 | Kaiser et al. |
| 2008/0023644 A1 | 1/2008 | Pedroni |
| 2008/0029706 A1 | 2/2008 | Kaiser et al. |
| 2008/0031414 A1 | 2/2008 | Coppens |
| 2008/0061241 A1 | 3/2008 | Rietzel |
| 2008/0073591 A1 | 3/2008 | Mohr |
| 2008/0078942 A1 | 4/2008 | Rietzel |
| 2008/0093567 A1 | 4/2008 | Gall |
| 2008/0123816 A1 | 5/2008 | Mori et al. |
| 2008/0131419 A1 | 6/2008 | Roiz et al. |
| 2008/0159478 A1 | 7/2008 | Keall et al. |
| 2008/0179544 A1 | 7/2008 | Kaiser et al. |
| 2008/0191142 A1 | 8/2008 | Pedroni |
| 2008/0191152 A1 | 8/2008 | Grozinger et al. |
| 2008/0205599 A1 | 8/2008 | Hashimoto |
| 2008/0218102 A1 | 9/2008 | Sliski et al. |
| 2008/0219407 A1 | 9/2008 | Kaiser et al. |
| 2008/0219410 A1 | 9/2008 | Gunzert-Marx et al. |
| 2008/0219411 A1 | 9/2008 | Gunzert-Marx et al. |
| 2008/0237494 A1 | 10/2008 | Beloussov et al. |
| 2008/0237495 A1 | 10/2008 | Grozinger et al. |
| 2008/0267349 A1 | 10/2008 | Rietzel |
| 2008/0270517 A1 | 10/2008 | Baumann et al. |
| 2008/0272284 A1 | 11/2008 | Rietzel |
| 2008/0290299 A1 | 11/2008 | Hansmann et al. |
| 2008/0298550 A1 | 12/2008 | Otto |
| 2008/0301872 A1 | 12/2008 | Fahrig et al. |
| 2008/0315111 A1 | 12/2008 | Sommer |
| 2009/0032742 A1 | 2/2009 | Kaiser et al. |
| 2009/0050819 A1 | 2/2009 | Ma et al. |
| 2009/0060130 A1 | 3/2009 | Wilkens et al. |
| 2009/0065717 A1 | 3/2009 | Kaiser et al. |
| 2009/0069640 A1 | 3/2009 | Rietzel et al. |
| 2009/0077209 A1 | 3/2009 | Schneider |
| 2009/0096179 A1 | 4/2009 | Stark et al. |
| 2009/0098145 A1 | 4/2009 | Mata et al. |
| 2009/0101833 A1 | 4/2009 | Emhofer et al. |
| 2009/0114847 A1 | 5/2009 | Grozinger et al. |
| 2009/0140671 A1 | 6/2009 | O'Neal, III et al. |
| 2009/0140672 A1 | 6/2009 | Gall et al. |
| 2009/0175414 A1 | 7/2009 | Messinger et al. |
| 2009/0189095 A1 | 7/2009 | Flynn et al. |
| 2009/0200483 A1 | 8/2009 | Gall et al. |
| 2009/0230327 A1 | 9/2009 | Rietzel |
| 2009/0234237 A1 | 9/2009 | Ross et al. |
| 2009/0261275 A1 | 10/2009 | Rietzel |
| 2009/0274269 A1 | 11/2009 | Foland et al. |
| 2009/0296885 A1 | 12/2009 | Boeh et al. |
| 2009/0309046 A1 | 12/2009 | Balakin |
| 2009/0309047 A1 | 12/2009 | Gunzert-Marx et al. |
| 2009/0309520 A1 | 12/2009 | Balakin |
| 2009/0314960 A1 | 12/2009 | Balakin |
| 2009/0314961 A1 | 12/2009 | Balakin |
| 2009/0321656 A1 | 12/2009 | Rietzel et al. |
| 2010/0006106 A1 | 1/2010 | Balakin |
| 2010/0006770 A1 | 1/2010 | Balakin |
| 2010/0008466 A1 | 1/2010 | Balakin |
| 2010/0014639 A1 | 1/2010 | Balakin |
| 2010/0014640 A1 | 1/2010 | Balakin |
| 2010/0020932 A1 | 1/2010 | Yi et al. |
| 2010/0027745 A1 | 2/2010 | Balakin |
| 2010/0038552 A1 | 2/2010 | Trbojevic |
| 2010/0045213 A1 | 2/2010 | Sliski et al. |
| 2010/0046697 A1 | 2/2010 | Balakin |
| 2010/0060209 A1 | 3/2010 | Balakin |
| 2010/0090122 A1 | 4/2010 | Balakin |
| 2010/0091948 A1 | 4/2010 | Balakin |
| 2010/0126964 A1 | 5/2010 | Smith et al. |
| 2010/0127184 A1 | 5/2010 | Balakin |
| 2010/0128846 A1 | 5/2010 | Balakin |
| 2010/0133444 A1 | 6/2010 | Balakin |
| 2010/0133446 A1 | 6/2010 | Balakin |
| 2010/0141183 A1 | 6/2010 | Balakin |
| 2010/0166150 A1 | 7/2010 | Perkins et al. |
| 2010/0171045 A1 | 7/2010 | Guneysel |
| 2010/0171447 A1 | 7/2010 | Balakin |
| 2010/0207552 A1 | 8/2010 | Balakin |
| 2010/0230617 A1 | 9/2010 | Gall |
| 2010/0230620 A1 | 9/2010 | Tsoupas et al. |
| 2010/0252754 A1 | 10/2010 | Brown et al. |
| 2010/0264327 A1 | 10/2010 | Bonig et al. |
| 2010/0266100 A1 | 10/2010 | Balakin |
| 2010/0288945 A1 | 11/2010 | Gnutzmann et al. |
| 2010/0296534 A1 | 11/2010 | Levecq et al. |
| 2010/0308235 A1 | 12/2010 | Sliski et al. |
| 2010/0320404 A1 | 12/2010 | Tanke |

(56) References Cited

U.S. PATENT DOCUMENTS

| | | |
|---|---|---|
| 2010/0327187 A1 | 12/2010 | Beloussov et al. |
| 2011/0006214 A1 | 1/2011 | Bonig |
| 2011/0009736 A1 | 1/2011 | Maltz et al. |
| 2011/0011729 A1 | 1/2011 | Poehlmann-Martins et al. |
| 2011/0027853 A1 | 2/2011 | Bert et al. |
| 2011/0047469 A1 | 2/2011 | Baumann et al. |
| 2011/0049396 A1 | 3/2011 | Furth et al. |
| 2011/0051891 A1 | 3/2011 | O'Connor et al. |
| 2011/0101236 A1 | 5/2011 | Cameron et al. |
| 2011/0118529 A1 | 5/2011 | Balakin |
| 2011/0118531 A1 | 5/2011 | Balakin |
| 2011/0124976 A1 | 5/2011 | Sabczynski et al. |
| 2011/0127443 A1 | 6/2011 | Comer et al. |
| 2011/0147608 A1 | 6/2011 | Balakin |
| 2011/0150180 A1 | 6/2011 | Balakin |
| 2011/0166219 A1 | 7/2011 | Stockfleth |
| 2011/0180720 A1 | 7/2011 | Balakin |
| 2011/0180731 A1 | 7/2011 | Welsh |
| 2011/0182410 A1 | 7/2011 | Balakin |
| 2011/0186720 A1 | 8/2011 | Jongen et al. |
| 2011/0196223 A1 | 8/2011 | Balakin |
| 2011/0214588 A1 | 9/2011 | Grubling et al. |
| 2011/0218430 A1 | 9/2011 | Balakin |
| 2011/0220794 A1 | 9/2011 | Censor et al. |
| 2011/0220798 A1 | 9/2011 | Baurichter et al. |
| 2011/0233423 A1 | 9/2011 | Balakin |
| 2011/0238440 A1 | 9/2011 | Leuschner |
| 2011/0248188 A1 | 10/2011 | Brusasco et al. |
| 2011/0278477 A1 | 11/2011 | Balakin |
| 2011/0284757 A1 | 11/2011 | Butuceanu et al. |
| 2011/0284760 A1 | 11/2011 | Balakin |
| 2011/0285327 A1 | 11/2011 | Begg et al. |
| 2011/0297850 A1 | 12/2011 | Claereboudt et al. |
| 2011/0299657 A1 | 12/2011 | Havelange et al. |
| 2011/0299919 A1 | 12/2011 | Stark et al. |
| 2011/0306870 A1 | 12/2011 | Kuhn |
| 2011/0313232 A1 | 12/2011 | Balakin |
| 2012/0001085 A1 | 1/2012 | Fujimoto et al. |
| 2012/0043481 A1 | 2/2012 | Mansfield et al. |
| 2012/0056099 A1 | 3/2012 | Behrens et al. |
| 2012/0056109 A1 | 3/2012 | Lomax |
| 2012/0069961 A1 | 3/2012 | Pomper et al. |
| 2012/0077748 A1 | 3/2012 | Vidyasagar et al. |
| 2012/0099704 A1 | 4/2012 | Ruan et al. |
| 2012/0112092 A1 | 5/2012 | Pomper et al. |
| 2012/0119114 A1 | 5/2012 | Brauer |
| 2012/0136194 A1 | 5/2012 | Zhang et al. |
| 2012/0143051 A1 | 6/2012 | Balakin |
| 2012/0205551 A1 | 8/2012 | Balakin |
| 2012/0207276 A1 | 8/2012 | Pomper et al. |
| 2012/0209109 A1 | 8/2012 | Balakin |
| 2012/0223246 A1 | 9/2012 | Stephani et al. |
| 2012/0224667 A1 | 9/2012 | Cheng et al. |
| 2012/0242257 A1 | 9/2012 | Balakin |
| 2012/0248325 A1 | 10/2012 | Balakin |
| 2012/0256103 A1 | 10/2012 | Luzzara |
| 2012/0264998 A1 | 10/2012 | Fujitaka et al. |
| 2012/0267543 A1 | 10/2012 | Noda et al. |
| 2012/0273666 A1 | 11/2012 | Bert et al. |
| 2012/0280150 A1 | 11/2012 | Jongen |
| 2012/0303384 A1 | 11/2012 | Stepaniak et al. |
| 2012/0313003 A1 | 12/2012 | Trbojevic |
| 2012/0323516 A1 | 12/2012 | Rigney et al. |
| 2012/0326722 A1 | 12/2012 | Weinberg et al. |
| 2013/0001432 A1 | 1/2013 | Jongen |
| 2013/0043403 A1 | 2/2013 | Gordon et al. |
| 2013/0053616 A1 | 2/2013 | Gall et al. |
| 2013/0053617 A1 | 2/2013 | Pu et al. |
| 2013/0068938 A1 | 3/2013 | Heese |
| 2013/0072743 A1 | 3/2013 | Fieres et al. |
| 2013/0072744 A1 | 3/2013 | Moskvin et al. |
| 2013/0075622 A1 | 3/2013 | Katayose |
| 2013/0086500 A1 | 4/2013 | Kane et al. |
| 2013/0090549 A1 | 4/2013 | Meltsner et al. |
| 2013/0108014 A1 | 5/2013 | Tome et al. |
| 2013/0127375 A1 | 5/2013 | Sliski et al. |
| 2013/0131424 A1 | 5/2013 | Sliski et al. |
| 2013/0131433 A1 | 5/2013 | Katscher et al. |
| 2013/0150647 A1 | 6/2013 | Chen et al. |
| 2013/0163723 A1 | 6/2013 | Tacke |
| 2013/0187060 A1 | 7/2013 | Jongen |
| 2013/0208867 A1 | 8/2013 | Beckman |
| 2013/0209450 A1 | 8/2013 | Cohen et al. |
| 2013/0211482 A1 | 8/2013 | Piipponen |
| 2013/0217946 A1 | 8/2013 | Balakin |
| 2013/0217948 A1 | 8/2013 | Mihaylov |
| 2013/0217950 A1 | 8/2013 | Partanen et al. |
| 2013/0218009 A1 | 8/2013 | Balakin |
| 2013/0221213 A1 | 8/2013 | Takayanagi et al. |
| 2013/0237425 A1 | 9/2013 | Leigh et al. |
| 2013/0237822 A1 | 9/2013 | Gross et al. |
| 2013/0243722 A1 | 9/2013 | Basile et al. |
| 2013/0245113 A1 | 9/2013 | Stockfleth |
| 2013/0259335 A1 | 10/2013 | Mallya et al. |
| 2013/0267756 A1 | 10/2013 | Totake et al. |
| 2013/0277569 A1 | 10/2013 | Behrens et al. |
| 2013/0303824 A1 | 11/2013 | Stephani et al. |
| 2013/0324479 A1 | 12/2013 | Zhang et al. |
| 2013/0345489 A1 | 12/2013 | Beloussov et al. |
| 2014/0005463 A1 | 1/2014 | Jongen |
| 2014/0005464 A1 | 1/2014 | Bharat et al. |
| 2014/0014851 A1 | 1/2014 | Asaba |
| 2014/0028220 A1 | 1/2014 | Bromberg et al. |
| 2014/0042934 A1 | 2/2014 | Tsutsui |
| 2014/0046113 A1 | 2/2014 | Fujimoto et al. |
| 2014/0061493 A1 | 3/2014 | Prieels et al. |
| 2014/0066755 A1 | 3/2014 | Matteo et al. |
| 2014/0077699 A1 | 3/2014 | Boswell et al. |
| 2014/0091734 A1 | 4/2014 | Gall et al. |
| 2014/0094371 A1 | 4/2014 | Zwart et al. |
| 2014/0094637 A1 | 4/2014 | Zwart et al. |
| 2014/0094638 A1 | 4/2014 | Gall et al. |
| 2014/0094639 A1 | 4/2014 | Zwart et al. |
| 2014/0094640 A1 | 4/2014 | Gall et al. |
| 2014/0094641 A1 | 4/2014 | Gall et al. |
| 2014/0094643 A1 | 4/2014 | Gall et al. |
| 2014/0097920 A1 | 4/2014 | Goldie et al. |
| 2014/0107390 A1 | 4/2014 | Brown et al. |
| 2014/0112453 A1 | 4/2014 | Prince et al. |
| 2014/0113388 A1 | 4/2014 | Bitter et al. |
| 2014/0121441 A1 | 5/2014 | Huber et al. |
| 2014/0128719 A1 | 5/2014 | Longfield |
| 2014/0145090 A9 | 5/2014 | Jongen |
| 2014/0193058 A1 | 7/2014 | Bharat et al. |
| 2014/0200448 A1 | 7/2014 | Schulte et al. |
| 2014/0221816 A1 | 8/2014 | Franke et al. |
| 2014/0257011 A1 | 9/2014 | Spotts |
| 2014/0257099 A1 | 9/2014 | Balakin |
| 2014/0275699 A1 | 9/2014 | Benna et al. |
| 2014/0308202 A1 | 10/2014 | Matusik et al. |
| 2014/0316184 A1 | 10/2014 | Fujimoto et al. |
| 2014/0330063 A1 | 11/2014 | Balakin |
| 2014/0332691 A1 | 11/2014 | Campbell et al. |
| 2014/0336438 A1 | 11/2014 | Bharat et al. |
| 2014/0350322 A1 | 11/2014 | Schulte et al. |
| 2014/0369958 A1 | 12/2014 | Basile |
| 2014/0371076 A1 | 12/2014 | Jongen |
| 2014/0371511 A1 | 12/2014 | Zwart et al. |
| 2015/0015167 A1 | 1/2015 | Ungaro et al. |
| 2015/0030223 A1 | 1/2015 | Pearlstein et al. |
| 2015/0041665 A1 | 2/2015 | Hollebeek et al. |
| 2015/0076370 A1 | 3/2015 | Totake et al. |
| 2015/0080633 A1 | 3/2015 | Anferov |
| 2015/0080634 A1 | 3/2015 | Huber et al. |
| 2015/0087883 A1 | 3/2015 | Boudreau et al. |
| 2015/0087885 A1 | 3/2015 | Boisseau et al. |
| 2015/0087887 A1 | 3/2015 | Iwata |
| 2015/0087960 A1 | 3/2015 | Treffert |
| 2015/0090894 A1 | 4/2015 | Zwart et al. |
| 2015/0099917 A1 | 4/2015 | Bula et al. |
| 2015/0126797 A1 | 5/2015 | Aptaker et al. |
| 2015/0146856 A1 | 5/2015 | Beckman |
| 2015/0148584 A1 | 5/2015 | Gall et al. |
| 2015/0174429 A1 | 6/2015 | Zwart et al. |

(56) References Cited

U.S. PATENT DOCUMENTS

| | | |
|---|---|---|
| 2015/0196534 A1 | 7/2015 | Vidyasagar et al. |
| 2015/0196779 A1 | 7/2015 | Tonner |
| 2015/0209601 A1 | 7/2015 | Benna et al. |
| 2015/0217138 A1 | 8/2015 | Fujimoto et al. |
| 2015/0217140 A1 | 8/2015 | Balakin |
| 2015/0231411 A1 | 8/2015 | O'Neal, III et al. |
| 2015/0273239 A1 | 10/2015 | Hsu et al. |
| 2015/0321025 A1 | 11/2015 | Freud et al. |
| 2015/0328483 A1 | 11/2015 | Odawara et al. |
| 2015/0335463 A1 | 11/2015 | De Gruytere |
| 2015/0335919 A1 | 11/2015 | Behar et al. |
| 2015/0337393 A1 | 11/2015 | Keller et al. |
| 2015/0343238 A1 | 12/2015 | Balakin |
| 2015/0352372 A1 | 12/2015 | Takayanagi et al. |
| 2015/0352374 A1 | 12/2015 | Gattiker et al. |
| 2015/0374324 A1 | 12/2015 | Nishimura et al. |
| 2016/0000387 A1 | 1/2016 | Buchsbaum et al. |
| 2016/0008631 A1 | 1/2016 | Harada et al. |
| 2016/0016010 A1 | 1/2016 | Schulte et al. |
| 2016/0048981 A1 | 2/2016 | Pearlstein et al. |
| 2016/0059039 A1 | 3/2016 | Liu |
| 2016/0067316 A1 | 3/2016 | Sunavala-Dossabhoy |
| 2016/0067525 A1 | 3/2016 | Bouchet et al. |
| 2016/0071623 A1 | 3/2016 | Schewiola et al. |
| 2016/0074675 A1 | 3/2016 | Moskvin et al. |
| 2016/0113884 A1 | 4/2016 | Lin et al. |
| 2016/0136457 A1 | 5/2016 | Jung et al. |
| 2016/0144201 A1 | 5/2016 | Schulte |
| 2016/0172066 A1 | 6/2016 | Claereboudt |
| 2016/0172067 A1 | 6/2016 | Claereboudt et al. |
| 2016/0175052 A1 | 6/2016 | Kumar et al. |
| 2016/0175617 A1 | 6/2016 | Spatola et al. |
| 2016/0199667 A1 | 7/2016 | Flynn et al. |
| 2016/0199671 A1 | 7/2016 | Jongen |
| 2016/0220846 A1 | 8/2016 | Matteo et al. |
| 2016/0220847 A1 | 8/2016 | Benna et al. |
| 2016/0243232 A1 | 8/2016 | Pickett |
| 2016/0250501 A1 | 9/2016 | Balakin |
| 2016/0250503 A1 | 9/2016 | Balakin et al. |
| 2016/0256712 A1 | 9/2016 | Vahala et al. |
| 2016/0263404 A1 | 9/2016 | Mougenot |
| 2016/0270203 A1 | 9/2016 | Ungaro et al. |
| 2016/0271424 A1 | 9/2016 | Lee et al. |
| 2016/0287899 A1 | 10/2016 | Park et al. |
| 2016/0296766 A1 | 10/2016 | El Fakhri et al. |
| 2016/0303399 A1 | 10/2016 | Balakin |
| 2016/0331999 A1 | 11/2016 | Hartman et al. |
| 2017/0036040 A1 | 2/2017 | Bergfjord et al. |

FOREIGN PATENT DOCUMENTS

| | | | |
|---|---|---|---|
| CN | 1537657 | A | 10/2004 |
| CN | 1540676 | A | 10/2004 |
| CN | 1816243 | A | 8/2006 |
| CN | 101061759 | A | 10/2007 |
| CN | 101932361 | A | 12/2010 |
| CN | 101933405 | A | 12/2010 |
| CN | 101933406 | A | 12/2010 |
| CN | 104812443 | A | 7/2015 |
| CN | 105561484 | A | 5/2016 |
| DE | 2753397 | A1 | 6/1978 |
| DE | 3148100 | A1 | 6/1983 |
| DE | 3530446 | A1 | 3/1986 |
| DE | 3711245 | A1 | 10/1988 |
| DE | 4101094 | C1 | 5/1992 |
| DE | 4411171 | A1 | 10/1995 |
| DE | 102011089235 | A1 | 8/2012 |
| EP | 0194728 | A1 | 9/1986 |
| EP | 0208163 | A1 | 1/1987 |
| EP | 0221987 | A1 | 5/1987 |
| EP | 0222786 | A1 | 5/1987 |
| EP | 0277521 | A2 | 8/1988 |
| EP | 0306966 | A2 | 3/1989 |
| EP | 0388123 | A2 | 9/1990 |
| EP | 0465597 | A1 | 1/1992 |
| EP | 0499253 | A2 | 8/1992 |
| EP | 0751532 | A1 | 1/1997 |
| EP | 0776595 | A1 | 6/1997 |
| EP | 0864337 | A2 | 9/1998 |
| EP | 0911064 | A2 | 4/1999 |
| EP | 1069809 | A1 | 1/2001 |
| EP | 1153398 | A1 | 11/2001 |
| EP | 1294445 | A2 | 3/2003 |
| EP | 1348465 | A1 | 10/2003 |
| EP | 1358908 | A1 | 11/2003 |
| EP | 1371390 | A1 | 12/2003 |
| EP | 1402923 | A1 | 3/2004 |
| EP | 1430932 | A1 | 6/2004 |
| EP | 1454653 | A1 | 9/2004 |
| EP | 1454654 | A2 | 9/2004 |
| EP | 1454655 | A2 | 9/2004 |
| EP | 1454656 | A2 | 9/2004 |
| EP | 1454657 | A2 | 9/2004 |
| EP | 1477206 | A1 | 11/2004 |
| EP | 1541194 | A1 | 6/2005 |
| EP | 1605742 | A1 | 12/2005 |
| EP | 1738798 | A2 | 1/2007 |
| EP | 1826778 | A2 | 8/2007 |
| EP | 1949404 | A2 | 7/2008 |
| EP | 2114529 | B1 | 11/2009 |
| EP | 2183753 | A1 | 5/2010 |
| EP | 2227295 | A1 | 9/2010 |
| EP | 2232961 | A1 | 9/2010 |
| EP | 2232962 | A2 | 9/2010 |
| EP | 2363170 | A1 | 9/2011 |
| EP | 2363171 | A1 | 9/2011 |
| EP | 2394498 | A2 | 12/2011 |
| EP | 2514482 | A1 | 10/2012 |
| EP | 2524718 | A1 | 11/2012 |
| EP | 2572756 | A1 | 3/2013 |
| EP | 3088048 | A1 | 11/2016 |
| FR | 2560421 | A1 | 8/1985 |
| FR | 2911843 | A1 | 8/2008 |
| GB | 0957342 | A | 5/1964 |
| GB | 2015821 | A | 9/1979 |
| GB | 2361523 | A | 10/2001 |
| JP | S47-028762 | U | 12/1972 |
| JP | U48/108098 | | 9/1973 |
| JP | 57-162527 | | 10/1982 |
| JP | 58-141000 | | 8/1983 |
| JP | 61-225798 | | 10/1986 |
| JP | 62-150804 | | 7/1987 |
| JP | 62-186500 | | 8/1987 |
| JP | 63-149344 | | 6/1988 |
| JP | 63-218200 | | 9/1988 |
| JP | 63-226899 | | 9/1988 |
| JP | 64-89621 | | 4/1989 |
| JP | 01-276797 | | 11/1989 |
| JP | 01-302700 | | 12/1989 |
| JP | 4-94198 | | 3/1992 |
| JP | 06-036893 | | 8/1994 |
| JP | 06-233831 | | 8/1994 |
| JP | 07-260939 | | 10/1995 |
| JP | 07-263196 | | 10/1995 |
| JP | 08-173890 | | 7/1996 |
| JP | 08-264298 | | 10/1996 |
| JP | 09-162585 | | 6/1997 |
| JP | 10-071213 | | 3/1998 |
| JP | 11-47287 | | 2/1999 |
| JP | H1128252 | A | 2/1999 |
| JP | 11-102800 | | 4/1999 |
| JP | 11-243295 | | 9/1999 |
| JP | 2000-243309 | A | 9/2000 |
| JP | 2000-294399 | A | 10/2000 |
| JP | 2001-6900 | | 1/2001 |
| JP | 2001-009050 | A | 1/2001 |
| JP | 2001-129103 | A | 5/2001 |
| JP | 2001-346893 | A | 12/2001 |
| JP | 2002-113118 | A | 4/2002 |
| JP | 2002-164686 | A | 6/2002 |
| JP | 2003-504628 | A | 2/2003 |
| JP | 2003-517755 | A | 5/2003 |
| JP | 2004-031115 | A | 1/2004 |
| JP | 2004-321408 | A | 11/2004 |

(56) References Cited

FOREIGN PATENT DOCUMENTS

| | | |
|---|---|---|
| JP | 2005-526578 A | 9/2005 |
| JP | 2006-032282 A | 2/2006 |
| JP | 2007-502166 A | 2/2007 |
| JP | 2008-507826 A | 3/2008 |
| JP | 04-128717 B2 | 7/2008 |
| JP | 04-129768 B2 | 8/2008 |
| JP | 61-80800 | 1/2009 |
| JP | 2009-515671 A | 4/2009 |
| JP | 2009-515671 A | 4/2009 |
| JP | 2009-516905 A | 4/2009 |
| JP | 04-273409 B2 | 6/2009 |
| JP | 04-337300 B2 | 9/2009 |
| JP | 43-23267 B2 | 9/2009 |
| JP | 2010-536130 A | 11/2010 |
| JP | 2011-505191 A | 2/2011 |
| JP | 2011-505670 A | 2/2011 |
| JP | 2011-507151 A | 3/2011 |
| JP | 05-046928 B2 | 10/2012 |
| JP | 05-341352 B2 | 11/2013 |
| JP | 2015-530194 A | 10/2015 |
| JP | 2016-055161 A | 4/2016 |
| JP | 2016-55161 A | 4/2016 |
| SU | 300137 | 6/1969 |
| SU | 569635 A1 | 8/1977 |
| TW | 200930160 A | 7/2009 |
| TW | 200934682 A | 8/2009 |
| TW | 200939908 A | 9/2009 |
| TW | 200940120 A | 10/2009 |
| WO | WO-1986/07229 A1 | 12/1986 |
| WO | WO-1990/012413 A1 | 10/1990 |
| WO | WO-1992/03028 A1 | 2/1992 |
| WO | WO-1993/02536 A1 | 2/1993 |
| WO | WO-1998/17342 A2 | 4/1998 |
| WO | WO-1999/39385 A1 | 8/1999 |
| WO | WO-2000/40064 A2 | 7/2000 |
| WO | WO-2000/49624 A1 | 8/2000 |
| WO | WO-01/126569 | 4/2001 |
| WO | WO-2001/026230 A1 | 4/2001 |
| WO | WO-02/07817 | 1/2002 |
| WO | WO-2003/039212 A1 | 5/2003 |
| WO | WO-2003/092812 A1 | 11/2003 |
| WO | WO-2004/026401 A1 | 4/2004 |
| WO | WO-2004/101070 A1 | 11/2004 |
| WO | 2005018734 A1 | 3/2005 |
| WO | WO-2006-012467 A2 | 2/2006 |
| WO | 2007061937 A2 | 5/2007 |
| WO | WO-2007/061937 A2 | 5/2007 |
| WO | WO-2007/084701 A1 | 7/2007 |
| WO | WO-2007/130164 A2 | 11/2007 |
| WO | WO-2007/145906 A2 | 12/2007 |
| WO | WO-2008/030911 A2 | 3/2008 |
| WO | WO-2008/081480 A1 | 7/2008 |
| WO | WO-2009/048745 A2 | 4/2009 |
| WO | WO-2009/070173 A1 | 6/2009 |
| WO | WO-2009/070588 A1 | 6/2009 |
| WO | WO-2009/073480 A2 | 6/2009 |
| WO | 2012023205 A1 | 2/2012 |
| WO | 2012152938 A2 | 11/2012 |
| WO | WO-2014/018706 A1 | 1/2014 |
| WO | WO-2014/018876 A1 | 1/2014 |
| WO | 2014052734 A1 | 4/2014 |
| WO | 2014154740 A1 | 10/2014 |
| WO | WO-2014/154740 A1 | 10/2014 |
| WO | WO-2015/003111 A1 | 1/2015 |
| WO | WO-2015/095678 A2 | 6/2015 |
| WO | WO-2015/107660 A1 | 7/2015 |
| WO | WO-2018/156446 A1 | 8/2018 |

OTHER PUBLICATIONS

510(k) Summary: Ion Beam Applications S.A., FDA, Jul. 12, 2001, 5 pages.

510(k) Summary: Optivus Proton Beam Therapy System, Jul. 21, 2000, 5 pages.

Abrosimov et al., 1000MeV Proton Beam Therapy facility at Petersburg Nuclear Physics Institute Synchrocyclotron, Medical Radiology (Moscow) 32, 10 (1987) revised in Journal of Physics, Conference Series 41, 2006, pp. 424-432, Institute of Physics Publishing Limited.

Abrosimov et al., Neutron Time-of-flight Spectrometer Gneis at the Gatchina 1 GeV Protron Syncrhocyclotron, Mar. 9, 1985 and revised form Jul. 31, 1985, Lemingrad Nuclear Physics Institute, Gatchina, 188350, USSR (15 pages).

Adachi et al., A 150MeV FFAG Synchrotron with Return-Yoke Free Magent, Proceedings of the 2001 Particle Accelerator Conference, Chicago, 2001, 3 pages.

Ageyev et al., The IHEP Accelerating and Storage Complex (UNK) Status Report, 11th International Conference on High-Energy Accelerators, 1980, pp. 60-70.

Agosteo et al., Maze Design of a gantry room for proton therapy, Nuclear Instruments & Methods in Physics Research, 1996, Section A, 382, pp. 573-582.

Alexeev et al., R4 Design of Superconducting Magents for Proton Synchrotrons, Proceedings of the Fifth International Cryogenic Engineering Conference, 197 4, pp. 531-533.

Allardyce et al., Performance and Prospects of the Reconstructed CERN 600 MeV Synchrocyclotron, IEEE Transactions on Nuclear Science USA, Jun. 1977, ns-24:(3) 1631-1633.

Alonso, Magnetically Scanned Ion Beams for Radiation Therapy, Accelerator & Fusion Research Division, Lawrence Berkeley Laboratory, Berkeley, CA, Oct. 1988, 13 pages.

Amaldi et al., The Italian project for a hadrontherapy centre Nuclear Instruments and Methods in Physics Research A, 1995, 360, pp. 297-301.

Amaldi, Overview of the world landscape of Hadrontherapy and the projects of the TERA foundation, Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.

An Accelerated Collaboration Meets with Beaming Success, Lawrence Livermore National Laboratory, Apr. 12, 2006, S&TR, Livermore, California, pp. 1-3, http://www.llnl.gov/str/April06/Caporaso.html.

Anferov et al., Status of the Midwest Proton Radiotherapy Institute, Proceedings of the 2003 Particle Accelerator Conference, 2003, pp. 699-701.

Anferov et al., The Indiana University Midwest Proton Radiation Institute, Proceedings of the 2001 Particle Accelerator Conference, 2001, Chicago, pp. 645-647.

Appun, Various problems of magnet fabrication for high-energy accelerators, Journal for All Engineers Interested in the Nuclear Field, 1967, 11 pp. 10-16 (1967) [Lang.: German], English bibliographic information (httn://www.osti.1mv/enernvcitations/nroduct.biblio.isn?osti id=4442292).

Arduini et al. Physical specifications of clinical proton beams from a synchrotron, Med. Phys, Jun. 1996, 23 ( 6): 939-951.

Badano et al., Proton-Ion Medical Machine Study (PIMMS) Part I, Pimms, Jan. 1999, 238 pages.

Beam Delivery and Properties, Journal of the ICRU, 2007, 7(2):20 pages.

Beeckman et al., Preliminary design of a reduced cost proton therapy facility using a compact, high field isochronous cyclotron, Nuclear Instruments and Methods in Physics Research B56/57, 1991, pp. 1201-1204.

Bellomo et al., The Superconducting Cyclotron Program at Michigan State University, Bulletin of the American Physical Society, Sep. 1980, 25(7):767.

Benedikt and Carli, Matching to Gantries for Medical Synchrotrons IEEE Proceedings of the 1997 Particle Accelerator Conference, 1997, pp. 13 79-13 81.

Bieth et al., A Very Compact Protontherapy Facility Based on an Extensive Use of High Temperature Superconductors (HTS) Cyclotrons and their Applications 1998, Proceedings of the Fifteenth International Conference on Cyclotrons and their Applications, Caen, Jun. 14-19, 1998, pp. 669-672.

(56) References Cited

OTHER PUBLICATIONS

Bigham, Magnetic Trim Rods for Superconducting Cyclotrons, Nuclear Instruments and Methods (North-Holland Publishing Co.), 1975, 141:223-228.
Bimbot, First Studies of the External Beam from the Orsay S.C. 200 MeV, Institut de Physique Nucleaire, BP 1, Orsay, France, IEEE, 1979, pp. 1923-1926.
Blackmore et al., Operation of the Triumf Proton Therapy Facility, IEEE Proceedings of the 1997 Particle Accelerator Conference, May 12-16, 1997, 3:3831-3833.
Bloch, The Midwest Proton Therapy Center, Application of Accelerators in Research and Industry, Proceedings of the Fourteenth Int'l. Conf, Part Two, Nov. 1996, pp. 1253-1255.
Blosser et al., A Compact Superconducting Cyclotron for the Production of High Intensity Protons, Proceedings of the 1997 Particle Accelerator Conference, May 12-16, 1997, 1:1054-1056.
Blosser et al., Advances in Superconducting Cyclotrons at Michigan State University, Proceedings of the 11th International Conference on Cyclotrons and their Applications, Oct. 1986, pp. 157-167, Tokyo.
Blosser et al., Characteristics of a 400 (Q2/A) MeV Super-Conducting Heavy-Ion Cyclotron, Bulletin of the American Physical Society, Oct. 1974, p. 1026.
Blosser et al., Medical Accelerator Projects at Michigan State Univ. IEEE Proceedings of the 1989 Particle Accelerator Conference, Mar. 20-23, 1989, 2:742-746.
Blosser et al., Problems and Accomplishments of Superconducting Cyclotrons, Proceedings of the 14th International Conference, Cyclotrons and Their Applications, Oct. 1995, pp. 674-684.
Blosser et al., Progress toward an experiment to study the effect of RF grounding in an internal ion source on axial oscillations of the beam in a cyclotron, National Superconducting Cyclotron Laboratory, Michigan State University, Report MSUCL-760, CP600, Cyclotrons and their Applications 2011, Sixteenth International Conference, 2001, pp. 274-276.
Blosser et al., Superconducting Cyclotron for Medical Application, IEEE Transactions on Magnetics, Mar. 1989, 25(2): 1746-1754.
Blosser et al., Superconducting Cyclotrons, Seventh International Conference on Cyclotrons and their Applications, Aug. 19-22, 1975, pp. 584-594.
Blosser, Application of Superconductivity in Cyclotron Construction, Ninth International Conference on Cyclotrons and their Applications, Sep. 1981, pp. 147-157.
Blosser, Applications of Superconducting Cyclotrons, Twelfth International Conference on Cyclotrons and Their Applications, May 8-12, 1989, pp. 137-144.
Blosser, Future Cyclotrons, AIP, The Sixth International Cyclotron Conference, 1972, pp. 16-32.
Blosser, H., Present and Future Superconducting Cyclotrons, Bulletin of the American Physical Society, Feb. 1987, 32(2):171 Particle Accelerator Conference, Washington, D.C.
Blosser, H.G., Superconducting Cyclotrons at Michigan State University, Nuclear Instruments & Methods in Physics Research, 1987,vol. B 24/25, part II, pp. 752-756.
Blosser, Medical Cyclotrons, Physics Today, Special Issue Physical Review Centenary, Oct. 1993, pp. 70-73.
Blosser, Preliminary Design Study Exploring Building Features Required for a Proton Therapy Facility for the Ontario Cancer Institute, Mar. 1991, MSUCL-760a, 53 pages.
Blosser, Synchrocyclotron Improvement Programs, IEEE Transactions on Nuclear Science USA, Jun. 1969, 16(3):Part I, pp. 405-414.
Blosser, The Michigan State University Superconducting Cyclotron Program, Nuclear Science, Apr. 1979, NS-26(2):2040-2047.
Botha et al., A New Multidisciplinary Separated-Sector Cyclotron Facility, IEEE Transactions on Nuclear Science, 1977, NS-24(3): 1118-1120.
Boyer, A. et al., Basic Applications of Multileaf Collimators: Report of Task Group No. 50-Radiation Therapy Committee, AAPM Report No. 72, American Association of Physicists in Medicine by Medical Physics Publishing, 62 pages (2001).
Bues, M. et al., Therapeutic Step and Shoot Proton Beam Spot-Scanning With a Multi-Leaf Collimator: A Monte Carlo Study, Radiation Protection Dosimetry, 115(1-4):164-169 (2005).
Chichili et al., Fabrication of Nb3Sn Shell-Type Coils with Pre-Preg Ceramic Insulation, American Institute of Physics Conference Proceedings, AIP USA, No. 711, (XP-002436709, ISSN: 0094-243X), 2004, pp. 450-457.
Chong et al., Radiology Clinic North American 7, 3319, 1969, 27 pages.
Chu et al., Instrumentation for Treatment of Cancer Using Proton and Light-ion Beams, Review of Scientific Instruments, Aug. 1993, 64 (8):2055-2122.
Chu et al., Performance Specifications for Proton Medical Facility, Lawrence Berkeley Laboratory, University of California, Mar. 1993, 128 pages.
Chu, Instrumentation in Medical Systems, Accelerator and Fusion Research Division, Lawrence Berkeley Laboratory, University of California, Berkeley, CA, May 1995, 9 pages.
Cole et al., Design and Application of a Proton Therapy Accelerator, Fermi National Accelerator Laboratory, IEEE, 1985, 5 pages.
Collins, et al., The Indiana University Proton Therapy System, Proceedings of EPAC 2006, Edinburgh, Scotland, 2006, 3 pages.
Communication pursuant to Rules 161(1) and 162 EPC in EP14830919.8, 2 pages (Sep. 2, 2016).
Conradi et al., Proposed New Facilities for Proton Therapy at iThemba Labs, Proceedings of EPAC, 2002, pp. 560-562.
C/E Source of Ions for Use in Sychro-Cyclotrons Search, Jan. 31, 2005, 9 pages.
Source Search Cites of U.S. and Foreign Patents/Published applications in the name of Mitsubishi Denki Kabushiki Kaisha and Containing the Keywords (Proton and Synchrocyclotron), Jan. 2005, 8 pages.
Cosgrove et al., Microdosimetric Studies on the Orsay Proton Synchrocyclotron at 73 and 200 MeV, Radiation Protection Dosimetry, 1997, 70(1-4):493-496.
Coupland, High-field (5 T) pulsed superconducting dipole magnet, Proceedings of the Institution of Electrical Engineers, Jul. 1974, 121(7):771-778.
Coutrakon et al. Proton Synchrotrons for Cancer Therapy, Application of Accelerators in Research and Industry- Sixteenth International Conf., American Institute of Physics, Nov. 1-5, 2000, vol. 576, pp. 861-864.
Coutrakon et al., A prototype beam delivery system for the proton medical accelerator at Loma Linda, Medical Physics, Nov./Dec. 1991, 18(6):1093-1099.
CPAC Highlights Its Proton Therapy Program at ESTRO Annual Meeting, TomoTherapy Incorporated, Sep. 18, 2008, Madison, Wisconsin, pp. 1-2.
Cuttone, Applications of a Particle Accelerators in Medical Physics, Istituto Nazionale di Fisica Nucleare-Laboratori Nazionali del Sud, V.S. Sofia, 44 Cantania, Italy, Jan. 2010, 17 pages.
Daartz, J. et al., Characterization of a mini-multileaf collimator in a proton beamline, Med. Phys., 36(5):9 pages (2009).
Dahl P, Superconducting Magnet System, American Institute of Physics, AIP Conference Proceedings, 1987-1988, 2: 1329-1376.
Dialog Search, Jan. 31, 2005, 17 pages.
Dugan et al., Tevatron Status IEEE, Particle Accelerator Conference, Accelerator Science & Technology, 1989, pp. 426-430.
Eickhoff et al., The Proposed Accelerator Facility for Light Ion Cancer Therapy in Heidelberg, Proceedings of the 1999 Particle Accelerator Conference, New York, 1999, pp. 2513-2515.
Enchevich et al., Minimizing Phase Losses in the 680 MeV Synchrocyclotron by Correcting the Accelerating Voltage Amplitude, Atomnaya Energiya, 1969, 26:(3):315-316.
Endo et al., Compact Proton and Carbon Ion Synchrotrons for Radiation Therapy, Proceedings of EPAC 2002, Paris France, 2002, pp. 2733-2735.
File History of U.S. Appl. No. 13/303,110.
File History of U.S. Appl. No. 61/843,092, 84 pages. (downloaded Oct. 14, 2016).
File History of U.S. Appl. No. 61/900,455, 43 pages (downloaded Oct. 14, 2016).

(56) References Cited

OTHER PUBLICATIONS

File History of U.S. Appl. No. 61/946,074, 137 pages (downloaded Oct. 14, 2016).
Final Office Action for U.S. Appl. No. 14/137,854, 29 pages (dated Sep. 19, 2016).
Flanz et al., Large Medical Gantries, Particle Accelerator Conference, Massachusetts General Hospital, 1995, pp. 1-5.
Flanz et al., Operation of a Cyclotron Based Proton Therapy Facility, Massachusetts General Hospital, Boston, MA 02114, pp. 1-4, retrieved from Internet in 2009.
Flanz et al., The Northeast Proton Therapy Center at Massachusetts General Hospital, Fifth Workshop on Heavy Charge Particles in Biology and Medicine, GSI, Darmstadt, Aug. 1995, 11 pages.
Flanz et al., Treating Patients with the NPTC Accelerator Based Proton Treatment Facility, Proceedings of the 2003 Particle Accelerator Conference, 2003, pp. 690-693.
Flood and Frazier, The Wide-Band Driven RF System for the Berkeley 88-Inch Cyclotron, American Institute of Physics, Conference Proceedings., No. 9, 1972, 459-466.
Foster and Kashikhin, Superconducting Superferric Dipole Magent with Cold Iron Core for the VLHC, IEEE Transactions on Applied Superconductivity, Mar. 2002, 12(1):111-115.
Fredriksson, Albin, Robust optimization of radiation therapy accounting for geometric uncertainty, Doctoral Thesis, 57 pages (2013).
Friesel et al., Design and Construction Progress on the IUCF Midwest Proton Radiation Institute, Proceedings of EPAC 2002, 2002, pp. 2736-2738.
Fukumoto et al., A Proton Therapy Facility Plan Cyclotrons and their Applications, Proceedings of the 13th International Conference, Vancouver, Canada, Jul. 6-10, 1992, pp. 258-261.
Fukumoto, Cyclotron Versus Synchrotron for Proton Beam Therapy, KEK Prepr., No. 95-122, Oct. 1995, pp. 533-536.
Gelover, E. et al., A method for modeling laterally asymmetric proton beamlets resulting from collimation, Medical Physics, 42:1321-1334 (2015).
Goto et al., Progress on the Sector Magnets for the Riken SRC, American Institute of Physics, 714 CP600, Cyclotrons and Their Applications 2001, Sixteenth International Conference, 2001, pp. 319-323.
Graffman et al., Design Studies for a 200 MeV Proton Clinic for Radiotherapy, AIP Conference Proceedings: Cyclotrons—1972, 1972, No. 9, pp. 603-615.
Graffman, et. al. Proton radiotherapy with the Uppsala cyclotron. Experience and plans Strahlentherapie, 1985, 161(12):764-770.
Graffman, S., et al., Clinical Trials in Radiotherapy and the Merits of High Energy Protons, Acta Radiol. Therapy Phys. Biol. 9:1-23 (1970).
Hede, Research Groups Promoting Proton Therapy Lite, Journal of the National Cancer Institute, Dec. 6, 2006, 98(23):1682-1684.
Heinz, Superconducting Pulsed Magnetic Systems for High-Energy Synchrotrons, Proceedings of the Fourth International Cryogenic Engineering Conference, May 24-26, 1972, pp. 55-63.
Hentschel et al., Plans for the German National Neutron Therapy Centre with a Hospital-Based 70 MeV Proton Cyclotron at University Hospital Essen/Germany, Cyclotrons and their Applications, Proceedings of the Fifteenth International Conference on Cyclotrons and their Applications, Caen, Franco, Jun. 14-19, 1998, pp. 21-23.
Hepburn et al., Superconducting Cyclotron Neutron Source for Therapy, International Journal of Radiation Oncology Biology Physics, vol. 3 complete, 1977, pp. 387-391.
Hirabayashi, Development of Superconducting Magnets for Beam Lines and Accelerator at KEK, IEEE Transaction on Magnetics, Jan. 1981, MAG-17(1):728-731.
Hyer, D. et al., A dynamic collimation system for penumbra reduction in spot-scanning proton therapy: Proof of concept, American Association of Physicists in Medicine, 10 pages (2014).
Hyer, D. et al., A dynamic collimation system for penumbra reduction in spot-scanning proton therapy: Proof of concept; Medical Physics, 41(9):091701-1-091701-9 (2014).
Indiana's mega-million proton therapy cancer center welcomes its first patients [online] Press release, Health & Medicine Week, 2004, retrieved from NewsRx.com, Mar. 1, 2004, pp. 119-120.
International Preliminary Report on Patentability for PCT/US2014/071448, 14 pages (dated Jun. 30, 2016).
International Search Report and Written Opinion issued in corresponding PCT application No. PCT/US2014/071448 dated Jul. 24, 2015 (18 pages).
International Search Report for PCT/US2016/048037, 11 pages (dated Feb. 6, 2017).
Invitation to Pay Additional Fees and, where applicable, protest fee issued in PCT application PCT/US2014/071448 dated Apr. 13, 2015 (11 pages).
Invitation to Pay Additional Fees and, where applicable, protest fee issued in PCT application PCT/US2016/048037 dated Oct. 20, 2016 (8 pages).
Ishibashi and Mcinturff, Stress Analysis of Superconducting 1 OT Magnets for Synchrotron, Proceedings of the Ninth International Cryogenic Engineering Conference, May 11-14, 1982, pp. 513-516.
Ishibashi and Mcinturff, Winding Design Study of Superconducting 10 T Dipoles for a Synchrotron, IEEE Transactions on Magnetics, May 1983, MAG-19(3):1364-1367.
Jahnke et al., First Superconducting Prototype Magnets for a Compact Synchrotron Radiation Source in Operation, IEEE Transactions on Magnetics, Mar. 1988, 24(2):1230-1232.
Jones and Dershem, Synchrotron Radiation from Proton in a 20 TEV, 10 TESLA Superconducting Super Collider Proceedings of the 12th International Conference on High-Energy Accelerator, Aug. 11-16, 1983, pp. 138-140.
Jones and Mills, The South African National Accelerator Centre: Particle Therapy and Isotope Production Programmes, Radiation Physics and Chemistry, Apr.-Jun. 1998, 51 (4-6):571-578.
Jones et al., Status Report of the NAC Particle Therapy Programme, Stralentherapie und Onkologie, vol. 175, Suppl. II, Jun. 1999, pp. 30-32.
Jones, Present Status and Future Trends of Heavy Particle Radiotherapy, Cyclotrons and their Applications 1998, Proceedings of the Fifteenth International Conference on Cyclotrons and their Applications, Jun. 14-19, 1998, pp. 13-20.
Jones, Progress with the 200 MeV Cyclotron Facility at the National Accelerator Centre, Commission of the European Communities Radiation Protection Proceedings, Fifth Symposium on Neutron Dosimetry, Sep. 17-21, 1984, vol. II, pp. 989-998.
Jongen et al., Development of a Low-cost Compact Cyclotron System for Proton Therapy, National Institute of Radiol. Sci,1991, No. 81, DD. 189-200.
Jongen et al., Progress report on the IBA-SHI small cyclotron for cancer therapy Nuclear Instruments and Methods in Physics Research, Section B, vol. 79, issue 1-4, 1993, pp. 885-889.
Jongen et al., The proton therapy system for MGH's NPTC: equipment description and progress report, Bulletin du Cancer/Radiotherapie, Proceedings of the meeting of the European Heavy Particle Therapy Group, 1996, 83(Suppl. 1):219-222.
Jongen et al., The proton therapy system for the NPTC: Equipment Description and progress report, Nuclear Instruments and methods in physics research, 1996, Section B, 113(1): 522-525.
Kanai et al., Three-dimensional Beam Scanning for Proton Therapy, Nuclear Instruments and Methods in Physic Research, Sep. 1, 1983, The Netherlands, 214(23):491-496.
Karlin et al., Medical Radiology (Moscow), 1983, 28, 13.
Karlin et al., The State and Prospects in the Development of the Medical Proton Tract on the Synchrocyclotron in Gatchina, Med. Radial., Moscow, 28(3):28-32 (Mar. 1983)(German with English Abstract on end of p. 32).
Kats and Druzhinin, Comparison of Methods for Irradiation Prone Patients, Atomic Energy, Feb. 2003, 94(2): 120-123.
Kats and Onosovskii, A Planar Magnetooptical System for the Irradiation of a Lying Patient with a Proton Beam from Various Directions, Instruments and Experimental Techniques, 1996, 39(1):127-131.

(56) References Cited

OTHER PUBLICATIONS

Kats and Onosovskii, A Simple, Compact, Flat System for the Irradiation of a Lying Patient with a Proton Beam from Different Directions, Instruments and Experimental Techniques, 1996, 39(1):132-134.
Khoroshkov et al., Moscow Hospital-Based Proton Therapy Facility Design, Am. Journal Clinical Oncology: CCT, Apr. 1994, 17(2):109-114.
Kim and Blosser, Optimized Magnet for a 250 MeV Proton Radiotherapy Cyclotron, Cyclotrons and Their Applications 2001, May 2001, Sixteenth International Conference, pp. 345-347.
Kim and Yun, A Light-Ion Superconducting Cyclotron System for Multi-Disciplinary Users, Journal of the Korean Physical Society, Sep. 2003, 43(3):325-331.
Kim et al., Construction of 8T Magnet Test Stand for Cyclotron Studies, IEEE Transactions on Applied Superconductivity, Mar. 1993, 3(1):266-268.
Kim et al., Design Study of a Superconducting Cyclotron for Heavy Ion Therapy, Cyclotrons and Their Applications 2001, Sixteenth International Conference, May 13-17 2001, pp. 324-326.
Kim et al., Trim Coil System for the Riken Cyclotron Ring Cyclotron, Proceedings of the 1997 Particle Accelerator Conference, IEEE, Dec. 1981, vol. 3, pp. 214-235 or 3422-3424, 1998.
Kim, An Eight Tesla Superconducting Magnet for Cyclotron Studies, Ph.D. Dissertation, Michigan State University, Department of Physics and Astronomy, 1994, 13 8 pages.
Kimstrand, Beam Modelling for Treatment Planning of Scanned Proton Beams, Digital Comprehensive Summaries of Uppsala dissertations from the Faculty of Medicine 330, Uppsala Universitet, 2008, 58 pages.
Kishida and Yano, Beam Transport System for the RIKEN SSC (II), Scientific Papers of the Institute of Physical and Chemical Research, Dec. 1981, 75(4):214-235.
Koehler et al., Range Modulators for Protons and Heavy Ions, Nuclear Instruments and Methods, 1975, vol. 131, pp. 437-440.
Koto and Tsujii, Future of Particle Therapy, Japanese Journal of Cancer Clinics, 2001, 47(1):95-98 [Lang.: Japanese], English abstract (htt12://sciencelinks.j12/jeast/article/200206/000020020601A05 I I 453 .nhn).
Kraft et al., Hadrontherapy in Oncology, U. Amaldi and Larrsson, editors Elsevier Science, 1994, 161 pages.
Krevet et al., Design of a Strongly Curved Superconducting Bending Magnet for a Compact Synchrotron Light Source, Advances in Cryogenic Engineering, 1988, vol. 33, pp. 25-32.
Laisne et al., The Orsay 200 MeV Synchrocyclotron, IEEE Transactions on Nuclear Science, Apr. 1979, NS-26(2):1919-1922.
Larsson, B., et al., "The High-Energy Proton Beam As a Neurosurgical Tool," Nature vol. 182, pp. 1222-1223 (1958).
Larsson, Biomedical Program for the Converted 200-MeV Synchrocyclotron at the Gustaf Werner Institute, Radiation Research, 1985, 104:S310-S318.
Lawrence et al., Heavy particles in acromegaly and Cushing's Disease, in Endocrine and Norendocrine Hormone Producing Tumors (Year Book Medical Chicago, 1973, pp. 29-61.
Lawrence et al., Successful Treatment of Acromegaly: Metabolic and Clinical Studies in 145 Patients, The Journal of Clinical Endrocrinology and Metabolism, Aug. 1970, 31(2), 21 pages.
Lawrence et al., Treatment of Pituitary Tumors, (Excerpta medica, Amsterdam/American Elsevier, New York, 1973, pp. 253-262.
Lawrence, J.H., Proton Irradiation of the Pituitary Cancer, vol. 10, pp. 795-798 (1957).
Lecroy et al., Viewing Probe for High Voltage Pulses, Review of Scientific Instruments USA, Dec. 1960, 31(12):1354.
Lin et al., Principles and 10 Year Experience of the Beam Monitor System at the PSI Scanned Proton Therapy Facility, Center for Proton Radiation Therapy, Paul Scherrer Institute, CH-5232, Villigen PSI, Switzerland, 2007, 21 pages.
Linfoot et al., Acromegaly, in Hormonal Proteins and Peptides, edited by C.H. Li, 1975, pp. 191-246.
Literature Author and Keyword Search, Feb. 14, 2005, 44 pages.
Literature Keyword Search, Jan. 24, 2005, 98 pages.
Literature Search and Keyword Search for Synchrocyclotron, Jan. 25, 2005, 68 pages.
Literature Search by Company Name/Component Source, Jan. 24, 2005, 111 pages.
Literature Search, Jan. 26, 2005, 37 pages.
Livingston, M.S., et al. A Capillary Ion Source for the Cyclotron, Review Science Instruments, vol. 10, p. 9. 63-67, (1939).
LLNL, UC Davis Team Up to Fight Cancer, Lawrence Livermore National Laboratory, Apr. 28, 2006, SF-06-04-02, Livermore, California, pp. 1-4.
Machine translation of JP11-028252A from jpo website Jul. 17, 2015.
Mandrillon, High Energy Medical Accelerators, EPAC 90, 2nd European Particle Accelerator Conference, Jun. 12-16, 1990, 2:54-58.
Marchand et al., IBA Proton Pencil Beam Scanning: an Innovative Solution for Cancer Treatment, Proceedings of EP AC 2000, Vienna, Austria, 3 pages.
Marti et al., High Intensity Operation of a Superconducting Cyclotron, Proceedings of the I 4the International Conference, Cyclotrons and Their Applications, Oct. 1995, pp. 45-48 (Oct. 1995).
Martin, Operational Experience with Superconducting Synchrotron Magnets Proceedings of the 1987 IEEE Particle Accelerator Conference, Mar. 16-19, 1987, vol. 3 of 3: 1379-1382.
Meote et al., ETOILE Hadrontherapy Project, Review of Design Studies Proceedings of EPAC 2002, 2002, pp. 2745-2747.
Miyamoto et al., Development of the Proton Therapy System, The Hitachi Hyoron, 79(10):775-775 779 (1997) [Lang: Japanese], English abstract (http://www.hitachi.com/rev/1998/revfeb98/rev4 706.htm).
Moignier, A. et al., Toward improved target conformity for two spot scanning proton therapy delivery systems using dynamic collimation, Medical Physics, 43:1421-1427 (2014).
Montelius et al., The Narrow Proton Beam Therapy Unit at the Svedberg Laboratory in Uppsala, ACTA Oncologica, 1991, 30:739-745.
Moser et al., Nonlinear Beam Optics with Real Fields in Compact Storage Rings, Nuclear Instruments & Methods in Physics Research/Section B, B30, Feb. 1988, No. 1, pp. 105-109.
Moyers et al., A Continuously Variable Thickness Scatterer for Proton Beams Using Self-compensating Dual Linear Wedges Loma Linda University Medical Center, Dept. of Radiation Medicine, Loma Linda, CA, Nov. 2, 1992, 21 pages.
National Cancer Institute Funding (Senate-Sep. 21, I 992} (wvw.tbomas.loc.gov/cgibin/querv/z?rl02:S21SE2-7l2 (2 pages).
Nicholson, Applications of Proton Beam Therapy, Journal of the American Society of Radiologic Technologists, May/Jun. 1996, 67(5): 439-441.
Nolen et al., The Integrated Cryogenic—Superconducting Beam Transport System Planned for MSU, Proceedings of the J21h International Conference on High-Energy Accelerators, Aug. 1983, pp. 549-551.
Norimine et al., A Design of a Rotating Gantry with Easy Steering for Proton Therapy, Proceedings of EPAC 2002, 2002, pp. 2751-2753.
Office Action for U.S. Appl. No. 14/137,854, 32 pages (dated Dec. 22, 2016).
Ogino, Takashi, Heavy Charged Particle Radiotherapy-Proton Beam, Division of Radiation Oncology, National Cancer Hospital East, Kashiwa, Japan, Dec. 2003, 7 pages.
Okumura et al., Overview and Future Prospect of Proton Radiotherapy, Japanese Journal of Cancer Clinics, 1997, 43(2):209-214 [Lang.: Japanese].
Okumura et al., Proton Radiotherapy Japanese Journal of Cancer and Chemotherapy, 1993, 10. 20(14):2149-2155[Lang.: Japanese].
Outstanding from Search Reports, Accelerator of Polarized Portons at Fermilab, 2005, 20 pages.
Paganetti et al., Proton Beam Radiotherapy—The State of the Art, Springer Verlag, Heidelberg, ISBN 3-540-00321-5, Oct. 2005,36 pages.

(56) References Cited

OTHER PUBLICATIONS

Palmer and Tollestrup, Superconducting Magnet Technology for Accelerators, Annual Review of Nuclear and Particle Science, 1984, vol. 34, pp. 247-284.
Patent Assignee and Keyword Searches for Synchrocyclotron, Jan. 25, 2005, 78 pages.
Patent Assignee Search Paul Scherrer Institute, Library Services at Fish & Richardson P.C., Mar. 20, 2007, 40 pages.
Patent Prior Art Search for 'Proton Therapy System', Library Services at Fish & Richardson P.C., Mar. 20, 2007, 46 pages.
Pavlovic, Beam-optics study of the gantry beam delivery system for light-ion cancer therapy, Nuclear Instruments and Methods in Physics Research, Section A, Nov. 1997, 399(2):439-454(16).
Pedroni and Enge, Beam optics design of compact gantry for proton therapy Medical & Biological Engineering & Computing, May 1995, 33(3):271-277.
Pedroni et al., A Novel Gantry for Proton Therapy at the Paul Scherrer Institute, Cycloctrons and Their Applications 2001: Sixteenth International Conference. AIP Conference Proceedings, 2001, 600:13-17.
Pedroni et al., The 200-MeV proton therapy project at the Paul Scherrer Institute: Conceptual design and practical realization, Medical Physics, Jan. 1995, 22(1 ):37-53.
Pedroni, Accelerators for Charged Particle Therapy: Performance Criteria from the User Point of View, Cyclotrons and their Applications, Proceedings of the 13th International Conference, Jul. 6-10, 1992, pp. 226-233.
Pedroni, E. and Jermann, M. "SGSMP: Bulletin Mar. 2002 Proscan Project, Progress Report on the PROSCAN Project of PSI," [online] retrieved from www.sgsmp.ch/protA23.htm, (5 pages) Mar. 2002.
Pedroni, Latest Developments in Proton Therapy Proceedings of EPAC 2000, pp. 240-244, 2000.
Pedroni, Status of Proton Therapy: results and future trends, Paul Scherrer Institute, Division of Radiation Medicine, 1994, 5 pages.
Peggs et al., A Survey of Hadron Therapy Accelerator Technologies, Particle Accelerator Conference, Jun. 25-29 2008, 7 pages.
Potts et al., MPWP6-Therapy III: Treatment Aids and Techniques Medical Physics, Sep./Oct. 1988, 15(5):798.
Pourrahimi et al., Powder Metallurgy Processed Nb3Sn(Ta) Wire for High Field NMR magnets, IEEE Transactions on Applied Superconductivity, Jun. 1995, 5(2):1603-1606.
Prieels et al., The IBA State-of-the-Art Proton Therapy System, Performances and Recent Results, Application of Accelerators in Research and industry—Sixteenth Int'l Conj, American Institute of Physics, Nov. 1-5, 2000, 576:857-860.
Proiect of PSI [online] retrieved from www.sgsmp.ch/protA23.htm, Mar. 2002, 5 pages.
Rabin et al., Compact Designs for Comprehensive Proton Beam Clinical Facilities, Nuclear Instruments & Methods in Physics Research, Apr. 1989, Section B, vol. 40-41, Part II, pp. 1335-1339.
Research & Development Magazine, Proton Therapy Center Nearing Completion, Aug. 1999, 41(9):2 pages (www.rdmag.com).
Resmini Design Characteristics of the K=800 Superconducting Cyclotron at M.S.U., Cyclotron Laboratory, Michigan State University, East Lansing, Michigan 48824, IEEE Transaction on Nuclear Science, vol. NS-26, No. 2, Apr. 1979, 8 pages.
RetroSearch Berkeley 88-Inch Cyclotron 'Rf' or 'Frequency Control', Jan. 21, 2005, 36 pages.
RetroSearch Berkeley 88-Inch Cyclotron, Jan. 24, 2005, 170 pages.
RetroSearch Bernard Gottschalk, Cyclotron, Beams, Compensated Upstream Modulator, Compensated Scatter, Jan. 21, 2005, 20 pages.
RetroSearch Cyclotron with 'Rf' or 'Frequency Control', Jan. 21, 2005, 49 pages.
RetroSearch Gottschalk, Bernard, Harvard Cyclotron Wheel, Jan. 21, 2005, 20 pages.
RetroSearch Loma Linda University Beam Compensation, Jan. 21, 2005, 60 pages.
RetroSearch Loma Linda University, Beam Compensation Foil Wedge, Jan. 21, 2005, 15 pages.
Revised Patent Keyword Search, Jan. 25, 2005, 86 pages.
Rifuggiato et, al., Status Report of the LNS Superconducting Cyclotron Nukleonika, 2003, 48:SI31-SI34, Supplement 2.
Rode, Tevatron Cryogenic System, Proceedings of the 12th International Conference on Highenergy Accelerators, Fermilab, Aug. 11-16, 1983, pp. 529-535.
Salzburger et al., Superconducting Synchrotron Magnets Supraleitende Synchrotronmagnete, NTiS, 155 pages (Oct. 1975).
Schillo et al,. Compact Superconducting 250 MeV Proton Cyclotron for the PSI Proscan Proton Therapy Project, Cyclotrons and Their Applications 2001, Sixteenth International Conference, 2001, pp. 37-39.
Schneider et al., Nevis Synchrocyclotron Conversion Program<RF System, IEEE Transactions on Nuclear Science USA, Jun. 1969, ns. 16(3): 430-433.
Schneider et al., Superconducting Cyclotrons, IEEE Transactions on Magnetics, vol. MAG-11, No. 2, Mar. 1975, New York, pp. 443-446.
Schreuder et al., The Non-orthogonal Fixed Beam Arrangement for the Second Proton Therapy Facility at the National Accelerator Centre, Application of Accelerators in Research and Industry, American Institute of Physics, Proceedings of the Fifteenth International Conference, Nov. 1998, Part Two, pp. 963-966.
Schreuder, Recent Developments in Superconducting Cyclotrons, Proceedings of the 1995 Particle Accelerator Conference, May 1-5, 1995, vol. 1, pp. 317-321.
Schubert and Blosser, Conceptual Design of a High Field Ultra-Compact Cyclotron for Nuclear Physics Research, Proceedings of the 1997 Particle Accelerator Conference, May 12-16, 1997, vol. 1, 3 pp. 1060-1062.
Schubert, Extending the Feasibility Boundary of the Isochronous Cyclotron, Dissertation submitted to Michigan State University, 1997, Abstract http://adsabs.harvard.edu/abs/1998PhDt ....... 147S.
Shelaev et al., Design Features of a Model Superconducting Synchrotron of JINR, Proceedings of the 12th International Conference on High-energy Accelerators, Aug. 11-16, 1983, pp. 416-418.
Shintomi et. Al, Technology and Materials for the Superconducting Super Collider (SSC) Project, [Lang.: Japanese], The Iron and Steel Institute of Japan 00211575, 78(8): 1305-1313, 1992, http://ci.nii.ac.ip/naid/l 1 0001493249/en/.
Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesmin. Fuer Forsch. U. Technol. In German; English Summary.
Sisterson, Clinical use of proton and ion beams from a world-wide perspective, Nuclear Instruments and Methods in Physics Research, Section B, 1989, 40-41:1350-1353.
Sisterson, World Wide Proton Therapy Experience in 1997, The American Institute of Physics, Applications of Accelerators in Research and Industry, Proceedings of the Fifteenth International Conference, Part Two, Nov. 1998, pp. 959-962.
Slater et al., Developing a Clinical Proton Accelerator Facility: Consortium-Assisted Technology Transfer, Conference Record of the 1991 IEEE Particle Accelerator Conference: Accelerator Science and Technology, vol. I, May 6-9, 1991, pp. 532-536.
Slater et al., Development of a Hospital-Based Proton Beam Treatment Center, International Journal of Radiation Oncology, Biology and Physics, Apr. 1988, 14(4):761-775.
Smith et al., The Northeast Proton Therapy Center at Massachusetts General Hospital Journal of Brachytherapy International, Jan. 1997, pp. 137-139.
Snyder and Marti, Central region design studies for a proposed 250 MeV proton cyclotron, Nuclear Instruments and Methods in Physics Research, Section A, 1995, vol. 355, pp. 618-623.
Soga, Progress of Particle Therapy in Japan, Application of Accelerators in Research and Industry, American Institute of Physics, Sixteenth International Conference, Nov. 2000, pp. 869-872.
Spiller et al., The GSI Synchrotron Facility Proposal for Acceleration of High Intensity Ion and Proton Beams Proceedings of the 2003 Particle Accelerator Conference, May 12-16, 2003, vol. 1, pp. 589-591.

(56) References Cited

OTHER PUBLICATIONS

Stanford et al., Method of Temperature Control in Microwave Ferroelectric Measurements, Sperry Microwave Electronics Company, Clearwater, Florida, Sep. 19, 1960, 1 page.
Superconducting Cyclotron Contract awarded by Paul Scherrer Institute (PSI), Villigen, Switzerland, http://www.accel.de/News/superconducting_ cyclotron_ contract.htm, Jan. 2009, 1 page.
Tadashi et al., Large superconducting super collider (SSC) in the planning and materials technology,78(8):1305-1313, The Iron and Steel Institute of Japan 00211575, Aug. 1992.
Takada, Conceptual Design of a Proton Rotating Gantry for Cancer Therapy, Japanese Journal of Medical Physics, 1995, 15(4):270-284.
Takayama et al., Compact Cyclotron for Proton Therapy, Proceedings of the 81h Symposium on Accelerator Science and Technology, Japan, Nov. 25-27, 1991, pp. 380-382.
Teng, The Fermilab Tevatron, Coral Gables 1981, Proceedings, Gauge Theories, Massive Neutrinos, and Proton Decay, 1981, pp. 43-62.
The Davis 76-Inch Isochronous Cyclotron, Beam On: Crocker Nuclear Laboratory, University of California, 2009, 1 page.
The Journal of Practical Pharmacy,1995, 46(1):97-103 [Japanese].
The K100 Neutron-therapy Cyclotron, National Superconducting Cyclotron Laboratory at Michigan State University (NSCL), retrieved from: http://www.nscl.msu.edu/tech/accelerators/kl 00, Feb. 2005, 1 page.
The K250 Proton therapy Cyclotron, National Superconducting Cyclotron Laboratory at Michigan State University (NSCL), retrieved from: http://www.nscl.msu.edu/tech/accelerators/k.250.html, Feb. 2005, 2 pages.
The K250 Proton-therapy Cyclotron Photo Illustration, National Superconducting Cyclotron Laboratory at Michigan State University (NSCL), retrieved from: http://www.nscl.msu.edu/media/image/ experimental-equipment-technology /25 0 .html, Feb. 2005, 1 page.
Tilly, et al., Development and verification of the pulsed scanned proton beam at The Svedberg Laboratory in Uppsala, Physics in Medicine and Biology, Phys. Med. Biol. 52, pp. 2741-2454, 2007.
Tobias, C.A., et al., Pituitary Irradiation with High-Energy Proton Beams a Preliminary Report, Cancer Research, vol. 18, No. 2, pp. 121-134 (1958).
Tom, The Use of Compact Cyclotrons for Producing Fast Neutrons for Therapy in a Rotatable Isocentric Gantry, IEEE Transaction on Nuclear Science, Apr. 1979, 26(2):2294-2298.
Torikoshi, M. et al., Irradiation System for HIMAC, J. Radiat. Res, 48: Suppl. A15-A25 (2007).
Toyoda, Proton Therapy System, Sumitomo Heavy Industries, Ltd., 2000, 5 pages.
Trinks et. al., The Tritron: A Superconducting Separated-Orbit Cyclotron, Nuclear Instruments and Methods in Physics Research, Section A, 1986, vol. 244, pp. 273-282.
Tsuji, The Future and Progress of Proton Beam Radiotherapy, Journal of Japanese Society for Therapeutic Radiology and Oncology, 1994, 6(2):63-76.
U.S. Appl. No. 13/830,792, filed Mar. 14, 2013, including the USPTO electronic file for U.S. Appl. No. 13/830,792.
U.S. Appl. No. 13/949,459, filed Jul. 24, 2013, including the USPTO electronic file for U.S. Appl. No. 13/949,459.
U.S. Appl. No. 61/676,377, filed Jul. 27, 2012, including the USPTO electronic file for U.S. Appl. No. 61/676,377.
UC Davis School of Medicine, Unlikely Partners Tum Military Defense into Cancer Offense, Current Issue Summer 2008, Sacramento, California, pp. 1-2.
Umegaki et al., Development of an Advanced Proton Beam Therapy System for Cancer Treatment Hitachi Hyoron, 2003, 85(9):605-608 [Lang.: Japanese], English abstract, http://www.hitachi.com/ICSFiles/afieldfile/2004/06/0 1/r2003 _ 04_1 04.pdf or http://www.hitachi.com/rev/archive/2003/2005649_12606.html (full text) [Hitachi, 52(4), Dec. 2003].

Umezawa et al., Beam Commissioning of the new Proton Therapy System for University of Tsukuba, Proceedings of the 2001 Particle Accelerator Conference, vol. 1, Jun. 18-22, 2001, pp. 648-650.
Van Steenbergen, Superconducting Synchroton Development at BNL, Proceedings of the 8th International Conference on High-Energy Accelerators CERN 1971, 1971, pp. 196-198.
Van Steenbergen, The CMS, a Cold Magnet Synchrotron to Upgrade the Proton Energy Range of the BNL Facility, IEEE Transactions on Nuclear Science, Jun. 1971, 18(3):694-698.
Vandeplassche et al., 235 MeV Cyclotron for MGH's Northeast Proton Therapy Center (NPTC): Present Status, EPAC 96, Fifth European Partical Accelerator Conference, vol. 3, Jun. 10-14, 1996, pp. 2650-2652.
Vorobiev et al., Concepts of a Compact Achromatic Proton Gantry with a Wide Scanning Field, Nuclear Instruments and Methods in Physics Research, Section A., 1998, 406(2):307-310.
Vrenken et al., A Design of a Compact Gantry for Proton Therapy with 2D-Scanning, Nuclear Instruments and Methods in Physics Research, Section A, 1999, 426(2):618-624.
Wikipedia, Cyclotron http://en.wiki11edia.org/wiki/Cyclotron (originally visited Oct. 6, 2005, revisited Jan. 28, 2009), 7 pages.
Wikipedia, Synchrotron http://en.wiki11edia.org/wiki/Synchrotron (originally visited Oct. 6, 2005, revisited Jan. 28, 2009), 7 pages.
Worldwide Patent Assignee Search, Jan. 24, 2005, 224 pages.
Worldwide Patent Keyword Search, Jan. 24, 2005, 94 pages.
Written Opinion for PCT/US2016/048037, 12 pages (dated Feb. 6, 2017).
Wu, Conceptual Design and Orbit Dynamics in a 250 MeV Superconducting Synchrocyclotron, Ph.D. Dissertation, Michigan State University, Department of Physics and Astronomy, 1990, 172 pages.
York et al., Present Status and Future Possibilities at NSCL-MSU, EP AC 94, Fourth European Particle Accelerator Conference, pp. 554-556, Jun. 1994.
York et al., The NSCL Coupled Cyclotron Project—Overview and Status, Proceedings of the Fifteenth International Conference on Cyclotrons and their Applications, Jun. 1998, pp. 687-691.
Yudelev et al., Hospital Based Superconducting Cyclotron for Neutron Therapy: Medical Physics Perspective, Cyclotrons and their applications 2001, 16th International Conference. American Institute of Physics Conference Proceedings, vol. 600, May 13-17, 2001, pp. 40-43.
Zherbin et al., Proton Beam Therapy at the Leningrad Synchrocyclotron (Clinicomethodological Aspects and Therapeutic Results), Aug. 1987, 32(8):17-22, (German with English abstract on pp. 21-22).
International Search Report for PCT/US2018/018590 (Automated Treatment in Particle Therapy, filed Feb. 19, 2018), issued by ISA/EP, 9 pages (dated Jul. 13, 2018).
Written Opinion for PCT/US2018/018590 (Automated Treatment in Particle Therapy, filed Feb. 19, 2018), issued by ISA/EP, 13 pages (dated Jul. 13, 2018).
International Preliminary Report on Patentability for PCT/US2018/018590, 12 pages (dated Sep. 6, 2019).
Communication pursuant to Article 94(3) EPC for EP 18708034.6, 7 pages (dated May 28, 2020).
First Office Action in Chinese Patent Application No. 201880026046. 7, dated Oct. 28, 2020, with English Translation, (36) pages.
First Office Action in Japanese Patent Application No. 2019-545952, dated Aug. 7, 2020, with English Translation, (17) pages.
Communication pursuant to Article 94(3) EPC for EP 18708034.6, 7 pages (dated Mar. 11, 2021).
Blosser, Progress on the Coupled Superconducting Cyclotron Program, Bulletin of the American, Apr. 1991, (3 pages).
Second Office Action in Chinese Patent Application No. 201880026046. 7, dated May 18, 2021, with English Translation, (27) pages.
Second Office Action in Japanese Patent Application No. 2019-545952, dated Apr. 26, 2021, with English Translation, (13) pages.

\* cited by examiner

AUTOMATED TREATMENT IN PARTICLE THERAPY

TECHNICAL FIELD

This disclosure relates generally to a particle therapy system that implements automated treatment.

BACKGROUND

Traditionally, particle therapy has been delivered isocentrically, where the approximate center of an irradiation target in a patient is positioned at a unique location, known as the isocenter, in a treatment space. A radiation source is arranged so that a central axis of the radiation source points to the isocenter. The radiation source is rotated around the isocenter, and the patient is also rotated around this same isocenter. By positioning the radiation source and the patient in this manner, the target may be irradiated from a number of projections, which correspond to different beam fields. As a result, a radiation dose to the target may be increased, while radiation to surrounding normal tissue may be reduced.

A dosimetrist working with a treatment planning system (TPS) may choose the projections. The TPS uses information about the patient's anatomy, the radiation source, and other available information to determine the planned dose for each chosen projection. The number of projections has typically been chosen so that the quality of the therapy is enhanced, without unduly burdening the radiation delivery process. Traditionally, treatment is administered for each projection by verifying the positioning of the patient and/or the radiation emitter prior to the first application of radiation. A radiation therapist enters the treatment room before the first projection and between each successive projection to reposition the patient and/or a radiation emitter as specified by the treatment plan.

This required manual intervention by a radiation therapist makes it difficult, and time-consuming, to implement a large number of projections. Also, the quality of the treatment can be affected in areas where projections may overlap.

SUMMARY

An example particle therapy system comprises a particle beam output device to direct output of a particle beam; a treatment couch to support a patient containing an irradiation target, with the treatment couch being configured for movement; a movable device on which the particle beam output device is mounted for movement relative to the treatment couch; and a control system to provide automated control of at least one of the movable device or the treatment couch to position at least one of the particle beam or the irradiation target for treatment of the irradiation target with the particle beam and, following the treatment of the irradiation target with the particle beam, to provide automated control of at least one of the movable device or the treatment couch to reposition at least one of the particle beam or the irradiation target for additional treatment of the irradiation target with the particle beam. The example particle therapy system may include one or more of the following features, either alone or in combination.

The example particle therapy system may include a scanning system comprising components to move the particle beam relative to the irradiation target. The control system may be configured to provide automated control of one or more of the components to position the particle beam for the treatment of the irradiation target with the particle beam and, following the treatment of the irradiation target with the particle beam, to provide automated control of one or more of the components to reposition the particle beam for the additional treatment of the irradiation target with the particle beam. The one or more components may comprise one or more scanning magnets. The one or more components may comprise an energy degrader, with the energy degrader comprising one or more structures that are movable into, and out of, a path of the particle beam.

The control system may be configured to provide the automated control of at least one of the movable device or the treatment couch to treat a first part of the irradiation target using a first beam field of the particle beam and, following treatment of the first part of the irradiation target with the particle beam, to provide the automated control of at least one of the movable device or the treatment couch to reposition at least one of the particle beam or the irradiation target to treat a second part of the target using a second beam field of the particle beam.

The particle beam output device may comprise a particle accelerator. At an area between the first beam field and the second beam field, the particle beam for the first beam field and the particle beam for the second beam field may overlap at least partly. The control system may be configured to provide automated control of the particle accelerator to control intensities of the particle beam for the first beam field and the particle beam for the second beam field so that cumulative intensities at points of overlap between the particle beam for the first beam field and the particle beam for the second beam field reach a target beam intensity.

The particle beam output device may comprise a particle accelerator. At an area between the first beam field and the second beam field, the particle beam for the first beam field and the particle beam for the second beam field may overlap at least partly. The control system may be configured to provide automated control of the particle accelerator to control intensities of the particle beam for the first beam field and the particle beam for the second beam field so that cumulative intensities at points of overlap between the particle beam for the first beam field and the particle beam for the second beam field do not deviate from a target beam intensity by more than a defined amount.

The control system may be configured to control the treatment couch to implement translational motion. The control system may be configured to control the treatment couch to implement rotational motion.

The example particle therapy system may comprise an imaging system to capture images of the irradiation target during treatment. The control system may be configured to control the imaging system to capture one or more first images of the patient after positioning the at least one of the particle beam or the irradiation target for the treatment and before the treatment of the irradiation target with the particle beam, and the control system may be configured to control the imaging system to capture one or more second images of the patient after repositioning the at least one of the particle beam or the irradiation target for the additional treatment and before the additional treatment. The control system may be configured to use the first image to identify a first location of the irradiation target in a treatment space of the particle therapy system (e.g., in a proton center), and the control system may be configured to use the second image to identify a second location of the irradiation target in the treatment space.

The control system may be configured to receive a treatment plan from a treatment planning system, and to interpret the treatment plan to implement the control of at least one of the movable device or the treatment couch. The treatment plan may contain information identifying positions of at least one of the movable device or the treatment couch during treatment.

The control system may be configured to provide automated control of at least one of the movable device or the treatment couch independent of an isocenter defined in the particle therapy system. Automated control of at least one of the movable device or the treatment couch may be implemented absent human intervention.

The particle beam output device may comprise a particle accelerator. The control system may be configured to provide automated control of an operation of the particle accelerator to position at least one of the particle beam or the irradiation target for treatment of the irradiation target with the particle beam and, following the treatment of the irradiation target with the particle beam, to provide automated control of the operation of the particle accelerator to reposition at least one of the particle beam or the irradiation target for the additional treatment of the irradiation target with the particle beam.

The particle beam output device may comprise a synchrocyclotron having a superconducting electromagnetic structure. The particle beam output device may comprise a variable-energy synchrocyclotron having a superconducting electromagnetic structure. The particle beam output device may comprise a beam spreader. The beam spreader comprises one or more scanning magnets or one or more scattering foils The example particle therapy system may comprise a configurable collimator between the particle beam output device and the patient. The configurable collimator may comprise leaves that are controllable to define an edge to block a first part of the particle beam from reaching the patient while collimating a second part of the particle beam that passes to the patient. The configurable collimator may be controllable to trim an area as small as a single spot size of the particle beam.

The control system may be configured to provide automated control over movement of the particle beam output device to implement translational movement of the particle beam output device from a first location to a second location to position the particle beam for treatment of the irradiation target with the particle beam and, following the treatment of the irradiation target with the particle beam, to provide automated control over further movement of the particle beam output device to implement translational movement of the particle beam output device from the second location to a third location to reposition the particle beam for treatment of the irradiation target with the particle beam.

The control system may be configured to provide automated control over movement of the particle beam output device to pivot the particle beam output device from a first orientation to a second orientation to position the particle beam for treatment of the irradiation target with the particle beam and, following the treatment of the irradiation target with the particle beam, to provide automated control over further movement of the particle beam output device to pivot the particle beam output device from the second orientation to a third orientation to reposition the particle beam for treatment of the irradiation target with the particle beam.

The example particle therapy system may comprise a scanning system comprising components to move the particle beam relative to the irradiation target, with at least some of the components being mounted for movement towards, and away from, the irradiation target. The control system may be configured to provide automated control of the at least some of the components to position the particle beam for the treatment of the irradiation target with the particle beam and, following the treatment of the irradiation target with the particle beam, to provide automated control of the at least some of the components to reposition the particle beam for the additional treatment of the irradiation target with the particle beam.

The example particle therapy system may comprise a carriage on which the at least some of the components are mounted, with the carriage being mounted to at least one track to enable movement along a path of the particle beam. The carriage may be controllable to move along the at least one track to control a size of a spot produced by the particle beam. The carriage may be controllable to move along the at least one track in coordination with movement of at least one of the movable device or the treatment couch.

The movable device may comprise a rotatable gantry. The movable device may comprise one or more robotic arms.

The example particle therapy system may comprise a scanning system comprising components to move the particle beam relative to the irradiation target, with the scanning components being mounted on a carriage that is movable along a beamline of the particle beam. The control system may be configured to provide automated control of the carriage to position the particle beam for the treatment of the irradiation target with the particle beam and, following the treatment of the irradiation target with the particle beam, to provide automated control of the carriage to reposition the particle beam for the additional treatment of the irradiation target with the particle beam.

An example method comprises supporting a patient containing an irradiation target on a treatment couch, with the treatment couch being configured for movement; mounting a particle beam output device on a movable device for movement relative to the treatment couch, with the particle beam output device for directing output of a particle beam to treat the irradiation target; providing automated control of at least one of the movable device or the treatment couch to position at least one of the particle beam or the irradiation target for treatment of the irradiation target with the particle beam and, following treatment of the irradiation target with the particle beam, providing automated control at least one of the movable device or the treatment couch to reposition at least one of the particle beam or the irradiation target for additional treatment of the irradiation target with the particle beam. The particle beam may be a proton beam.

An example particle therapy system comprises a treatment couch to support a patient containing an irradiation target, with the treatment couch being configured for movement; a particle beam output device to direct output of a particle beam, with the particle beam output device being arranged for movement relative to the treatment couch; and a control system to control positioning of the particle beam output device and the treatment couch using degrees of freedom that exceed isocentric rotation of the particle beam output device and the treatment couch. The example particle therapy system may comprise one or more of the following features, either alone or in combination.

The particle beam output device may comprise scanning components to scan the particle beam relative to the irradiation target, with the scanning components comprising one or more scanning magnets. The control system may be configured to control a position of the particle beam by controlling operation of one or more of the scanning components The control system may be configured to control positioning of the particle beam output device and the treatment couch absent user intervention. The control system may be configured to control positioning of the particle beam output device and the treatment couch automatically for multiple beam fields. The particle beam output device may be controllable to move linearly between a first position and a second position. The particle beam output device may be controllable to pivot relative to the treatment couch. The particle beam output device may be controllable to rotate relative to the treatment couch. The particle beam output device may comprise a particle accelerator. The particle beam output device may be configured to produce a beam field of 30 cm by 30 cm or less.

An example particle therapy system comprises a treatment couch to support a patient containing an irradiation target, with the treatment couch being configured for movement; an apparatus to direct output of a particle beam; a movable device on which the apparatus is mounted to move the apparatus relative to the treatment couch, with the apparatus being mounted relative to the treatment couch to produce a beam field of 30 cm by 30 cm or less; and a control system to provide automated positioning of at least one of the apparatus or the treatment couch for treatment of a first part of the irradiation target with the particle beam and, following the treatment of the first part of the irradiation target with the particle beam, to provide automated repositioning at least one of the apparatus or the treatment couch for treatment of a second part of the irradiation target with the particle beam. The example particle therapy system may comprise one or more of the following features, either alone or in combination.

At least one of the automated positioning or the automated repositioning processes may comprise translational movement. The apparatus may comprise a beam spreader to deliver the particle beam via a transmission channel. The apparatus may comprise a particle accelerator configured to generate the particle beam. The apparatus may be mounted to produce a beam field of 20 cm by 20 cm or less. The apparatus may comprise a synchrocyclotron having a weight that is within a range of 5 tons to 30 tons and that occupies a volume of less than 4.5 cubic meters.

The example particle therapy system may comprise a collision avoidance system to detect positions of one or more components of the particle therapy system and to provide information about positions to the control system. The control system may be configured to control operation of the one or more components based on the information. The control system may be configured to provide automated control of the particle beam to control intensities of the particle beam so that cumulative intensities at points of overlap between a particle beam for a first beam field and a particle beam for a second beam field remain within a range of a target beam intensity.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices (e.g., microprocessor(s), application-specific integrated circuit(s), programmed logic such as field programmable gate array(s), or the like). The systems described herein, or portions thereof, may be implemented as an apparatus, method, or electronic system that may include one or more processing devices and computer memory to store executable instructions to implement control of the stated functions.

The details of one or more implementations are set forth in the accompanying drawings and the description below. Other features and advantages will be apparent from the description and drawings, and from the claims.

DESCRIPTION OF THE DRAWINGS

Like reference symbols in the various drawings indicate like elements.

DETAILED DESCRIPTION

Figure 1:
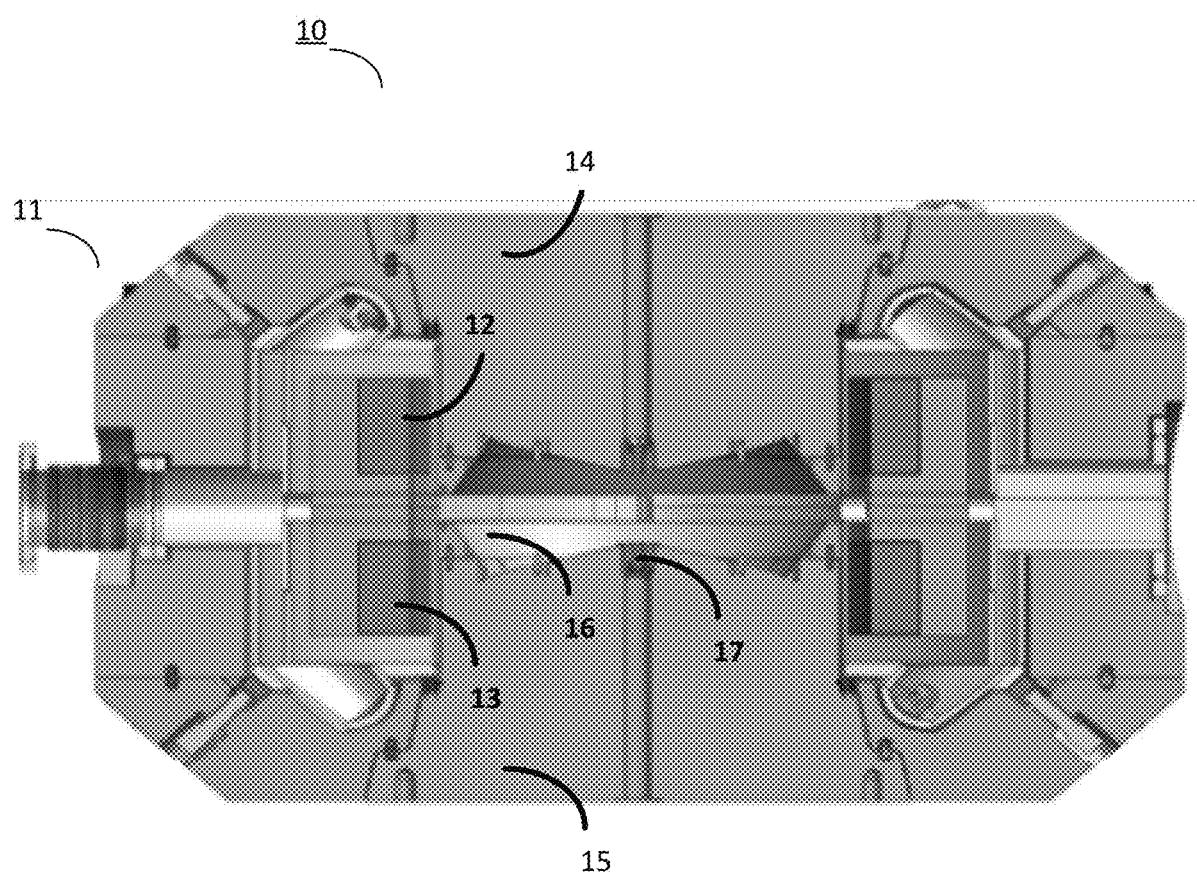
FIG. 1 is a cut-away, side view of components of an example synchrocyclotron that may be used in a particle therapy system.

Described herein are examples of particle therapy systems that are configured to automate treatment (e.g., delivery of particle beam) across sequential beam fields. Treatment furthermore is not limited to patient or accelerator movement relative to a single isocenter. Rather, in some implementations, components of the system, including those that affect beam position and patient position, may be computer-controlled to automate treatment at any appropriate point in an irradiation target, including across beam fields and without reference to an isocenter. Automating the treatment process, and reducing reliance on isocentric treatment, may provide for more treatment flexibility and support additional reductions in the size of the particle therapy system.

An example of a particle therapy system that is configurable to automate treatment in the manner described above is a proton or ion therapy system. In some implementations, the components of the proton therapy system that actually provide treatment, including the particle accelerator itself in some cases, are located in a single treatment room, called a proton center. In some implementations, the proton center is 30 feet (ft) by 30 ft by 30 ft (30 $ft^3$) or less in volume. In some implementations, the proton center is 37 feet (ft) by 32 ft by 28 ft or less in volume. In some implementations, a beam spreader (also referred to as a "spreader") is mounted for delivery of proton therapy to the patient. Examples of beam spreaders include, but are not limited to, one or more scanning magnets, examples of which are described herein, or one or more scattering foils. A scattering foil scatters the particle beam to produce a dispersed beam for application to a target in the patient. A scanning magnet moves a more concentrated version of the particle beam in at least two dimensions across a target in the patient.

The beam field produced by the beam spreader is based, at least in part, on the distance between the beam spreader and an isocenter in the patient. In this regard, the beam field (also called the irradiation field) corresponds to a projection of radiation—here a particle beam—from the spreader. A beam field may be represented conceptually by a plane that defines the maximum extent or range that a projection of a particle beam can move in the X and Y directions relative to the irradiation target. The size (e.g., the area) of a beam field may be based on the distance between the beam spreader and an isocenter in the patient. In implementations where the beam spreader includes one or more scanning magnets, the size of the beam field may also be based on the amount of current through the scanning magnets. That is, the more current that passes through the scanning magnets, the more the beam can be deflected, resulting in a larger beam field.

Because of the relatively small size of the proton center, the size of the beam field is limited. That is, because the proton center is relatively small, the distance between the beam spreader and the patient on a treatment couch is relatively short. In some implementations, the distance from the beam spreader to an isocenter in the patient may be 2 meters (m) or less, 1.7 m or less, 1.5 m, or less, 1 m or less, and so forth. As a result of this relatively short distance, the size of the beam field is also relatively small. For example, in some implementations, the size of the beam field may be 30 centimeters (cm) by 30 cm or less, 20 cm by 20 cm or less, and so forth. Also, large beam deflection angles are often discouraged for treatment, further limiting the size of the beam field.

The relatively small size of the beam field can affect treatment if the irradiation target (e.g., a tumor in a patient) exceeds the size of the beam field. For this reason, conventional proton therapy providers attempt to increase their field size as much as possible. By contrast, with the example compact system described herein—in particular one that delivers proton therapy in a single proton center—increasing the size of the beam field beyond a certain limit may be difficult in some examples due to physical limitations. Accordingly, the example systems described herein are configured to automatically treat an irradiation target using multiple beam fields. In some cases movement of the particle beam and the target are in degrees of freedom that exceed isocentric rotation of the particle accelerator or spreader and a treatment couch, making it possible to treat different beam fields automatically and, in some cases, absent user intervention.

The example particle therapy system includes a particle accelerator—in this example, a synchrocyclotron—mounted on a movable device. In some examples, the movable device is a gantry that enables the accelerator to be rotated at least part-way, and in some cases all the way, around a patient position to allow a particle beam from the synchrocyclotron to hit any arbitrary target in the patient. Any appropriate device, including a gantry, may be used to hold the particle accelerator and to move the particle accelerator in a rotational, translational, and/or pivotal motion relative to the patient. For example, the particle accelerator may be mounted to one or more tracks to enable motion relative to the patient. In another example, the particle accelerator may be mounted to one or more robotic arms to enable motion relative to the patient. In any case, the particle therapy system described herein is not limited to use with a gantry, to use with a rotational gantry, or to use with the example gantry configurations described herein. In some implementations, the beam spreader is mounted to the synchrocyclotron and is movable therewith. In some implementations, the beam spreader is mounted to the device—e.g., to the gantry—independent of the synchrocyclotron and is movable in the manner that the synchrocyclotron is described as being movable herein. The spreader is an example of a particle beam output device in that it directs the beam to the patient. Other examples of particle beam output devices are described herein including, but not limited to, the particle accelerator itself (or components thereof) which produces the particle beam and directs the output thereof.

In some implementations, the example synchrocyclotron has a high magnetic field superconducting electromagnetic structure. In general, a superconductor is an element or metallic alloy which, when cooled below a threshold temperature, loses most, if not all, electrical resistance. As a result, current flows through the superconductor substantially unimpeded. Superconducting coils, therefore, are capable of conducting much larger currents in their superconducting state than are ordinary wires of the same size. Because of the high amounts of current that superconducting coils are capable of conducting, magnets that employ superconducting coils are capable of generating high magnetic (B) fields for particle acceleration. Furthermore, because the bend radius of a charged particle having a given kinetic energy is reduced in direct proportion to an increase in the magnetic field applied to the charged particle, a high magnetic field superconducting electromagnetic structure enables the synchrocyclotron to be made compact, e.g., relatively small and light. More specifically, the higher the magnetic field used, the tighter the particle turn radius may be, thereby allowing for a larger numbers of turns to be made within a relatively small volume (that is, relative to larger, non-superconducting synchrocyclotrons). As a result, a desired particle energy—which increases with an increase in the number of turns—can be achieved using a synchrocyclotron having a relatively small size and weight. In some implementations, the synchrocyclotron is configured to produce a particle beam having sufficient energy to reach any arbitrary target within the patient from any appropriate position in the proton center relative to the patient.

By way of example, in some implementations, a maximum magnetic field produced in the acceleration cavity of the synchrocyclotron (e.g., at the center of the cavity) may be between 4 Tesla (T) and 20 T. In some implementations, the synchrocyclotron weighs less than 40 Tons. For example, the synchrocyclotron may have a weight that is within a range from 5 tons to 30 tons. In some implementations, the synchrocyclotron occupies a volume of less than 4.5 cubic meters. For example, the synchrocyclotron may occupy a volume in a range from 0.7 cubic meters to 4.5 cubic meters. In some implementations, the synchrocyclotron produces a proton or ion beam having an energy level of at least 150 MeV. For example, the synchrocyclotron may produce a proton or ion beam having an output energy level that is within a range from 150 MeV to 300 MeV, e.g., 230 MeV. Different implementations of the synchrocyclotron may have different values or combinations of values for size, volume, and energy level, including values not stated. Advantageously, the compact nature of the synchrocyclotron described herein allows the treatment to be performed in one room, i.e., in the proton center.

In this regard, traditionally, particle accelerators, including synchrocyclotrons, were considerably larger than the example compact accelerators described herein. By making the particle accelerator and the beam line (e.g., beam shaping) components compact, in some examples it is possible to enable operation of the system in closer patient proximity than has been possible with some traditional systems. For example, the compact size of the accelerator allows for mounting on the gantry (or other appropriate device), thereby reducing the cost and complexity of the whole system. But, in some examples, such a mounting may limit the space available for beam line (e.g., nozzle) components, forcing configuration of a relatively compact beam line. In some examples, this is one reason why an energy degrader as described herein is mounted in or on a nozzle that is relatively close to the patient, and in turn, why a collimator, also mounted in or on the nozzle, as described herein (which itself is compact) is used to keep beam edges sharp.

In some implementations, as described herein, the nozzle is mounted on an inner gantry that is within the sweep of the "outer" gantry holding the particle accelerator, that moves in synchronism with movement of the outer gantry, and that positions the nozzle to receive output of the accelerator on the outer gantry. In some implementations, the nozzle is mounted for movement on the inner gantry relative to the patient, e.g., along a C-shaped track. In some implementations, there may be no inner gantry, and all components described herein as being mounted to the inner gantry or to the nozzle are mounted to the outer gantry.

In some examples, the components mounted on the nozzle closest to the patient (e.g., a collimator and energy degrader) may present potential interference, so those components may be made relatively small. But, the size of those components is related to the treatable field size. That is, these smaller components may also decrease the beam field size. In some cases, by enabling the particle therapy system to perform treatment using multiple beam fields, more compact beamline elements may be used. As a result, a smaller nozzle, which may be positioned in even closer proximity to the patient, may be used.

FIG. 1 shows a cross-section of components 10 of an example superconducting synchrocyclotron that may be used in a particle therapy system. In this example, components 10 include a superconducting magnet 11. The superconducting magnet includes superconducting coils 12 and 13. The superconducting coils are formed, e.g., of multiple superconducting strands (e.g., four strands or six strands) wound around a center strand which may itself be superconducting or non-superconducting (e.g., copper). Each of the superconducting coils 12, 13 is for conducting a current that generates a magnetic field (B). The resulting magnetic field is shaped by magnetic yokes 14, 15. In an example, a cryostat (not shown) uses liquid helium (He) to maintain each coil at superconducting temperatures, e.g., around 4° Kelvin (K). The magnetic yokes 14, 15 (or smaller magnetic pole pieces) are located inside the cryostat, and define the shape of a cavity 16 in which particles are accelerated. Magnetic shims (not shown) may pass through the magnetic yokes or pole pieces to change the shape and/or magnitude of the magnetic field in the cavity.

In some implementations, the particle accelerator includes a particle source 17 (e.g., a Penning Ion Gauge—PIG source) to provide an ionized plasma column to the cavity 16. Hydrogen gas, or a combination of hydrogen gas and a noble gas, is ionized to produce the plasma column. A voltage source provides a varying radio frequency (RF) voltage to cavity 16 to accelerate pulses of particles from the plasma column within the cavity. The magnetic field in the cavity is shaped to cause particles to move orbitally within the cavity. In some implementations, the maximum magnetic field produced by the superconducting coils may be within the range of 4 Tesla (T) to 20 T, as explained herein. The example synchrocyclotron employs a magnetic field that is uniform in rotation angle and falls off in strength with increasing radius. In some implementations, such a field shape can be achieved regardless of the magnitude of the magnetic field.

As noted, in an example, the particle accelerator is a synchrocyclotron. Accordingly, the RF voltage is swept across a range of frequencies to account for relativistic effects on the particles (e.g., increasing particle mass) when accelerating particles within the acceleration cavity. The magnetic field produced by running current through the superconducting coils, together with the shape of the cavity, causes particles accelerated from the plasma column to accelerate orbitally within the cavity and to increase in energy with an increasing number of turns.

In the example synchrocyclotron, a magnetic field regenerator (not shown) is positioned near the outside of the cavity (e.g., at an interior edge thereof) to adjust the existing magnetic field inside the cavity to thereby change locations, such as the pitch and angle, of successive orbits of the particles accelerated from the plasma column so that, eventually, the particles output to an extraction channel that passes through the cryostat. The regenerator may increase the magnetic field at a point in the cavity (e.g., it may produce a magnetic field "bump" of about 2 Tesla or so at an area of the cavity), thereby causing each successive orbit of particles at that point to proceed outwardly toward the entry point of an extraction channel until the particles reach the extraction channel. The extraction channel receives, from the cavity, particles that have been accelerated within the cavity, and outputs the received particles from the cavity in a pulsed particle beam. The extraction channel may contain magnets and other structures to direct the particle beam out of the particle accelerator and towards a scanning or scattering system.

As noted, the superconducting coils (called the main coils) can produce relatively high magnetic fields. In an example implementation, the maximum magnetic field generated by a main coil (e.g., at the center of the acceleration cavity) may be within a range of 4 T to 20 T or more. For example, the superconducting coils may be used in generating magnetic fields at, or that exceed, one or more of the following magnitudes: 4.0 T, 4.1 T, 4.2 T, 4.3 T, 4.4 T, 4.5 T, 4.6 T, 4.7 T, 4.8 T, 4.9 T, 5.0 T, 5.1 T, 5.2 T, 5.3 T, 5.4 T, 5.5 T, 5.6 T, 5.7 T, 5.8 T, 5.9 T, 6.0 T, 6.1 T, 6.2 T, 6.3 T, 6.4 T, 6.5 T, 6.6 T, 6.7 T, 6.8 T, 6.9 T, 7.0 T, 7.1 T, 7.2 T, 7.3 T, 7.4 T, 7.5 T, 7.6 T, 7.7 T, 7.8 T, 7.9 T, 8.0 T, 8.1 T, 8.2 T, 8.3 T, 8.4 T, 8.5 T, 8.6 T, 8.7 T, 8.8 T, 8.9 T, 9.0 T, 9.1 T, 9.2 T, 9.3 T, 9.4 T, 9.5 T, 9.6 T, 9.7 T, 9.8 T, 9.9 T, 10.0 T, 10.1 T, 10.2 T, 10.3 T, 10.4 T, 10.5 T, 10.6 T, 10.7 T, 10.8 T, 10.9 T, 11.0 T, 11.1 T, 11.2 T, 11.3 T, 11.4 T, 11.5 T, 11.6 T, 11.7 T, 11.8 T, 11.9 T, 12.0 T, 12.1 T, 12.2 T, 12.3 T, 12.4 T, 12.5 T, 12.6 T, 12.7 T, 12.8 T, 12.9 T, 13.0 T, 13.1 T, 13.2 T, 13.3 T, 13.4 T, 13.5 T, 13.6 T, 13.7 T, 13.8 T, 13.9 T, 14.0 T, 14.1 T, 14.2 T, 14.3 T, 14.4 T, 14.5 T, 14.6 T, 14.7 T, 14.8 T, 14.9 T, 15.0 T, 15.1 T, 15.2 T, 15.3 T, 15.4 T, 15.5 T, 15.6 T, 15.7 T, 15.8 T, 15.9 T, 16.0 T, 16.1 T, 16.2 T, 16.3 T, 16.4 T, 16.5 T, 16.6 T, 16.7 T, 16.8 T, 16.9 T, 17.0 T, 17.1 T, 17.2 T, 17.3 T, 17.4 T, 17.5 T, 17.6 T, 17.7 T, 17.8 T, 17.9 T, 18.0 T, 18.1 T, 18.2 T, 18.3 T, 18.4 T, 18.5 T, 18.6 T, 18.7 T, 18.8 T, 18.9 T, 19.0 T, 19.1 T, 19.2 T, 19.3 T, 19.4 T, 19.5 T, 19.6 T, 19.7 T, 19.8 T, 19.9 T, 20.0 T, 20.1 T, 20.2 T, 20.3 T, 20.4 T, 20.5 T, 20.6 T, 20.7 T, 20.8 T, 20.9 T, or more. Furthermore, the superconducting coils may be used in generating magnetic fields that are outside the range of 4 T to 20 T or that are within the range of 4 T to 20 T but that are not specifically listed herein.

In some implementations, such as the implementations shown in FIG. 1, the relatively large ferromagnetic magnetic yokes 14, 15 act as returns for stray magnetic fields produced by the superconducting coils. In some systems, a magnetic shield (not shown) surrounds the yokes. The return yokes and the shield together act to reduce stray magnetic fields, thereby reducing the possibility that stray magnetic fields will adversely affect the operation of the particle accelerator.

In some implementations, the return yokes and shield may be replaced by, or augmented by, an active return system. An example active return system includes one or more active return coils that conduct current in a direction opposite to current through the main superconducting coils. In some example implementations, there is an active return coil for each superconducting main coil, e.g., two active return coils—one for each main superconducting coil. Each active return coil may also be a superconducting coil that surrounds the outside of a corresponding main superconducting coil concentrically.

As noted, current passes through the active return coils in a direction that is opposite to the direction of current passing through the main coils. The current passing through the active return coils thus generates a magnetic field that is opposite in polarity to the magnetic field generated by the main coils. As a result, the magnetic field generated by an active return coil is able to reduce at least some of the relatively strong stray magnetic field resulting from a corresponding main coil.

By using an active return system, the relatively large ferromagnetic magnetic yokes 14, 15 can be replaced with magnetic pole pieces that are smaller and lighter. Accordingly, the size and weight of the synchrocyclotron can be reduced further without sacrificing performance. An example of an active return system that may be used is described in U.S. Pat. No. 8,791,656 entitled "Active Return System", the contents of which are incorporated herein by reference.

At or near the output of the extraction channel of the particle accelerator, there may be one or more beam shaping elements, such as a scanning system and/or a scattering system. Components of these systems may be mounted on, or otherwise attached to, the nozzle for positioning relatively close to the patient during treatment. In some implementations, however, beam spreader(s) may be mounted closer to (e.g., on) the accelerator or the outer gantry itself (e.g., mounted to the outer gantry in the absence of an accelerator mounted there).

Figure 2:
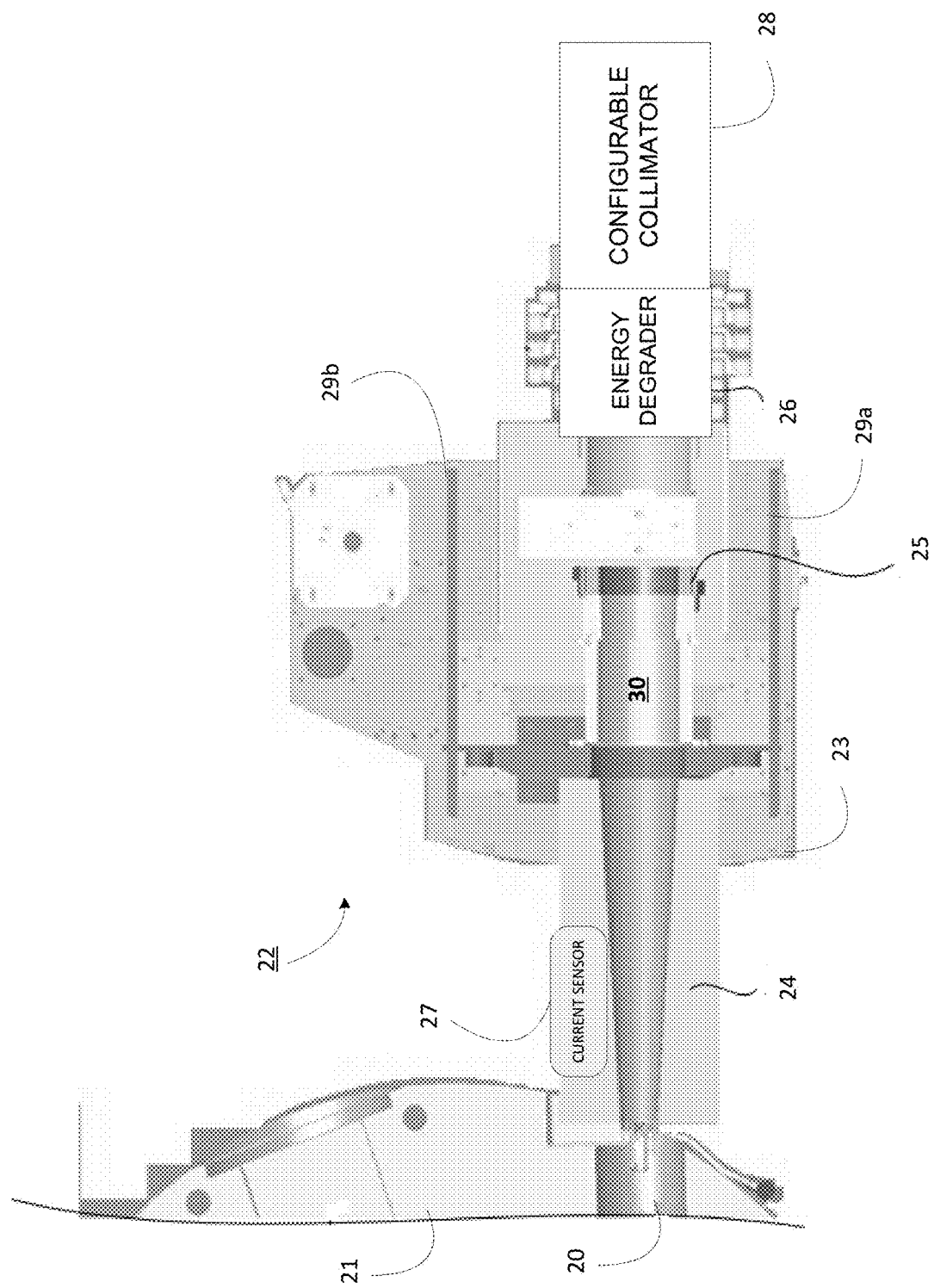
FIG. 2 is a side view of example components that may be used to implement scanning in the particle therapy system.
Figure 3:
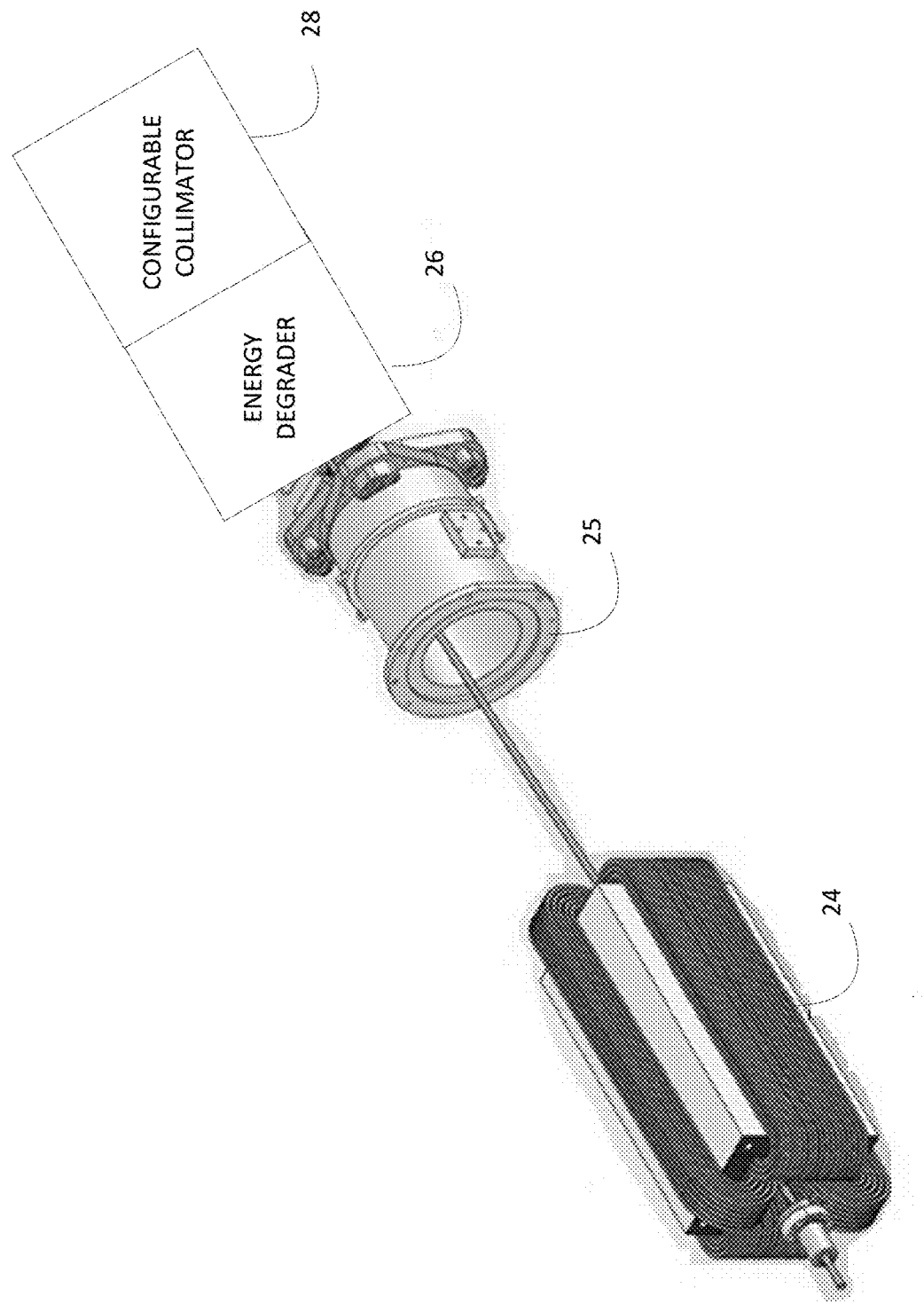
FIG. 3 is a perspective view of example components that may be used to implement scanning in the particle therapy system.

Referring to FIG. 2, in an example implementation, at the output of extraction channel 20 of synchrocyclotron 21 (which may have the configuration of FIG. 1) are example scanning components 22 that may be used to scan the particle beam across all or part of an irradiation target. FIG. 3 also shows examples of the components of FIG. 2. These include, but are not limited to, a scanning magnet(s) 24, an ion chamber 25, an energy degrader 26, and a configurable collimator 28. Other components that may be down-beam of the extraction channel are not shown in FIG. 2 or 3, including, e.g., one or more scatterers for changing beam spot size.

In an example operation, scanning magnet 24 is an example beam spreader, and is controllable in two dimensions (e.g., Cartesian XY dimensions) to position the particle beam in those two dimensions, and to move the particle beam across at least a part (e.g., a cross-section) of an irradiation target. Ion chamber 25 detects the dosage of the beam and feeds-back that information to a control system to adjust beam movement. Energy degrader 26 is controllable to move material (e.g., one or more individual plates) into, and out of, the path of the particle beam to change the energy of the particle beam and therefore the depth to which the particle beam will penetrate the irradiation target. In this way, the energy degrader can position the particle beam at a depth-wise layer of an irradiation target, e.g., to the layer. In some implementations, the energy degrader uses wedges or other types of structures instead of, or in addition to, plates. For example, energy degrader 26 may be controllable to move material (e.g., one or more individual wedges) into, and out of, the path of the particle beam to change the energy of the particle beam and therefore the depth to which the particle beam will penetrate the irradiation target.

In some implementations, there may be different energy degraders having different sizes, e.g., plates or wedges having different areas. In some implementations, the control system described herein may swap, in and out of the beam field, differently-sized energy degraders based on the beam field size.

Figure 5:
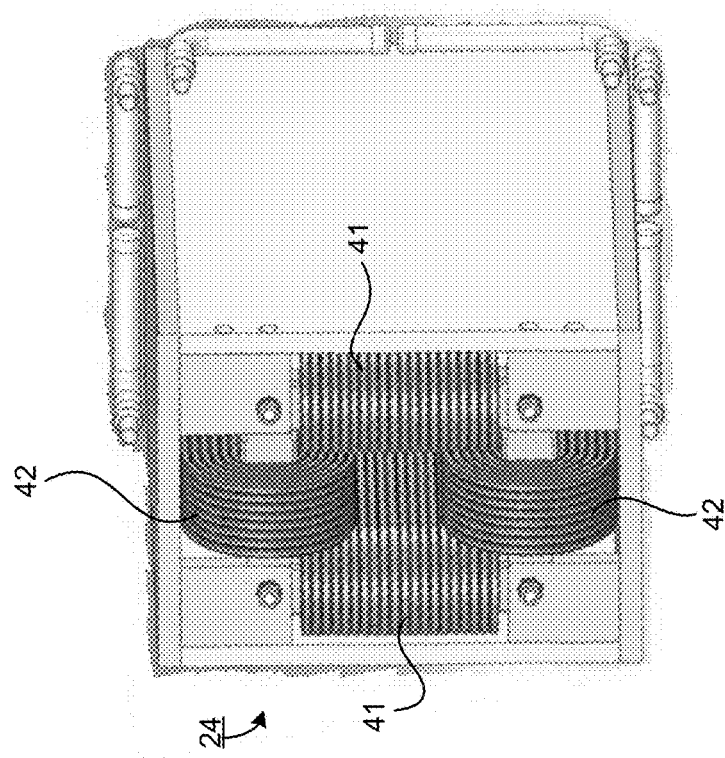
FIG. 5 is a perspective view of an example scanning magnet that may be part of the scanning components.
Figure 4:
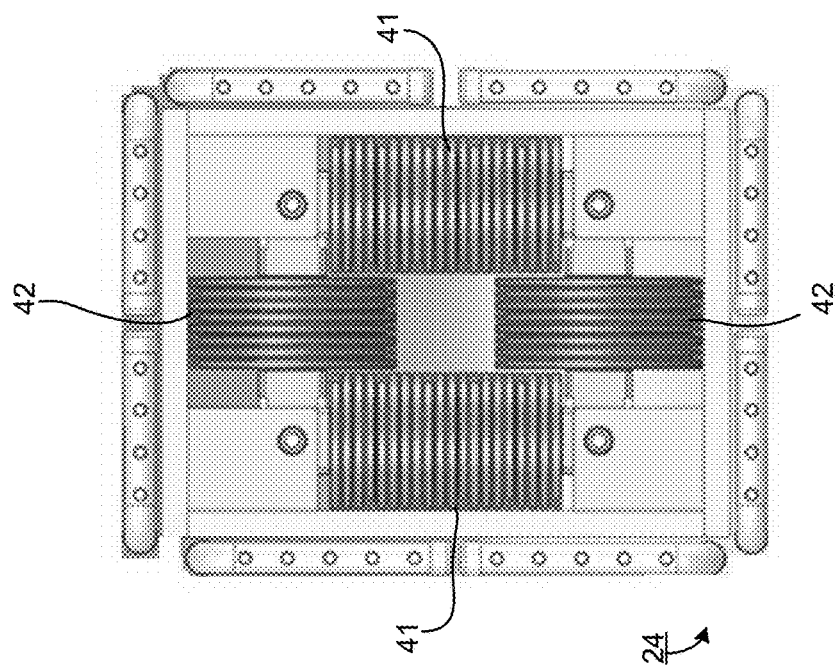
FIG. 4 is a side view of an example scanning magnet that may be part of the scanning components.

FIGS. 4 and 5 show views of an example scanning magnet 24. In this example implementation, scanning magnet 24 includes two coils 41, which control particle beam movement in the X direction, and two coils 42, which control particle beam movement in the Y direction. Control is achieved, in some implementations, by varying current through one or both sets of coils to thereby vary the magnetic field(s) produced thereby. By varying the magnetic field(s) appropriately, the particle beam can be moved in the X and/or Y direction across the irradiation target. The scanning magnet(s) may be leveraged to control the location and/or direction of the particle beam in the automated treatment process described herein.

In some implementations, the scanning magnet is not movable physically relative to the particle accelerator. In some implementations, the scanning magnet may be movable physically relative to the particle accelerator (e.g., in addition to the movement provided by the gantry). In some implementations, the scanning magnet may be controllable to move the particle beam continuously so that there is uninterrupted motion of the particle beam over at least part of, and possibly all of, a layer of an irradiation target being scanned. In some implementations, the scanning magnets are controllable at intervals or specific times. In some implementations, there may be two or more different scanning magnets to position the particle beam, and to control all or part movement of a particle beam in the X and/or Y directions during scanning. In some implementations, scanning magnet 24 may have an air core, a ferromagnetic (e.g., an iron) core, or a core that is a combination of air and ferromagnetic material.

Referring back to FIG. 2, a current sensor 27 may be connected to, or be otherwise associated with, scanning magnet 24. For example, the current sensor may be in communication with, but not connected to, the scanning magnet. In some implementations, the current sensor samples current applied to the magnet, which may include current to the coil(s) for controlling beam scanning in the X direction and/or current to the coil(s) for controlling beam scanning in the Y direction. The current sensor may sample current through the magnet at times that correspond to the occurrence of pulses in the particle beam or at a rate that exceeds the rate that the pulses occur in the particle beam. In the latter case, the samples, which identify the magnet current, are correlated to detection of the pulses by the ion chamber described below. For example, the times at which pulses are detected using the ion chamber may be correlated in time to samples from the current sensor, thereby identifying the current in the magnet coil(s) at the times of the pulses. Using the magnet current, it thus may be possible to determine the location on the irradiation target (e.g., on a depth-wise layer of the irradiation target) where each pulse, and thus dose of particles, was delivered. The location of the depth-wise layer may be determined based on the configuration of the energy degrader (e.g., the number of plates) in the beam path.

During operation, the magnitude(s) (e.g., value(s)) of the magnet current(s)) may be stored for each location at which a dose is delivered, along with the amount (e.g., intensity) of the dose. A computer system, which may be either on the accelerator or remote from the accelerator and which may include memory and one or more processing devices, may correlate the magnet current to coordinates within the radiation target, and those coordinates may be stored along with the amount of the dose. For example, the location may be identified by depth-wise layer number and Cartesian XY coordinates or by Cartesian XYZ coordinates (with the depth-wise layer corresponding to the Z coordinate). In some implementations, both the magnitude of the magnet current and the coordinate locations may be stored along with the dose at each location. The foregoing information may be stored in memory either on, or remote from, the accelerator. This information may be used during scanning to apply multiple doses of the same or of different amounts to the same locations to achieve target cumulative doses, including at areas of overlap between adjacent/sequential beam fields, as described herein.

In some implementations, ion chamber 25 detects dosage (e.g., one or more individual doses) applied by the particle beam to positions on an irradiation target by detecting the numbers of ion pairs created within a gas caused by incident radiation. The numbers of ion pairs correspond to the dose provided by the particle beam. That information is fed-back to the computer system and stored in memory along with the time that the dose is provided. This information may be correlated to, and stored in association with, the location at which the dose was provided and/or the magnitude of the magnet current at that time, as described above.

In some implementations, the scanning system is run open loop, in which case, by controlling the scanning magnet(s), the particle beam is moved freely and uninterrupted across an irradiation target so as to substantially cover the target with radiation. As the radiation is delivered, the dosimetry controlled by the particle therapy control system records (e.g., stores) the amount of the radiation per location and information corresponding to the location at which the radiation was delivered. The location at which the radiation was delivered may be recorded as coordinates or as one or more magnet current values, and the amount of the radiation that was delivered may be recorded as dosage in grays. Because the system is run open loop, the delivery of the radiation is not synchronized to the operation of the particle accelerator (e.g., to its radio frequency (RF) cycle). Locations on the target where insufficient dose has been deposited can be treated with the particle beam any appropriate number of times until a desired dosage is reached. Different treatments of the same location may be from the same beam angle (e.g., from the same projection/beam field) or from different beam angles (projections/beam fields) as is the case intensity-modulated proton therapy (IMPT) described herein.

Configurable collimator 28 may be located down-beam of the scanning magnets and down-beam of the energy degrader, as shown in FIGS. 2 and 3. The configurable collimator may trim the particle beam on a spot-by-spot basis during movement of the particle beam during scanning. For example, the configurable collimator may include sets of leaves that face each other, and that are movable into and out of carriages to create an aperture shape. Parts of the particle beam that exceed the aperture shape are blocked, and do not pass to the patient. The parts of the beam that pass to the patient are at least partly collimated, thereby providing a beam with a relatively precise edge. In an example, each set of leaves in the configurable collimator is controllable to define an edge that is movable into a path of the particle beam such that a first part of the particle beam on a first side of the edge is blocked by the multiple leaves and such that a second part of the particle beam on a second side of the edge is not blocked by the multiple leaves. The leaves in each set are individually controllable during scanning to trim an area as small as a single spot, and can also be used to trim larger multi-spot areas.

Figure 6:
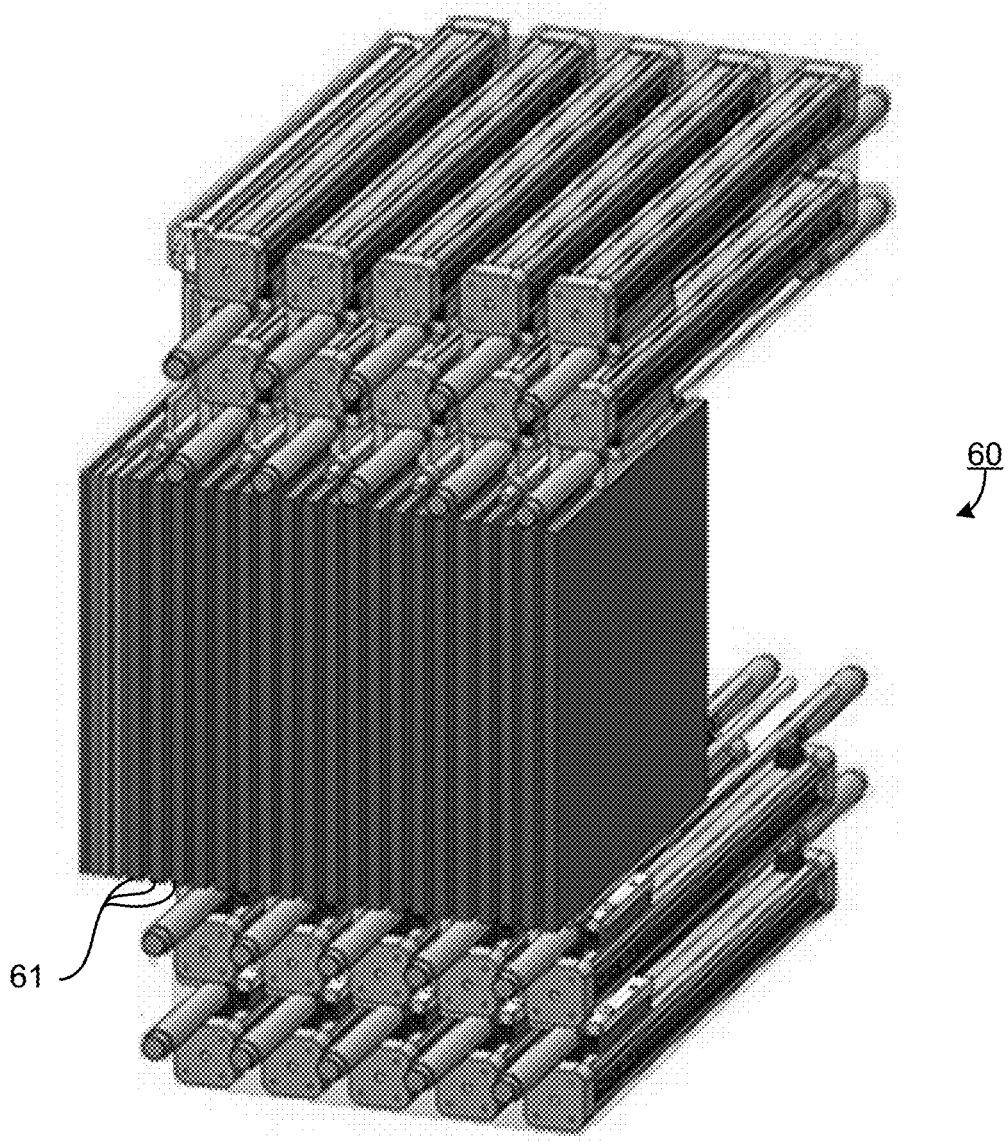
FIG. 6 is a perspective view of an example range modulator, which is a type of energy degrader that may be part of the scanning components.

FIG. 6 shows a range modulator 60, which is an example implementation of energy degrader 26. In some implementations, range modulator 60 may be located down-beam of the scanning magnets between the configurable collimator and the patient. In some implementations, such as that shown in FIG. 6, the range modulator includes a series of plates 61. The plates may be made of one or more of the following example materials: polycarbonate, carbon, beryllium or other material of low atomic number. Other materials, however, may be used in place of, or in addition to, these example materials.

One or more of the plates is movable into, or out of, the beam path to thereby affect the energy of the particle beam and, thus, the depth of penetration of the particle beam within the irradiation target. That is, each plate allows the beam to pass but, as a result of passing through the plate, the energy of the beam is decreased by an amount that is based on the geometry (e.g., thickness) and the composition (e.g., material) of the plate. In an example, the more plates that are moved into the path of the particle beam, the more energy that will be absorbed by the plates, and the less energy the particle beam will have. Conversely, the fewer plates that are moved into the path of the particle beam, the less energy that will be absorbed by the plates, and the more energy the particle beam will have. Higher energy particle beams typically penetrate deeper into the irradiation target than do lower energy particle beams. In this context, "higher" and "lower" are meant as relative terms, and do not have any specific numeric connotations.

Figure 7:
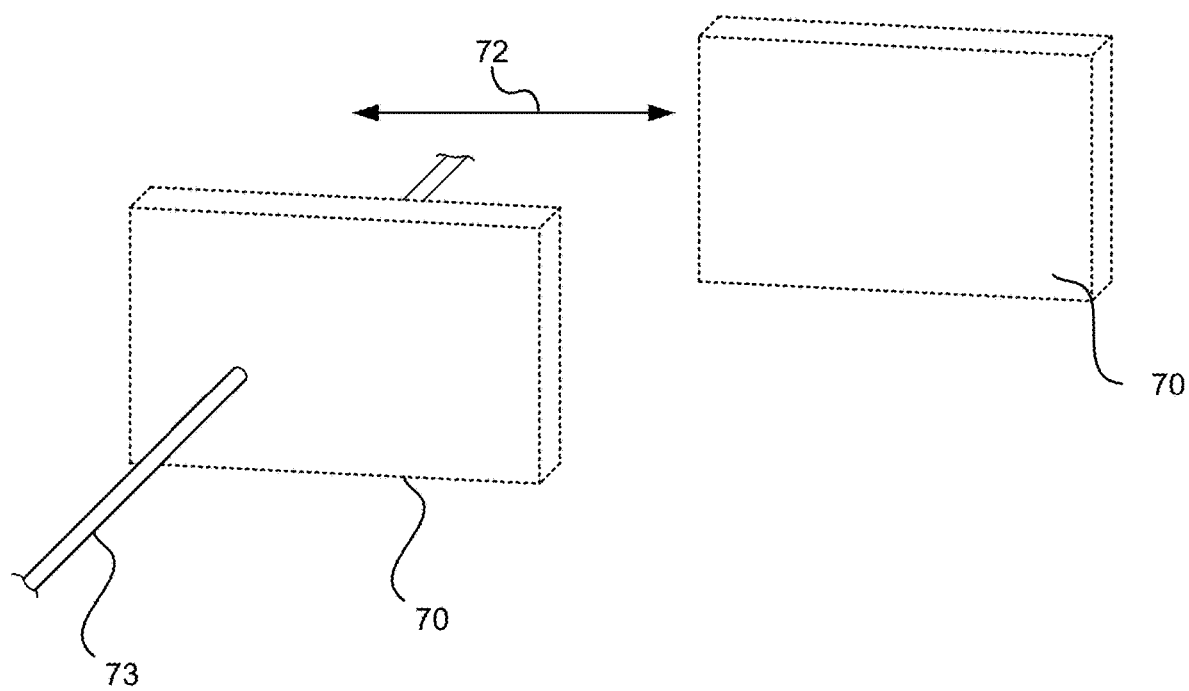
FIG. 7 is a perspective view showing an example of movement of plates that may be implemented in the range modulator.

Plates are moved physically into, and out of, the path of the particle beam. For example, as shown in FIG. 7, a plate 70 moves along the direction of arrow 72 between positions in the path of the particle beam 73 and outside the path of the particle beam. The plates are computer-controlled. Generally, the number of plates that are moved into the path of the particle beam corresponds to the depth at which scanning of an irradiation target is to take place. Thus, the particle beam can be positioned into the interior of a target by appropriate control of the plates.

By way of example, the irradiation target can be divided into cross-sections or depth-wise layers, each of which corresponds to an irradiation depth. One or more plates of the range modulator can be moved into, or out of, the beam path to the irradiation target in order to achieve the appropriate energy to irradiate each of these cross-sections or depth-wise layers of the irradiation target. The range modulator may be stationary relative to the particle beam during scanning of a part of (e.g., cross-section of) an irradiation target or the plates of the range modulator may move during scanning. For example, the particle beam may track movement of one or more plates into, or out of, the beam field (also called the irradiation field) during the scanning process.

Referring back FIG. 2, assembly 30, which includes, e.g., the ion chamber, the energy degrader, and the configurable collimator, may be mounted, or otherwise coupled, to carriage 23. In some implementations, carriage 23 is mounted to one or more tracks—in this example, to two tracks 29a, 29b—for movement relative to the irradiation target. In some examples, the carriage may be part of, or mounted to, the nozzle, thereby enabling some components of the scanning system to be moved towards, or away from, the patient. In some implementations, carriage 23 may be mounted using different mechanisms or in a different configuration for movement relative to the irradiation target. Movement may be along the beam line, e.g., along a path of the particle beam. This movement enables additional control over positioning of the particle beam—and thus an additional degree of freedom—to support treatment across, and irrespective of, beam fields and any isocenters.

Movement also will allow these components to be moved away from a patient on the treatment couch to allow the nozzle and/or patient to be moved automatically for the next projection/beam field to be treated. Then, the nozzle can be moved back toward the patient for the next beam field.

Moving the collimator and energy degrader towards, or away from, the irradiation target affects the distance that the particle beam travels through the air and, thus, the size of a spot of the particle beam in the irradiation target. That is, passage through air can cause the beam spot size to increase. Accordingly, moving the carriage away from the irradiation target increases the distance that the particle beam travels through the air, thus increasing the spot size. Conversely, moving the carriage towards the irradiation target decrease the distance that the particle beam travels through the air, thus decreasing the spot size. In some implementations, carriage 23 is controllable to move in coordination with movement of the gantry and/or the treatment couch as described herein to position the particle beam for treatment, and to implement treatment in close proximity to the patient.

Some components of the scanning system, including the energy degrader and the configurable collimator, may be mounted on, or coupled to, a nozzle 81 of the particle therapy system's inner gantry 80 (see FIG. 8), and may be controlled by a control system, such as one or more computing devices (see, e.g., FIG. 14) that also controls operation of other components of the particle therapy system. FIG. 9 shows another implementation of a particle therapy system having an inner gantry 90 with a nozzle 91 on which some components of the scanning system, including the energy degrader and the configurable collimator (but, in some cases, not the scanning magnet(s)), may be mounted. In both examples, the nozzle is movable along a track of the inner gantry (80 or 90) relative to the patient and the particle accelerator, and is extensible towards, and retractable away from, the patient, thereby also extending and retracting the components mounted thereon.

Operation of the range modulator may be coordinated with, and controlled with, operation of other scanning components, the particle accelerator, and the gantries described herein to implement automated particle therapy treatment and variations thereof. For example, the range modulator may be used to position the particle beam in a depth-wise (e.g., Cartesian Z) dimension relative to an irradiation target, and other scanning components, such as the beam spreader—e.g., the scanning magnet(s), may be used to position the particle beam in two other dimensions relative to the irradiation target that are orthogonal to the depth-wise dimension (e.g., the Cartesian X,Y dimensions). Positioning using the scanning components and other movable parts of the system supports automated, multiple-field treatment particle therapy that may or may not be isocentric. In cases where a variable-energy synchrocyclotron is used, control over beam energy, and thus beam depth-wise position, may be implemented in the accelerator itself.

As noted, the particle beam passes from the range modulator, through the configurable collimator, to the patient. Passage through air can cause the beam spot size to increase. The longer that the beam passes through air, the greater this spot size increase may be. Accordingly, in some implementations, it is advantageous to reduce the maximum distance that the beam can pass through the air. As explained above, in some examples, the components mounted on the nozzle closest to the patient (e.g., a collimator and energy degrader) may reduce the amount that the beam passes through the air. However, in some examples, because of their proximity to the patient, those components may be made relatively small. The size of those components is related to the treatable field size. That is, these smaller components may result in a relatively smaller beam field size.

Figure 10:
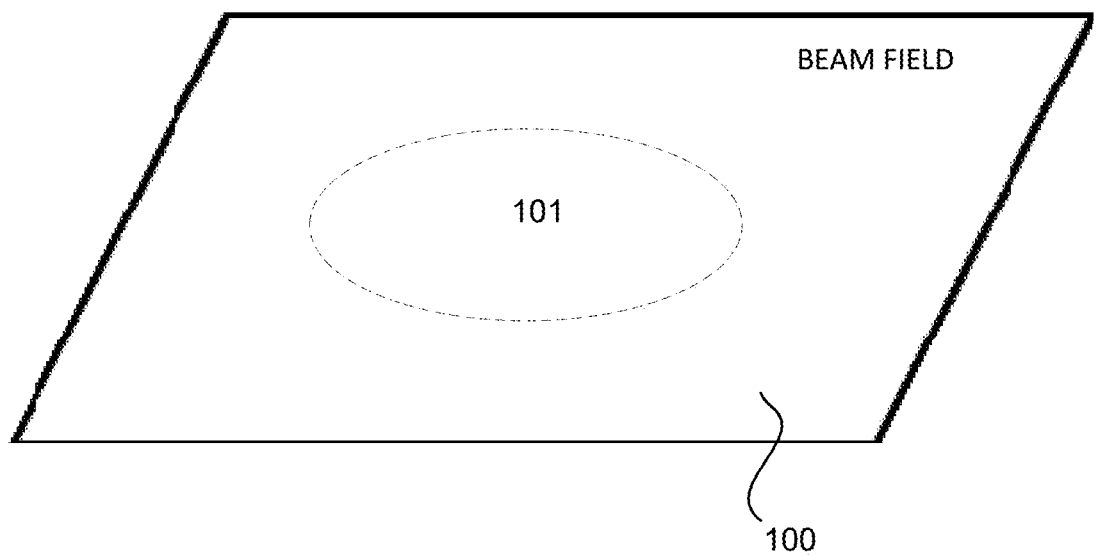
FIG. 10 is a conceptualized perspective view of a beam field.

As described, the beam field (also called the irradiation field) is based on a projection of radiation from a beam spreader. A beam field may be represented conceptually by a plane that defines the maximum extent or range that a projection of a particle beam can move in the X and Y directions relative to the irradiation target. For example, FIG. 10 shows a beam field 100 in front of an irradiation target 101. The target is depicted in dashed lines to indicate that it is behind the beam field. Although a rectangular plane is shown, the beam field may have any appropriate shape. Due to physical system limitations, the particle beam produced by the synchrocyclotron is movable across, but not beyond, the borders of the beam field. As noted, reduced size of the nozzle enables the reduction in the air gap, but also may make the beam field smaller due to the presence of smaller components.

In some situations, the beam field may be smaller than the irradiation target to be treated (which is not the case in FIG. 10, but see, e.g., FIGS. 15 and 16 described below). Accordingly, in some examples, the processes described herein automate movement of components of the particle therapy system in order to treat the entire irradiation target using multiple beam fields without requiring manual accelerator reconfiguration, manual spreader reconfiguration, and/or manual patient repositioning. Treatment near the boundaries using two or more beam fields may be computer-controlled based on instructions received from a TPS using beam fields near the boundaries. Such treatment may also be independent of any isocenter location(s). Example implementations are described in more detail below.

Figure 8:
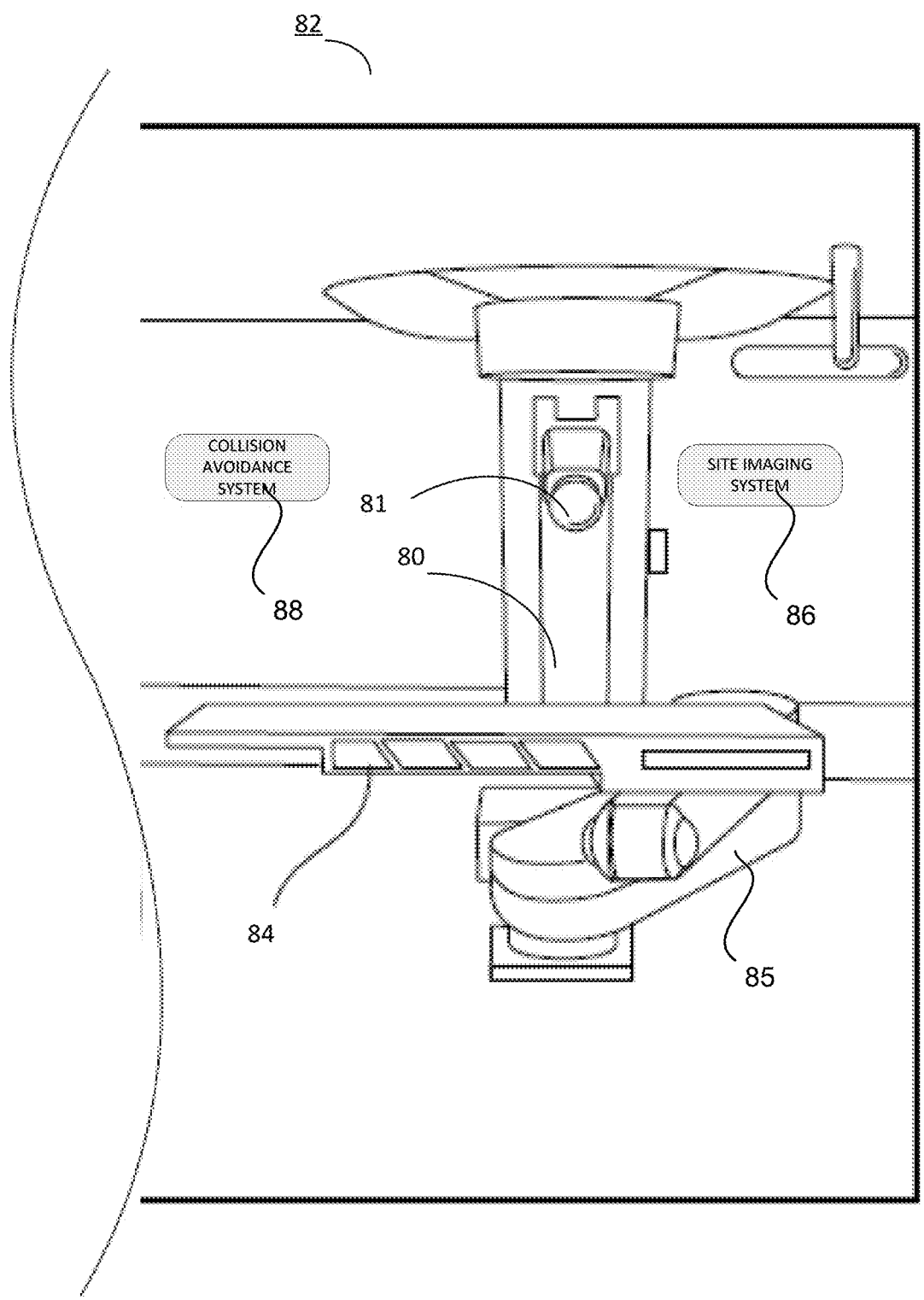
FIG. 8 is a front view of components of an example implementation of a particle therapy system from the perspective of a treatment space.
Figure 9:
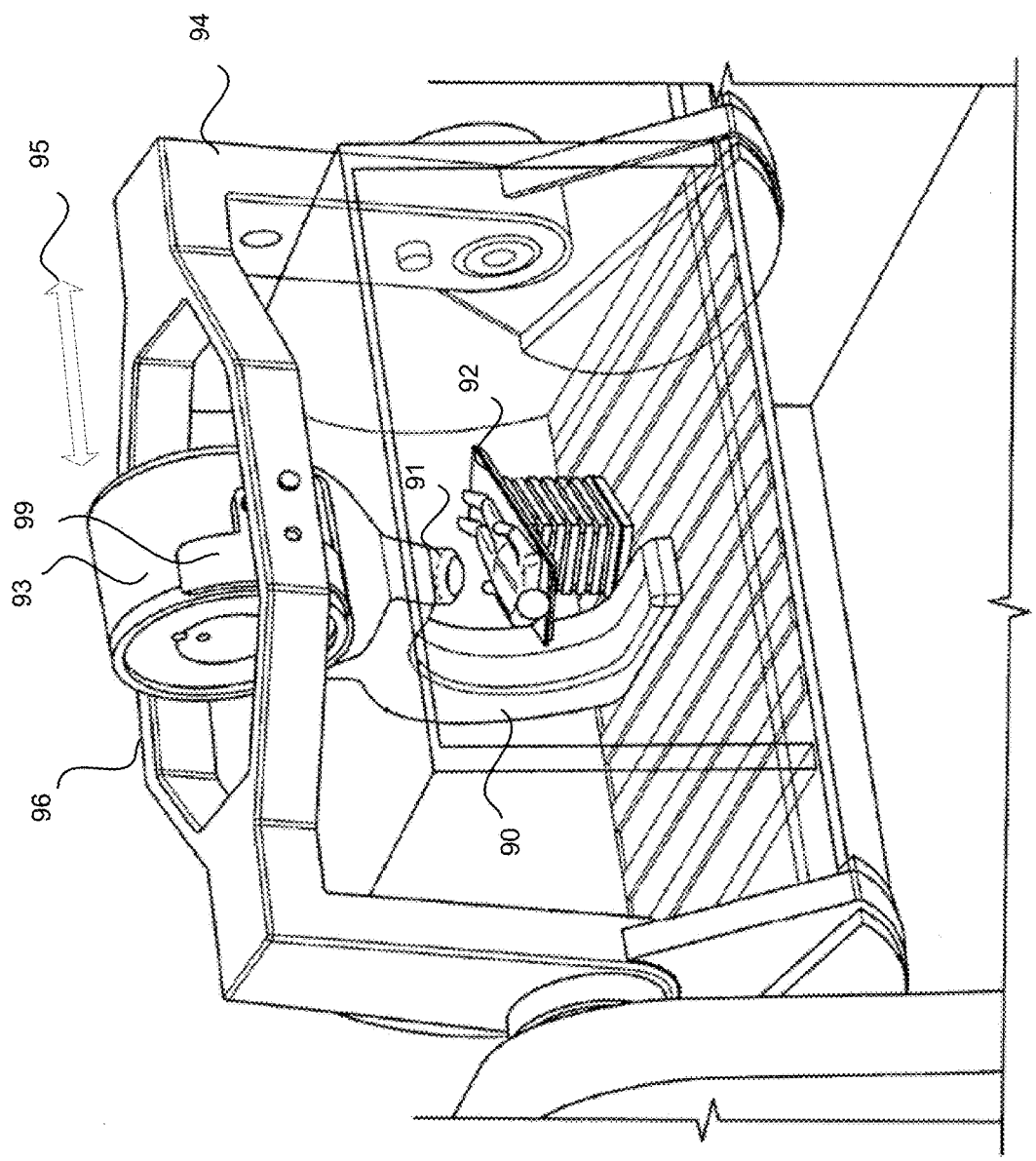
FIG. 9 is a perspective view of components of another example implementation of a particle therapy system.
Figure 11:
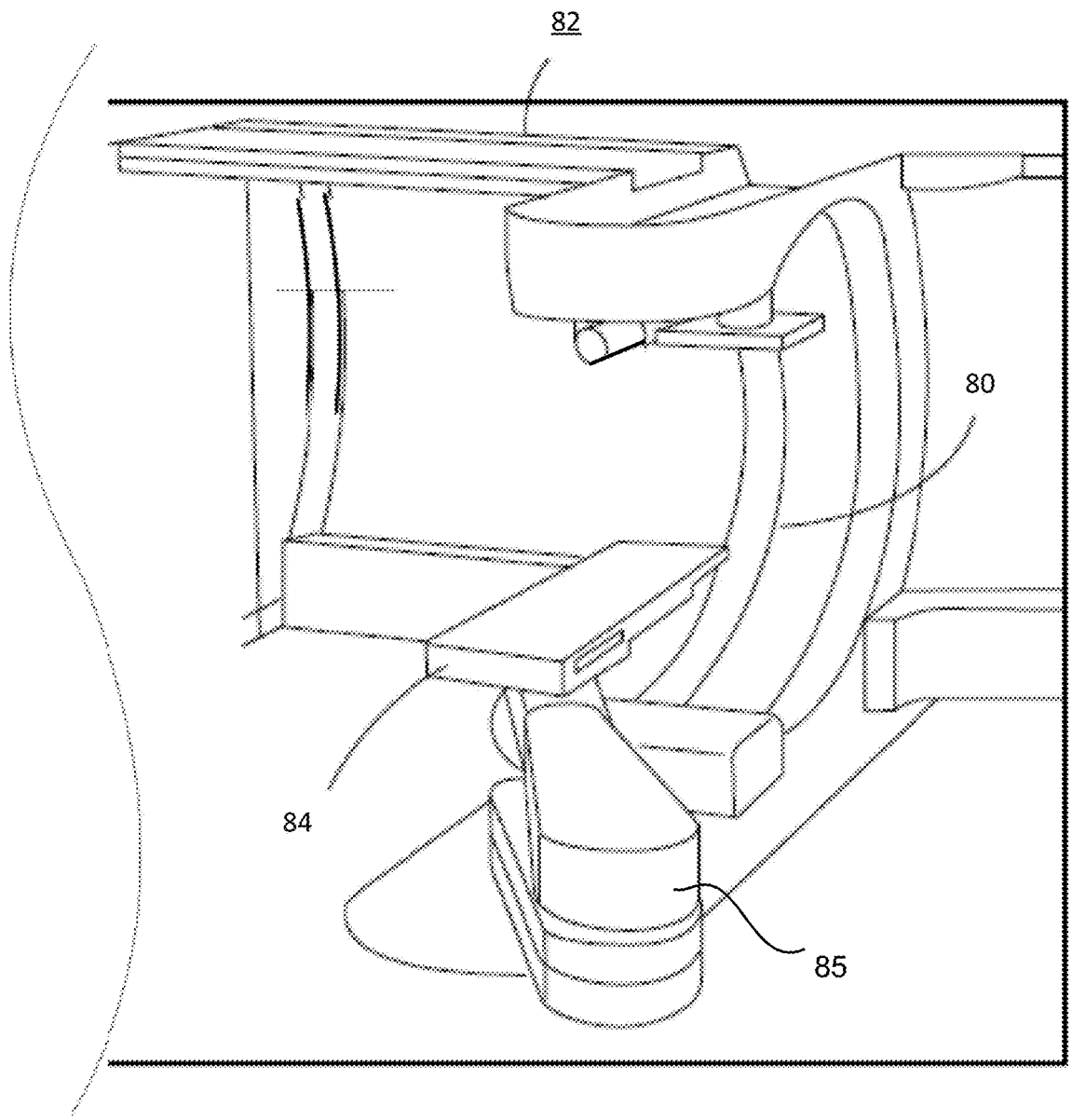
FIG. 11 is a perspective view of components of the particle therapy system of FIG. 8 from the perspective of a treatment space.

FIGS. 8 and 11 show parts an example of a particle therapy system 82 containing a particle accelerator mounted on a gantry—in this example, a superconducting synchrocyclotron having a configuration described herein is used. In some implementations, the gantry is steel and has two legs (not shown) mounted for rotation on two respective bearings that lie on opposite sides of a patient. The gantry may include a steel truss, connected to each of its legs, that is long enough to span a treatment area in which the patient lies and that is attached at both ends to the rotating legs of the gantry. The particle accelerator may be supported by the steel truss. An example of a gantry configuration that may be used is described in U.S. Pat. No. 7,728,311 entitled "Charged Particle Radiation Therapy", the contents of which are incorporated herein by reference.

FIG. 9 shows an example of the gantry configuration described in U.S. Pat. No. 7,728,311, and includes components of an alternative implementation of a particle therapy system that is controllable in the manner described herein to produce automated treatment. The example particle therapy system of FIG. 9 includes an inner gantry 90 having a nozzle 91, a treatment couch 92, and a particle accelerator 93 (e.g., a synchrocyclotron of the type described herein) mounted on an outer gantry 94 for rotation at least part-way around the patient to deliver radiation to target(s) in the patient. Treatment couch 92 is controllable and configured to rotate and to translate the patient in the manner described herein.

In the example of FIG. 9, particle accelerator is also mounted to outer gantry 94 also to enable linear movement (e.g., translational movement) of the particle accelerator in the directions of arrow 95 along arms 96. Thus, the accelerator is movable, relative to the treatment couch and thus the patient, from a first location along arms 96, to a second location along arms 96, to a third location along arms 96, and so forth in order to position the accelerator, and thus the beam, for treatment. This translational movement may be controlled by the control system described herein, and used as an additional degree of freedom for positioning the particle beam in the automated particle therapy system described herein. Although single-dimensional translational movement (along arrow 95) is shown in FIG. 9, the particle therapy system may be configured for two-dimensional translational movement, and/or three dimensional-translational movement as well (e.g., along the X, Y, and Z directions of a Cartesian coordinate system).

As also shown in FIG. 9, the particle accelerator 93 may be connected to a gimbal 99 for pivoting motion relative to the gantry. This pivoting motion may be used to position the accelerator, and thus the beam, for treatment. This pivoting movement may be controlled by the control system described herein, and may be used as one or more additional degrees of freedom for positioning the particle beam in the automated particle therapy system described herein. In some implementations, pivoting may enable the accelerator to move from a first orientation, to a second orientation, to a third orientation, and so forth during automated treatment. The particle accelerator may be mounted to enable pivoting relative to the patient in one, two, and/or three dimensions.

As described herein, in some implementations, rather than mounting the entire particle accelerator to the outer gantry (or other device), the spreader alone may be mounted in lieu of, or in addition to, the accelerator, and the spreader alone or in combination with the accelerator may be moved relative to the irradiation target. In cases where the spreader is mounted alone, the spreader may be moved in the same way as the accelerators described herein, e.g., linearly (translation), rotationally, and/or pivotally. Control over beam positioning may be implemented as described herein by controlling movement of the spreader mounted thereon in the manner described herein.

The example particle therapy system implementations shown in FIGS. 8 and 11 may also mount the particle accelerator so that the particle accelerator is capable of translational motion in one, two, and/or three dimensions relative to the patient. The example particle therapy system implementations shown in FIGS. 8 and 11 may also mount the particle accelerator so that the particle accelerator is capable of pivoting relative to the patient in one, two, and/or three dimensions.

In the example of FIGS. 8 and 11, the patient is located on a treatment couch 84. In this example, treatment couch 84 includes a platform that supports the patient. The platform also may include one or more restraints (not shown) for holding the patient in place and for keeping the patient substantially immobile during movement of the couch and during treatment. The platform may, or may not, be padded and/or have a shape (e.g., an indentation) that corresponds to the shape of part of the patient. For example, prior to treatment, the patient may be placed in a mold that conforms to the contours of the back half of the patient, and the resulting molded structure may be incorporated into the platform of the treatment couch. A mold, such as this, may reduce patient motion during movement of the treatment couch including, but not limited to, during treatment.

The treatment couch may include a movement mechanism to move the treatment couch automatically from one position in the treatment space (e.g., the proton center where particle therapy treatment is performed) to another position in the treatment space. The different positions may be different rotational positions, different physical locations (e.g., a translational movement from one physical location to another physical location), or a combination of rotational and translational positions. For example, the movement mechanism may include a robotic arm 85 that is controllable to move the couch in six degrees of freedom.

Movement of the treatment couch is automated and occurs while the patient remains in place on the couch. For example, the treatment couch, with the patient thereon, may be moved between different treatment positions. In some implementations, the patient does not move off of the treatment couch during movement between treatment positions. For example, the patient may be situated on the treatment couch prior to treatment; the couch may be moved into a first position for treatment of a first part of the patient; the patient may be treated at the first position; the couch may be moved to a second, different position for treatment of a second, different part of the patient while the patient remains situated on the couch; the patient may be treated at the second position; the couch may be moved to a third, still different position for treatment of a third, still different part of the patient while the patient remains situated on the couch; and so forth until treatment ends. Any appropriate number of couch movements and treatments may be implemented, all while the patient remains on the treatment couch and, in some cases, without human intervention. The different "parts" of the patient to be treated may be, for example, different tumors, different areas of one tumor, or the same areas of one tumor, and may be treated from different angles as is the case during intensity-modulated proton therapy. ("IMPT").

Figure 12:
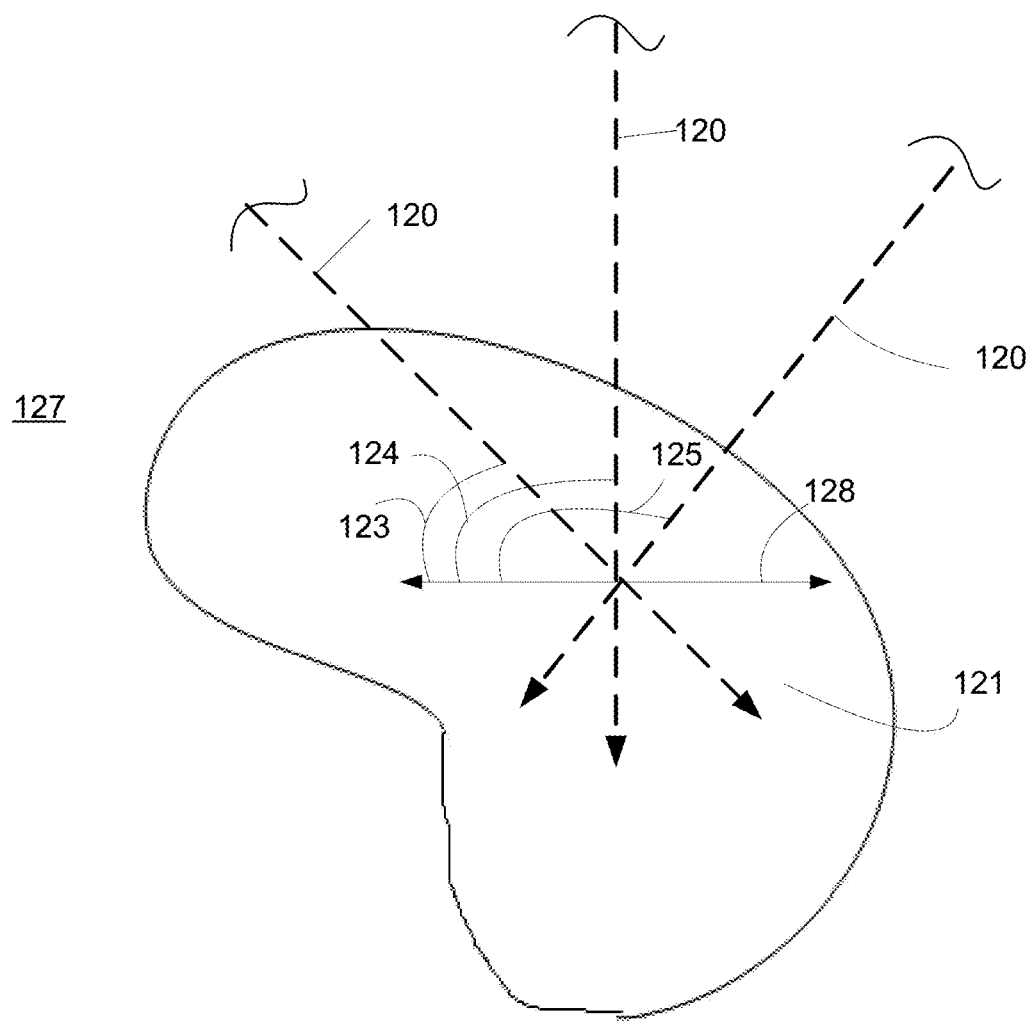
FIG. 12 is a diagram showing a particle beam hitting an irradiation target from different angles during intensity-modulated proton therapy (IMPT).

In this regard, during IMPT, the particle beam is projected at the irradiation target from different directions so that a percentage of the overall dose is delivered from each direction. As a result, the amount of dose delivered to volumes outside of the irradiation target can be reduced. For example, FIG. 12 shows a particle beam 120 applied to the irradiation target 121 from three different angles. In this example, dosage is cumulative, so ⅓ of the total dose may be applied from one angle; ⅓ of the total dose may be applied from another angle; and ⅓ of the total dose may be applied from yet another angle. That is, the particle beam may be scanned at angle 123 across a portion of a beam field in a plane angled relative to horizontal 128 to apply ⅓ of the dose; the particle beam may be scanned at angle 124 across a portion of a beam field in another plane angled relative to horizontal 128 to apply ⅓ of the dose; and the particle beam may be scanned at angle 125 across a portion of a beam field in still another plane angled relative to horizontal 128 to apply ⅓ of the dose. As a result, the amount of radiation applied to surrounding tissue 127 is spread out at the appropriate angles, thereby reducing the chances that surrounding tissue will be exposed to harmful amounts of radiation. Even though only three are shown, any appropriate number of angles and appropriate dosage per angle may be employed.

Referring to FIGS. 8, 9, and 11, the inner gantry may be configured to move relative to the treatment couch to direct output of the beam toward the patient. In these examples, the inner gantry is C-shaped, and its movement coincides with movement of the "outer" gantry, on which the synchrocyclotron is mounted. As explained, the inner gantry includes a nozzle, on which one or more beamline components (e.g., the range modulator and configurable collimator) are mounted to shape and otherwise adjust the beam. In some implementations, the inner gantry supports sub-millimeter beam positioning. In some implementations, there is no inner gantry, and all components described herein as being mounted on the inner gantry may be mounted to the accelerator or to the outer gantry.

Figure 13:
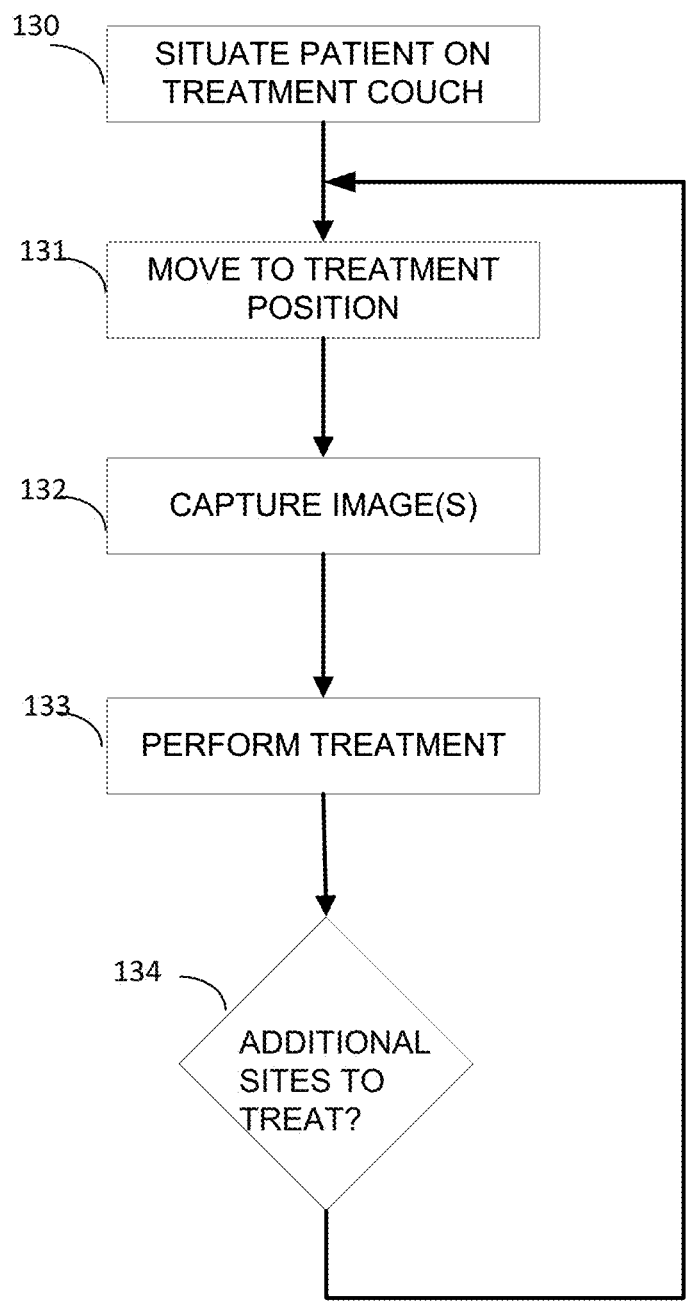
FIG. 13 is a flowchart showing an example process for automating treatment of a patient using a particle therapy system.

In some implementations, some or all movement of the treatment couch occurs while the patient remains in place on the couch. As explained, the treatment couch, with the patient thereon, may be moved automatically between treatment positions. In some implementations, the particle therapy system captures images of the patient between treatments in order to direct the treatment to the appropriate locations within the patient. In some implementations, these images are captured while the patient is on the treatment couch. For example, referring to the process of FIG. 13, the patient may be situated (130) on the treatment couch prior to treatment; the couch may be moved (131) into a first position for treatment of the irradiation target or a portion of the irradiation target within the patient with a first beam field; images of the patient at the first position may be captured (132) while the patient is on the treatment couch; and the patient may be treated (133) at the first position based on the images. If additional treatments are to be performed (134), the couch may be moved to a second, different position for treatment of the irradiation target or a portion thereof with a second beam field while the patient remains situated on the couch; images of the patient at the second position may be captured while the patient is on the treatment couch; the patient may be treated at the second position based on the captured images; the couch may be moved to a third, still different position for treatment of the irradiation target or a portion thereof with a third beam field while the patient remains situated on the couch; images of the patient at the third position may be captured while the patient is on the treatment couch; the patient may be treated at the third position based on the captured images; and so forth until treatment ends. In some implementations, a sequencing that is different than that presented above may be employed or different patient position tracking techniques than those described may be used. In some implementations, imaging following each treatment is not required.

In some implementations, the particle therapy system is configured to determine the location of an irradiation target, such as a tumor. The initial location and mapping of the irradiation target (e.g., the tumor) may be obtained in a pre-treatment imaging operation, which may occur inside or outside the proton center. In some implementations, the patient may remain on the couch from initial imaging through treatment, including repositioning during treatment, as explained with respect to FIG. 13. Furthermore, in some implementations, the entire process, from initial imaging to final treatment, is automated, eliminating or, at least, reducing the need for human intervention.

In some implementations, the pre-treatment imaging operation may be performed using an imaging system, such as a three-dimensional (3D) imaging system. In some implementations, the 3D imaging system is a computed tomography (CT) system; however, in other implementations, different types of imaging systems may be used instead of, or in addition to, a CT system. In operation, images may be captured at different points in time in order to enable tracking of movement of a fiducial due, e.g., to patient movement, such as breathing or the like. In this context, a fiducial includes a structure that is internal or external to the patient, that can be identified in an image captured by the imaging system, and that can be used to determine the location of an irradiation target within the patient.

In the CT example, the image may include internal anatomical structures, such as organs, tumors, and bones, any of which may be an irradiation target (or fiducial, as described below). The imaging system captures one or more images of the patient, or a selected part of the patient, typically the part(s) of the patient where proton therapy is to be applied. In some implementations, the treatment couch may include one or more fiducials arranged thereon. Examples of fiducials may include, but are not limited to, metal or other material that shows-up on images, such as CT images. The fiducials may be arranged at areas around the patient, e.g., at and/or around parts of the patient where proton therapy is to be applied. In some implementations, at least three fiducials are arranged relative to the patient to enable use of a triangulation process to locate the irradiation target in both the CT image and the treatment space. In some implementations, CT images may be used to identify structural elements of a person's anatomy, such as teeth, bone, or the like, and to designate those structural elements as fiducials. In some implementations, fiducials may be a combination of any two or more of the foregoing, e.g., anatomical structures and/or structural elements secured to the treatment couch, to the patient, to a frame, or the like.

In the CT example, images are 3D so that, either alone or in combination, the images provide information about the location of the fiducials and the location of the irradiation target (e.g., the tumor) in 3D. This information is indicative of the relative positions of the fiducials and the irradiation target, and the angles and distances between individual fiducials and between individual fiducials and the radiation target. In some implementations, the position information is obtained by identifying the fiducials and the irradiation target in the 3D image(s), and by analyzing the image(s) to determine the locations of the fiducials and the size, shape, and location of the irradiation target based on the locations of the fiducials (and, in some cases, based on the size and/or shape of the fiducials). This information may be stored in computer memory and used during treatment in order to identify the location of the target in the treatment space (the "real world").

Following initial imaging using the CT system, the patient may be moved to the treatment position. The treatment couch may move automatically while the patient is on the couch, or the patient may move to a new treatment couch. The location to which the treatment is to be applied is determined, in part, based upon the 3D image(s) captured by the CT system (in this example).

Referring to FIG. 8, one or more treatment site (proton center) imaging systems 86, such as an X-ray system, are controlled to capture one or more images at the treatment position in the treatment space. This treatment site imaging system may be used alone, or in combination with, a computing system to detect locations of the fiducials, and thus the irradiation target, in the treatment space. The locations of the fiducials are detected relative to one or more reference points in a coordinate system that defines the treatment space. In other words, the treatment space (e.g., the proton center) may be defined within a 3D coordinate system, and the locations of the fiducials may be identified by coordinates in that 3D coordinate system.

For example, the images from the treatment site imaging system (e.g., X-ray images) may be analyzed to determine the locations of the fiducials in a 3D XYZ Cartesian coordinate system that defines the treatment space. One or more images of the fiducials taken by the imaging system may be analyzed to identify where, in the 3D coordinate system of the treatment space, the fiducials are located. The resulting coordinates of the fiducials in that coordinate system may be stored, e.g., in computer memory on a computer system (not shown).

The locations of the fiducials in the 3D coordinate system of the treatment space are aligned to the locations of the fiducials in the 3D CT image(s). This may be done automatically by a computer system using a virtual simulation (e.g., rendering) of the treatment space. For example, the actual locations of the fiducials may be identified in the simulation, and the fiducials from the 3D CT image, along with other structures from the CT image, may be placed at corresponding points in the simulation. By placing the fiducials and other structures from the CT image in the 3D coordinate system of the treatment space, it is possible to identify the location of the irradiation target in that same space.

More specifically, the locations of the fiducials in the treatment space (e.g., the 3D coordinate system of the treatment space) are known, and the fiducials and structures, including the irradiation target, from the 3D CT image are mapped into the 3D coordinate system in the simulation. As part of the mapping, the fiducials from the CT image are aligned to the locations of the fiducials in the 3D coordinate system of the treatment space. Furthermore, the location of the irradiation target relative to the fiducials is known from the 3D CT image. For example, the distances and angles of the irradiation target relative to each fiducial are known. Given this information, the location and orientation of the irradiation target in the 3D coordinate system of the treatment space can be determined. This information is used to direct the particle beam to the irradiation target.

The foregoing process of locating (e.g., by X-ray) fiducials in the 3D coordinate system of the treatment space and correlating those fiducials to those found in the original CT image(s) may be automated and repeated each time the treatment couch supporting the patient is moved within the treatment space. In some implementations, after the images are taken for a position, because the process may be under computer control and patient positioning will be monitored to confirm that the patient has not moved, new images may not need to be captured at each new position to which the patient is moved. For example, accuracy of the treatment couch motion and immobilization of the patient may be relied upon to determine positions at new locations.

In this regard, the treatment couch may be moved automatically between treatment positions in order to treat different parts of the patient or to treat the patient from different angles, as in the case in IMPT. In some implementations, for each new position, a new image is captured, e.g., by an X-ray system, and is analyzed relative to the original CT image(s). The resulting position information identifies the location to be treated in the real world space, e.g., in the 3D coordinate system of the treatment space (e.g., the proton center). Knowing the location of the target, various components of the proton therapy system can be controlled to position the particle beam and/or the patient to provide appropriate treatment to appropriate target areas. In some example implementations, the various components can be controlled to perform treatment with respect to any part of the target, and are not constrained to treatment relative to a defined isocenter.

In some implementations, the treatment site imaging system(s) alone may be used to identify the location of the irradiation target, with or without fiducials, and to track movement of the target following repositioning or other event.

Referring to FIG. 8, a collision avoidance system 88 may be controlled to identify the locations of various components of the particle therapy system, the patient and other structures in the treatment space, and to feed-back that information to the control system. More specifically, as described, in some implementations, the system is automated in that the beam spreader, the particle accelerator and its components, and the treatment couch are controlled to move, automatically, to different positions between applications of the particle beam. This automatic movement is advantageous in that it eliminates the need for a human to reconfigure the system (e.g., the nozzle, accelerator, and/or couch positions) between applications of particle beam. However, automation will typically require coordination among the various moving parts of the system, which may be implemented by the control systems described here. For safety purposes, the collision avoidance system 88 tracks motion of system components, such as the treatment couch, the particle accelerator, the carriage containing the energy degrader and collimator, and so forth, and relays information about that motion to the control system. If the control system detects, based on that information, that there is a possibility of a collision between two components or between a component and the patient or other structures/objects in the treatment space, the control system intervenes and changes the trajectory of one or more of the components or halts the motion of one or more of the components.

In some implementations, the collision avoidance system 88 may be implemented using one or more sensors, a 3D imaging system, laser positioning, sonar, ultrasound, or any appropriate combination thereof. In some implementations, other types of device detection systems may be used instead of, or in addition to, those described herein to implement collision avoidance.

In addition to the foregoing, the nozzle—which in some implementations is located on the inner gantry—may be retracted away from the patient or other object in the treatment space in order to avoid collisions. In some examples, this aspect of nozzle operation may be controlled by the control system based on feedback information from the collision avoidance system.

Figure 14:
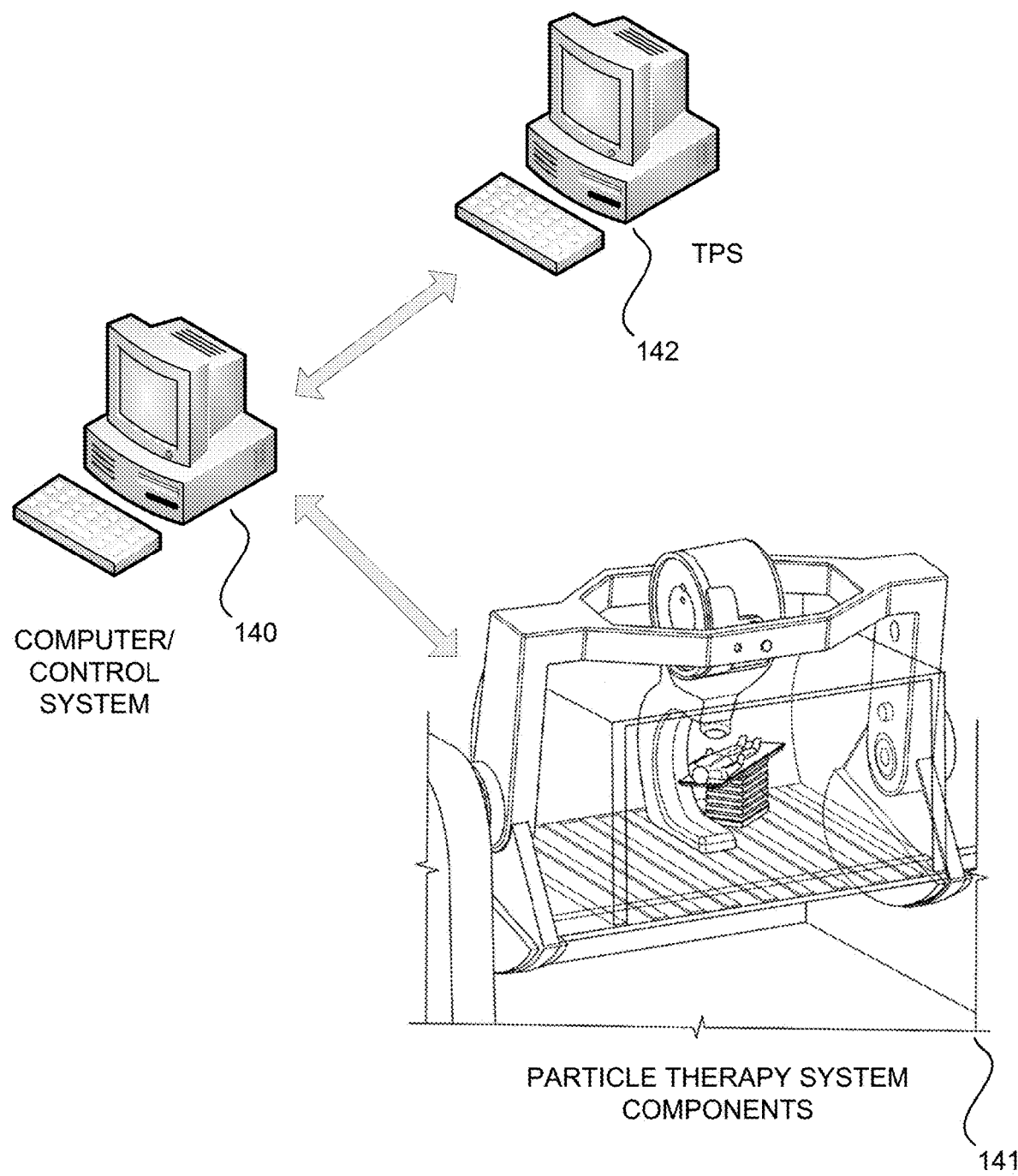
FIG. 14 is a system diagram depicting a control system, particle therapy system components, and a treatment planning system (TPS).

Referring to FIG. 14, control of the particle therapy system components 141 may include, but is not limited to, operation of and positioning and repositioning of the spreader—e.g., the one or more scanning magnets or scattering foils, the outer and inner gantries, the treatment couch, the nozzle, the beam shaping elements—e.g., the energy degrader and collimator, the carriage on which the beam shaping elements are mounted, the imaging systems (including, but not limited to, systems for beam targeting), the collision avoidance system, and the synchrocyclotron (both translation positioning and orientation positioning). Such control may implemented by a control system 140. Control system 140 may include one or more computer systems as described herein and/or other control electronics. For example, control of the particle therapy system and its various components may be implemented using hardware or a combination of hardware and software. For example, a system like the ones described herein may include various controllers and/or processing devices located at various points, e.g., a controller or other type of processing device may be embedded in each controllable device or system. A central computer may coordinate operation among the various controllers or other types of processing devices. The central computer, controllers, and/or processing devices may execute various software routines to effect control and coordination of testing, calibration, and particle therapy treatment.

To automate treatment in the manner described, an example TPS 142, which is in communication with the particle therapy system, defines a treatment session by sets of positions of a patient and positions of components of a particle (e.g., proton) output device. In an example, each set of positions may include, at least, a unique combination of a position of the treatment couch and a position of the output device, where the position of the output device is defined, at least in part, based on a position of the outer gantry (e.g., [couch position, beam position]). For each element in this set, a pattern of radiation is to be administered to at least a portion of an irradiation target. The motion of the patient is not limited to rotations, but also includes at least one translation, enabling the system to improve treatment of linear targets. The TPS may be implemented on one or more computer systems of the type described herein and/or other control electronics, and may be configured to communicate with control system 140 using any appropriate wired or wireless media. In some implementations, this allows a particle therapy system having a small beam field to treat large irradiation targets effectively and efficiently.

As explained above, the particle therapy system may have a relatively small beam field size, which is dictated, at least in part, by the distance between the particle/proton output device (for example, the spreader, the accelerator, or some other device capable of beam delivery) and the patient. In some implementations, the particle therapy system has a spreader-to-patient isocenter distance in a range of 1 m to 2 m (e.g., 1.5 m or less than 2 m) and a beam field area that is about 20 cm by 20 cm or less. In some implementations, the particle therapy system has a source-to-axis distance in a range of 1 m to 2 m (e.g., 1.5 m or less than 2 m) and a beam field area that is about 30 cm by 30 cm or less. Other values of the spreader-to-patient isocenter distance and beam field area also may be implemented.

In example implementations described herein, the spots size is dominated by a distance between the energy degrader, which dominates the beamline's contribution to beam divergence, and the patient. That is a distance that it may be advantageous to reduce, and why it may be beneficial to reduce the size of the components mounted to the nozzle. In some implementations, it is possible to perform downstream treatment of a defined isocenter.

Figure 15:
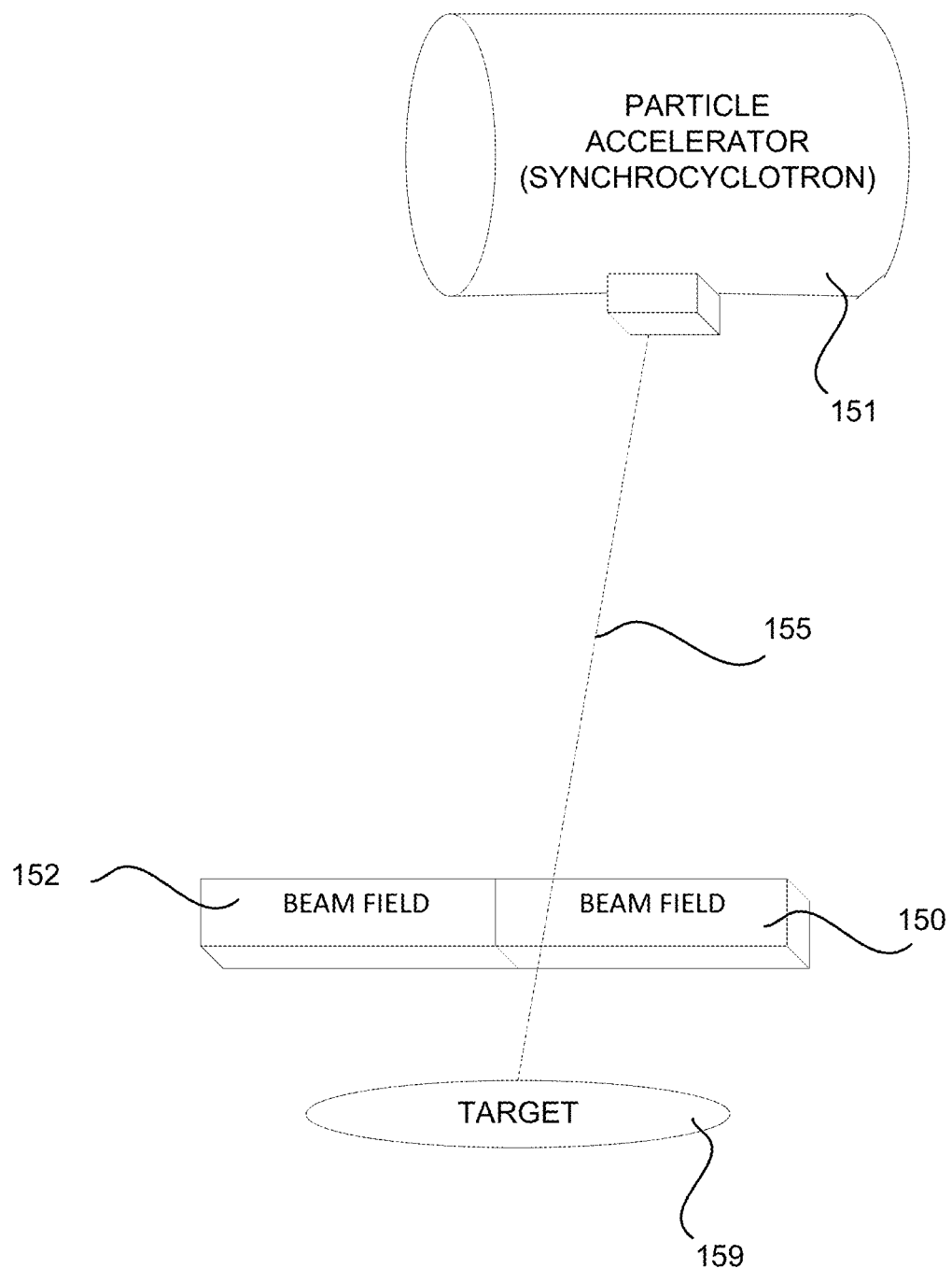
FIG. 15 is a block diagram depicting, conceptually, treatment across two different beam fields of a particle accelerator.

FIG. 15 shows an example of a beam field 150 relative to an irradiation target 159, which may be a tumor in the patient. Thus, in this example, the synchrocyclotron 151 does not have a beam field that is large enough to treat the entire irradiation target. Traditionally, particle beam 155 would be scanned across this first beam field 150 for a first treatment and then a radiation therapist would enter the treatment room and reposition the nozzle or other output device and/or the patient to scan the particle beam 155 across the second beam field 152 at a next isocenter. This process was repeated to treat the entire target, as described above.

The particle therapy system described herein, however, does not require a therapist to reposition the patient or the nozzle between treatments, at least in some cases (that is, the system does not prohibit therapist intervention, if necessary). For example, a computer system (e.g., control electronics) that controls the particle therapy system receives a treatment plan for the irradiation target. The treatment plan automates treatment using different beam fields (e.g., 150, 152). In some examples, the treatment plan also does not rely on isocenter locations for patient or beam positioning, although in other examples, isocenters may be used.

In some implementations, operation of the particle therapy system may be controlled with a button located outside of the proton center. For example, a single press of the button could begin treatment and, in some examples, the treatment may continue uninterrupted, and without requiring human intervention, across and using multiple beam fields until an entire treatment area has been treated. In some example implementations, the entire treatment of an irradiation target may be delivered in less than about five minutes which is enabled by the automated (e.g., without human intervention) beam field sequencing described herein. In some implementations, human intervention may be included in the treatment process. For example, a human may press the button (or buttons) located inside or outside of the proton center to begin application of radiation, and thus a new treatment, each time various components of the particle therapy system are automatically positioned following a preceding treatment.

In operation, the computer system interprets and/or executes instructions from the TPS to control one or more components of the particle therapy system in order to position the patient (and thus the target) and the particle beam at appropriate locations for treatment. Examples of components of the particle therapy system that may be controlled automatically to position the patient and the particle beam to implement automated treatment may include, but are not necessarily limited to one or more of the following: the spreader and/or the synchrocyclotron (including translational or pivotal movement), the outer gantry (for rotation of the synchrocyclotron and/or the spreader alone or in combination), the inner gantry (for positioning of the nozzle, including the beam shaping elements), the nozzle, the scanning magnet(s) or the scattering foil(s) (e.g., the beam spreader), the range modulator, the configurable collimator, the carriage to which the components of the nozzle are coupled, the treatment couch, the treatment site imaging system(s), and the collision avoidance system.

In addition, components of the synchrocyclotron may support treatment by controlling, e.g., by varying, the intensity of the particle beam during treatment. Variations in intensity may be achieved by controlling the number of particles per pulse of the particle beam. For example, the RF voltage sweep may be altered, or the operation of the ion source may be controlled, to select a desired intensity of the particle beam. Examples of processes that may be used by the synchrocyclotron described herein to control the intensity of the output particle beam are described in U.S. Patent Publication No. 2014/0094638 entitled "Controlling Intensity of a Particle Beam", the contents of which are incorporated herein by reference.

Using appropriate command and control protocols, in an example, the computer system 140 that directs operation of the particle therapy system controls operation, including positioning, of one or more of the spreader and/or the synchrocyclotron (including translational or pivotal movement), the outer gantry (for rotation of the synchrocyclotron and/or the spreader alone or in combination), the nozzle, the scanning magnet(s) or the scattering foil(s) (e.g., the beam spreader), the range modulator, the configurable collimator, and the carriage to which the components of the nozzle are coupled to position the particle beam at an appropriate location in the treatment space (e.g., the proton center) to administer radiation dosage to a target. Using appropriate command and control protocols, in an example, the computer system that directs operation of the particle therapy system controls operation of the treatment couch to position the patient, and thus the irradiation target, at an appropriate location in the treatment space to administer radiation dosage via the particle beam. Using appropriate command and control protocols, in an example, the computer system that directs operation of the particle therapy system controls operation of the synchrocyclotron to produce a particle beam having characteristics (e.g., intensity, energy, etc.) that are appropriate to administer required doses of radiation at locations defined in a treatment plan. Instructions in the TPS state where and when radiation is to be applied, and define the positions of the various system components needed to provide the appropriate radiation. Using appropriate command and control protocols, in an example, the computer system also directs operation of the site imaging system and the collision avoidance system to implement automated treatment.

Control over operation, including movement, of the spreader and/or the synchrocyclotron (including translational or pivotal movement), the outer gantry (for rotation of the synchrocyclotron and/or the spreader alone or in combination), the nozzle, the scanning magnet(s) or the scattering foil(s) (e.g., the beam spreader), the range modulator, the configurable collimator, the carriage to which the components of the nozzle are coupled, and the treatment couch enables positioning the patient and the beam with multiple degrees of freedom that exceed simple isocentric rotations of the particle accelerator and the treatment couch or that exceed simple isocentric rotations of the spreader and the treatment couch. For example, in some implementations, rotation of the gantry provides one degree of freedom; movement of, or produced by, the scanning magnet(s) provides two degrees of freedom; movement of, or produced by, the range modulator provides one degree of freedom; and movement of the treatment couch provides six degrees of freedom, resulting in ten degrees of freedom. In some implementations, as described herein, the spreader and/or the particle accelerator (and, thus, the particle beam) may be translatable (e.g., movable in a linear motion) in one, two, and/or three dimensions for additional degree(s) of freedom of movement. As explained herein, in some implementations, the spreader and/or the particle accelerator (and, thus, the particle beam) may be pivotable or be mounted to a gimbal (e.g., a pivoted support that allows the rotation of an object about a single axis), resulting in one or more additional degree(s) of freedom of movement. Control over movement of the carriage may provide an additional degree of freedom.

As noted, the computer system controls operation, including movement, of one or more of the spreader and/or the synchrocyclotron (including translational or pivotal movement), the outer gantry (for rotation of the synchrocyclotron and/or the spreader alone or in combination), the nozzle, the scanning magnet(s) or the scattering foil(s) (e.g., the beam spreader), the range modulator, the configurable collimator, the carriage to which the components of the nozzle are coupled, and the treatment couch to position the particle beam and/or the patient for treatment, and to automatically reposition the particle beam and/or the patient for additional, successive treatments. When that the patient is moved, the computer system may instruct, and control, the site imaging system(s) automatically to capture an image of the patient (and thus the irradiation target) at a new position, and to determine the location of the irradiation target at the new position. Movement may include pivoting, rotation and/or translation. For example, changes in patient orientation may be relevant to IMPT treatments. Determining the location of the irradiation target at the new position may be implemented as described above or using other appropriate methods. Thereafter, treatment may proceed. During movement, the collision avoidance system operates as described above to reduce the possibility of collision among components of the system. The collision avoidance system acts to reduce the possibility of collision among objects in the treatment space that are part of, and not part of, the system.

In some implementations, if it is determined, through patient monitoring, that the patient has not moved between treatment positions, then there may be no need to perform re-imaging or other processes to locate the irradiation target after each movement.

Movement of the patient couch may be in concert with treatment that occurs across beam fields. For example, in some implementations, the TPS may instruct automated treatment of a first beam field, followed by treatment of a second beam field, followed by treatment of a third beam field, and so forth. To generalize further, in some implementations, the moving parts of the system may be configured for each beam spot, making the beam delivery effectively fieldless in that the delivery is not constrained by field. Moreover, the particle therapy system may be controlled to move the particle beam back-and-forth between the same two beam fields multiple times, if necessary, independent of any system isocenters, if defined. In this example, as described elsewhere herein, movement of all components and control over imaging and sensors is automated, allowing the entire treatment process to be performed without a therapist manually repositioning the patient or the spreader and/or the particle accelerator.

Figure 16:
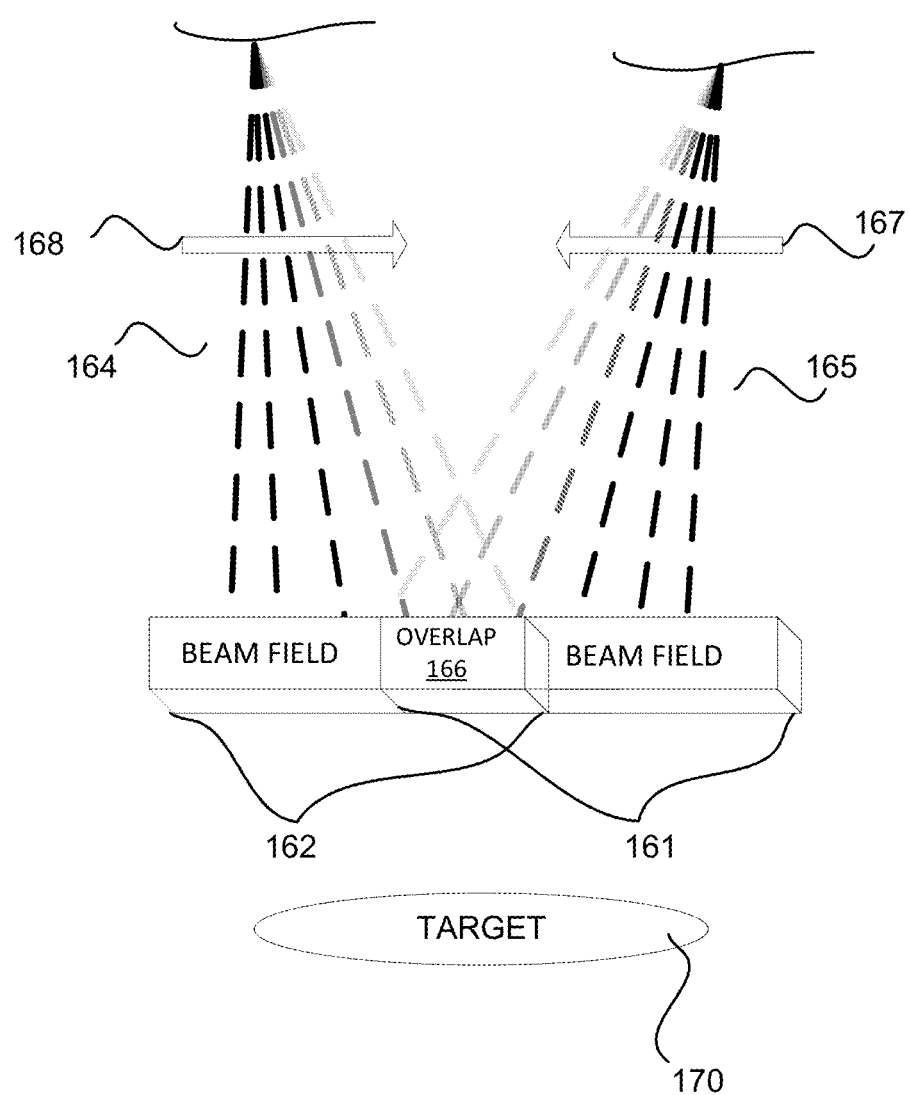
FIG. 16 is a block diagram depicting overlap of particle beams for two beam fields in an area of overlap of the two beam fields.

Referring to FIG. 16, different, adjacent beam fields 161, 162 may overlap at an area 166. The adjacent beam fields may be for treatment of target 170. This overlap area may be subjected to particle beams from different beam fields—in this example, particle beam 164 for beam field 162 and particle beam 165 for beam field 161. Because particle— and, in particular, proton—radiation is cumulative, if no corrective action is taken, beam overlap can cause too much radiation to be deposited in the areas of overlap. Likewise, if the areas of overlap are avoided, or the beams are not applied there correctly, then insufficient radiation for treatment may be applied (e.g., a gap). Accordingly, the example particle therapy system may be controlled to vary the intensity of the particle beam in areas of overlap, thereby allowing for beam overlap, while still ensuring that appropriate dosage is applied to areas of overlap between adjacent beam fields.

More specifically, in some implementations, the TPS may provide instructions in the treatment plan specifying the intensity of the beam at areas of overlap between adjacent beam fields. For example in an overlap area, particle beams from different beam fields may have lower intensities (e.g., a lesser concentration of protons) than particle beams in the beam fields, but outside the overlap area. The intensities of the beam may decrease further from the center of the beam field in a feathering effect. In this example, beam intensities are controlled so that the beams produce, in an overlap area, such as area 166, a uniform distribution of particles across the different beam fields. In some implementations, this uniform distribution is the same as the distribution in non-overlapping areas of one or both of the beam fields; however, because the distribution may vary even within a single beam field, this need not be the case. Specifically, the control system is configured to provide automated control of the particle accelerator to control intensities of the particle beams for the different beam fields so that cumulative intensities at areas of overlap between two or more particle beams reach a target beam intensity or are within a predefined range of the target intensity, and do not deviate from (e.g., exceed or fall below) the target intensity by more than a predefined amount.

In some examples, a certain amount of overlap, as shown in FIG. 16, is contemplated and accounted for by appropriate control over the particle beam, including variations in beam intensities at or near areas of overlap between adjacent beam fields. In the example of FIG. 16, intensity is represented by shading of the lines representing beams 164 and 165. As shown, the lines are darkest at non-overlapping areas, representing maximum (or appropriate) intensity for that beam field. The lines become progressively lighter as the lines move into the overlap area, representing a decrease in intensity of (e.g., concentration of particles in) the respective particle beams. For example, in the case of particle beam 165, as the particle beam is moved during scanning in the direction of arrow 167, the intensity of particle beam 165 decreases when it enters the overlap area 166 and continues to decrease to a minimum value at the end of the overlap area 166 furthest into beam field 162. Likewise, in the case of particle beam 164, as the particle beam is moved during scanning in the direction of arrow 168, the intensity of particle beam 164 decreases when it enters the overlap area 166 and continues to decrease to a minimum value at the end of the overlap area 166 furthest into beam field 161. In both cases, the intensities of the particle beams are controlled in the overlap areas such that the cumulative result from both beams in the overlap area is a uniform distribution of particles (or whatever other distribution is desired).

Thus, the overlap areas need not be avoided; appropriate doses of radiation are applied in the overlap areas; and the overlap areas between beam fields need not act as an impediment to automated operation of the treatment process. The configurable collimator described above may also be employed, where appropriate, to shape the beam at areas of overlap between adjacent beam fields or elsewhere. It is noted that the variations in intensity in the overlap areas are, effectively, a mitigation resulting from the risk of beam positioning errors/uncertainties. If automated positioning of the particle beam is precisely controlled at all locations of the irradiation target, dose distributions may not need to be controlled in the manner described with respect to FIG. 16.

As noted, the combination of movement of the treatment couch and/or the particle beam may produce a relative rotational movement, a relative pivotal movement, and/or a relative translational movement. Rotational movements may be used, e.g., in IMPT treatments, whereas translational movements may be used, e.g., to treat across beam fields. Rotational movements and translational movements, or combinations thereof, are not limited to these contexts, and may have applicability outside of IMPT and treatment across beam fields. In some implementations, the system may implement an effective translational movement of 5 cm or more, e.g., 5 cm to 50 cm or more, thereby enabling treatment of relatively long areas, such as a human spine, which could potentially span multiple beam fields.

The example particle therapy system may be controlled to implement any number of combined patient and beam positions that are appropriate for a given treatment plan. A combined patient and beam position may include any unique combination of a single position of the treatment couch (or patient) and a single position of the beam. By way of example, in a single treatment session, the example particle therapy system may be controlled to implement any appropriate number of combined patient and beam positions. Examples include, but are not limited to, two or more combined patient and beam positions, five or more combined patient and beam positions, ten or more combined patient and beam positions, 100 or more combined patient and beam positions, and 10,000 or more combined patient and beam positions. To reiterate, each combined patient and beam position is achieved through computer (e.g., automated) control over components of the particle therapy system (treatment couch, gantry, scanning components, etc.) and computer control over imaging system(s), such as the site imaging system(s) and the collision avoidance system. A TPS may provide appropriate instructions to effect control. In some implementations, the TPS may know beforehand the capabilities of the particle therapy system, and determine instructions for the treatment plan automatically based on a radiation dosage recommended by a medical professional and knowledge of the location, shape, and other relevant characteristics of the irradiation target (e.g., a tumor). Rather than limiting the number of beam fields, due to the various components described herein that enable beam positioning, in some examples, the particle therapy system described herein enables precise control over particle beam positioning, thereby effectively increasing the number of beam fields (e.g., to one for each position of the beam and patient) in order to increase the accuracy at which particle therapy is delivered.

The time for a treatment session will vary based on any number of factors including, but not limited to, the size of the target, the dosage to be applied, the number of combined patient and beam positions to be implemented, and so forth.

In some cases, an average treatment time may be less than 15 minutes or less than 45 minutes in some examples.

Operation of the example particle therapy systems described herein, and operation of all or some component thereof, can be controlled (as appropriate), at least in part, using one or more computer program products, e.g., one or more computer programs tangibly embodied in one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the operations of the example particle therapy systems described herein can be performed by one or more programmable processors executing one or more computer programs to perform the functions described herein. All or part of the operations can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Non-transitory machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Any "electrical connection" as used herein may imply a direct physical connection or a wired or wireless connection that includes intervening components but that nevertheless allows electrical signals to flow between connected components. Any "connection" involving electrical circuitry that allows signals to flow, unless stated otherwise, is an electrical connection and not necessarily a direct physical connection regardless of whether the word "electrical" is used to modify "connection".

Any two more of the foregoing implementations may be used in an appropriate combination with an appropriate particle accelerator (e.g., a synchrocyclotron). Likewise, individual features of any two more of the foregoing implementations may be used in an appropriate combination.

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

In some implementations, the synchrocyclotron used in the particle therapy system described herein may be a variable-energy synchrocyclotron. In some implementations, a variable-energy synchrocyclotron is configured to vary the energy of the output particle beam by varying the magnetic field in which the particle beam is accelerated. For example, the current may be set to any one of multiple values to produce a corresponding magnetic field. In an example implementation, one or more sets of superconducting coils receives variable electrical current to produce a variable magnetic field in the cavity. In some examples, one set of coils receives a fixed electrical current, while one or more other sets of coils receives a variable current so that the total current received by the coil sets varies. In some implementations, all sets of coils are superconducting. In some implementations, some sets of coils, such as the set for the fixed electrical current, are superconducting, while other sets of coils, such as the one or more sets for the variable current, are non-superconducting (e.g., copper) coils.

Generally, in a variable-energy synchrocyclotron, the magnitude of the magnetic field is scalable with the magnitude of the electrical current. Adjusting the total electric current of the coils in a predetermined range can generate a magnetic field that varies in a corresponding, predetermined range. In some examples, a continuous adjustment of the electrical current can lead to a continuous variation of the magnetic field and a continuous variation of the output beam energy. Alternatively, when the electrical current applied to the coils is adjusted in a non-continuous, step-wise manner, the magnetic field and the output beam energy also varies accordingly in a non-continuous (step-wise) manner. The scaling of the magnetic field to the current can allow the variation of the beam energy to be carried out relatively precisely, thus reducing the need for an energy degrader. An example of a variable-energy synchrocyclotron that may be used in the particle therapy system is described in U.S. Patent Publication No. 2014/0371511 entitled "Particle Accelerator That Produces Charged Particles Having Variable Energies", the contents of which are incorporated herein by reference. Implementations that employ a variable-energy synchrocyclotron In some implementations, a particle accelerator other than a synchrocyclotron may be used in the particle therapy system described herein. For example, a cyclotron, a synchrotron, a linear accelerator, or the like may be substituted for the synchrocyclotron described herein. Although a rotational gantry has been described (e.g., the outer gantry), the example particle therapy systems described herein are not limited to use with rotational gantries. Rather, a particle accelerator may be mounted, as appropriate, on any type of robotic or other controllable mechanism(s)—characterized herein also as types of gantries—to implement movement of the particle accelerator. For example, the particle accelerator and/or the spreader may be mounted on or more robotic arms to implement rotational, pivotal, and/or translational movement of the accelerator and/or the spreader relative to the patient. In some implementations, the particle accelerator and/or the spreader may be mounted on a track, and movement along the track may be computer-controlled. In this configuration, rotational and/or translational and/or pivotal movement of the accelerator and/or the spreader relative to the patient can also be achieved through appropriate computer control.

In some implementations, the particle accelerator itself may not move relative to the patient, as described herein. For example, in some implementations, the particle accelerator may be a stationary machine or at least not mounted for movement relative the patient. In examples like this, the particle accelerator may output its particle beam from the extraction channel to a transmission channel. The transmission channel may include magnets and the like for controlling magnetic fields contained therein in order to transport the particle beam to one or more remote locations, such as one or more treatment rooms. In each treatment room, the transmission channel may direct the beam to a beam spreader or other apparatus that is mounted for movement as described herein (e.g., to an outer gantry or other device). The beam spreader may thus be in place of the accelerator described elsewhere herein. However, in some examples, except for positioning of the accelerator, the spreader, and the transmission channel, the configuration and operation of this implementation of the particle accelerator system is the same as the configuration and operation of other implementations of the particle therapy system described elsewhere herein, as appropriate.

For example, using appropriate command and control protocols, in an example, the computer system 140 that directs operation of the particle therapy system controls operation, including positioning, of one or more of the gantry-mounted spreader (including translational, pivotal movement, and/or rotational movement), the beam shaping elements, the range modulator, the configurable collimator, the carriage to which the beam shaping elements are coupled, a nozzle, and the treatment couch to position the particle beam at an appropriate location in the treatment space to administer radiation dosage to a target. Using appropriate command and control protocols, in an example, the computer system that directs operation of the particle therapy system controls operation of the treatment couch to position the patient, and thus the irradiation target, at an appropriate location in the treatment space to administer radiation dosage via the particle beam. Using appropriate command and control protocols, in an example, the computer system that directs operation of the particle therapy system also controls operation of the synchrocyclotron to produce a particle beam having characteristics (e.g., intensity, energy, etc.) that are appropriate to administer required doses of radiation at locations defined in a treatment plan. Instructions in the TPS state where and when radiation is to be applied, and define the positions of the various system components needed to provide the appropriate radiation. Other possible operations of the particle therapy system are as described elsewhere herein.

Another example implementation of a particle therapy system in which the control systems described herein may be implemented is described in U.S. Pat. No. 7,728,311 entitled "Charged Particle Radiation Therapy", the contents of which are incorporated herein by reference. The content incorporated by reference includes, but is not limited to, the description of the synchrocyclotron and the gantry system holding the synchrocyclotron found in U.S. Pat. No. 7,728,311.

Other implementations not specifically described herein are also within the scope of the following claims.

What is claimed is:

1. A particle therapy system comprising:
a particle beam output device to direct output of a particle beam;
a treatment couch to support a patient containing an irradiation target, the treatment couch being configured for movement;
a movable device on which the particle beam output device is mounted for movement relative to the treatment couch, where different positions of the particle beam output device define beam fields for the particle beam including a first beam field and a second beam field, where each beam field comprises a plane that defines a maximum extent that the particle beam can move relative to the irradiation target; and
a control system to provide automated control of the movable device to position the particle beam output device for treatment of the irradiation target with the particle beam in the first beam field and, following the treatment of the irradiation target with the particle beam, to provide automated control of the movable device to reposition the particle beam output device for additional treatment of the irradiation target with the particle beam in the second beam field;
wherein the particle beam output device comprises a particle accelerator;
wherein the first beam field and the second beam field overlap at least partly in an overlap area; and
wherein the control system is configured to provide automated control of the particle accelerator to control intensities of the particle beam when the particle beam is applied in the first beam field and when the particle beam is applied in the second beam field so that cumulative intensities of the particle beam in the overlap area reach a target beam intensity.

2. The particle therapy system of claim 1, wherein, in the overlap area, the particle beam is applied from different angles.

3. The particle therapy system of claim 1, wherein the overlap area comprises an intersection of at least two planes.

4. A particle therapy system comprising:
a particle beam output device to direct output of a particle beam;
a treatment couch to support a patient containing an irradiation target, the treatment couch being configured for movement;
a movable device on which the particle beam output device is mounted for movement relative to the treatment couch, where different positions of the particle beam output device define beam fields for the particle beam including a first beam field and a second beam field, where each beam field comprises a plane that defines a maximum extent that the particle beam can move relative to the irradiation target; and
a control system to provide automated control of the movable device to position the particle beam output device for treatment of the irradiation target with the particle beam in the first beam field and, following the treatment of the irradiation target with the particle beam, to provide automated control of the movable device to reposition the particle beam output device for additional treatment of the irradiation target with the particle beam in the second beam field;
wherein the particle beam output device comprises a particle accelerator;
wherein the first beam field and the second beam field overlap at least partly in an overlap area; and
wherein the control system is configured to provide automated control of the particle accelerator to control intensities of the particle beam when the particle beam is applied in the first beam field and when the particle beam is applied in the second beam field so that cumulative intensities of the particle beam in the overlap area do not deviate from a target beam intensity by more than a defined amount.

5. The particle therapy system of claim 4, wherein, in the overlap area, the particle beam is applied from different angles.

6. A method comprising:
in a particle therapy system, supporting a patient containing an irradiation target on a treatment couch, the treatment couch being configured for movement;
mounting a particle beam output device on a movable device for movement relative to the treatment couch, the particle beam output device for directing output of a particle beam to treat the irradiation target, where different positions of the particle beam output device define beam fields for the particle beam including a first beam field and a second beam field, where each beam field comprises a plane that defines a maximum extent that the particle beam can move relative to the irradiation target; and
providing automated control of the movable device to position the particle beam output device for treatment of the irradiation target with the particle beam in the first beam field and, following the treatment of the irradiation target with the particle beam, providing automated control of the movable device to reposition the particle beam output device for additional treatment of the irradiation target with the particle beam in the second beam field;
wherein the particle beam output device comprises a particle accelerator;
wherein the first beam field and the second beam field overlap at least partly in an overlap area; and
wherein a control system provides automated control of the particle accelerator to control intensities of the particle beam when the particle beam is applied in the first beam field and when the particle beam is applied in the second beam field so that cumulative intensities of the particle beam in the overlap area reach a target beam intensity.

7. The method of claim 6, wherein, in the overlap area, the particle beam is applied from different angles.

8. The method of claim 6, wherein the overlap area comprises an intersection of at least two planes.

9. The method of claim 6, wherein the particle beam output device comprises at least part of a scanning system;
wherein the control system provides automated control of one or more components of the at least part of the scanning system to move the particle beam relative to the irradiation target.

10. The method of claim 9, wherein the one or more components comprise one or more scanning magnets.

11. The method of claim 9, wherein the scanning system comprises an energy degrader, the energy degrader comprising one or more structures that are movable into, and out of, a path of the particle beam.

12. A method comprising:
in a particle therapy system, supporting a patient containing an irradiation target on a treatment couch, the treatment couch being configured for movement;
mounting a particle beam output device on a movable device for movement relative to the treatment couch, the particle beam output device for directing output of a particle beam to treat the irradiation target, where different positions of the particle beam output device define beam fields for the particle beam including a first beam field and a second beam field, where each beam field comprises a plane that defines a maximum extent that the particle beam can move relative to the irradiation target; and
providing automated control of the movable device to position the particle beam output device for treatment of the irradiation target with the particle beam in the first beam field and, following the treatment of the irradiation target with the particle beam, providing automated control of the movable device to reposition the particle beam output device for additional treatment of the irradiation target with the particle beam in the second beam field;
wherein the particle beam output device comprises a particle accelerator;
wherein the first beam field and the second beam field overlap at least partly in an overlap area; and
wherein a control system provides automated control of the particle accelerator to control intensities of the particle beam when the particle beam is applied in the first beam field and when the particle beam is applied in the second beam field so that cumulative intensities of the particle beam in the overlap area do not deviate from a target beam intensity by more than a defined amount.

13. The method of claim 12, wherein, in the overlap area, the particle beam is applied from different angles.

14. A method comprising:
in a particle therapy system, supporting a patient containing an irradiation target on a treatment couch, the treatment couch being configured for movement;
mounting a particle beam output device on a movable device for movement relative to the treatment couch, the particle beam output device for directing output of a particle beam to treat the irradiation target, where different positions of the particle beam output device define beam fields for the particle beam including a first beam field and a second beam field, where each beam field comprises a plane that defines a maximum extent that the particle beam can move relative to the irradiation target; and
providing automated control of the movable device to position the particle beam output device for treatment of the irradiation target with the particle beam in the first beam field and, following the treatment of the irradiation target with the particle beam, providing automated control of the movable device to reposition the particle beam output device for additional treatment of the irradiation target with the particle beam in the second beam field;
wherein the particle beam output device comprises a particle accelerator; and
wherein the first beam field and the second beam field do not overlap.

15. A method comprising:
in a particle therapy system, supporting a patient containing an irradiation target on a treatment couch, the treatment couch being configured for movement;
mounting a particle beam output device on a movable device for movement relative to the treatment couch, the particle beam output device for directing output of a particle beam to treat the irradiation target, where different positions of the particle beam output device define beam fields for the particle beam including a first beam field and a second beam field, where each beam field comprises a plane that defines a maximum extent that the particle beam can move relative to the irradiation target; and providing automated control of the movable device to position the particle beam output device for treatment of the irradiation target with the particle beam in the first beam field and, following the treatment of the irradiation target with the particle beam, providing automated control of the movable device to reposition the particle beam output device for additional treatment of the irradiation target with the particle beam in the second beam field;

wherein the first beam field and the second beam field overlap at least partly in an overlap area; and wherein a control system provides automated control of a particle accelerator to control intensities of the particle beam when the particle beam is applied in the first beam field and when the particle beam is applied in the second beam field so that cumulative intensities of the particle beam in the overlap area reach a target beam intensity or so that cumulative intensities of the particle beam in the overlap area do not deviate from a target beam intensity by more than a defined amount.

16. The method of claim 15, wherein the particle beam is applied at lower intensities in the overlap area than outside the overlap area.

17. The method of claim 15, wherein the particle beam is a proton beam, and wherein the control system controls the particle beam output device to provide intensity-modulated proton therapy to the irradiation target.

18. The method of claim 15, wherein the particle beam output device comprises the particle accelerator, the particle accelerator comprising a synchrocyclotron; and wherein the synchrocyclotron is mounted on the movable device to move at least part-way around the treatment couch, the movable device comprising a gantry.

19. The method of claim 15, wherein the overlap area comprises an intersection of at least two planes.

20. The method of claim 15, further comprising implementing automated control of the treatment couch to perform operations comprising: moving the treatment couch to treat a first part of the irradiation target with the particle beam and, following treatment of the first part of the irradiation target with the particle beam, moving the treatment couch to treat a second part of the irradiation target with the particle beam.

21. The method of claim 15, wherein the control system controls the treatment couch to implement translational motion.

22. The method of claim 15, wherein the control system controls the treatment couch to implement rotational motion.

23. The method of claim 15, further comprising:

using an imaging system, capturing images of the irradiation target; and providing automated control of the imaging system to perform operations comprising: the imaging system capturing one or more first images of the patient after positioning the particle beam output device for treatment of the irradiation target with the particle beam in the first beam field and before the particle beam output device applies the particle beam to the irradiation target in the first beam field, and the imaging system capturing one or more second images of the patient after repositioning the particle beam output device for treatment of the irradiation target with the particle beam in the second beam field and before the particle beam output device applies the particle beam to the irradiation target in the second beam field.

24. The method of claim 23, wherein the control system uses the one or more first images to identify a first location of the irradiation target in a treatment space of the particle therapy system, and the control system uses the one or more second images to identify a second location of the irradiation target in the treatment space.

25. The method of claim 15, wherein the control system receives a treatment plan from a treatment planning system, and interprets the treatment plan to implement the automated control of at least the movable device, the treatment plan containing information identifying positions of the movable device during at least some operations in an uninterrupted sequence of operations.

26. The method of claim 15, wherein the control system provides automated control of at least one of the movable device or the treatment couch independent of an isocenter defined in the particle therapy system.

27. The method of claim 26, wherein automated control of the treatment couch is implemented absent human intervention.

28. The method of claim 15, wherein the automated control of at least the movable device is triggered by a single user action.

29. The method of claim 15, wherein the particle accelerator comprises a synchrocyclotron having a superconducting electromagnetic structure.

30. The method of claim 15, wherein the particle accelerator comprises a variable-energy synchrocyclotron having a superconducting electromagnetic structure.

31. The method of claim 15, wherein the particle beam output device comprises a beam spreader.

32. The method of claim 15, wherein the particle beam output device comprises one or more scanning magnets or one or more scattering foils.

33. A particle therapy system comprising:

a particle beam output device to direct output of a particle beam;

a treatment couch to support a patient containing an irradiation target, the treatment couch being configured for movement;

a movable device on which the particle beam output device is mounted for movement relative to the treatment couch, where different positions of the particle beam output device define beam fields for the particle beam including a first beam field and a second beam field, where each beam field comprises a plane that defines a maximum extent that the particle beam can move relative to the irradiation target; and a control system to provide automated control of the movable device to position the particle beam output device for treatment of the irradiation target with the particle beam in the first beam field and, following the treatment of the irradiation target with the particle beam, to provide automated control of the movable device to reposition the particle beam output device for additional treatment of the irradiation target with the particle beam in the second beam field;

wherein the particle beam output device comprises a particle accelerator; and wherein the first beam field and the second beam field do not overlap.

34. A particle therapy system comprising:

a particle beam output device to direct output of a particle beam;

a treatment couch to support a patient containing an irradiation target, the treatment couch being configured for movement;

a movable device on which the particle beam output device is mounted for movement relative to the treatment couch, where different positions of the particle beam output device define beam fields for the particle beam including a first beam field and a second beam field, where each beam field comprises a plane that defines a maximum extent that the particle beam can move relative to the irradiation target; and a control system to provide automated control of the movable device to position the particle beam output device for treatment of the irradiation target with the particle beam in the first beam field and, following the treatment of the irradiation target with the particle beam, to provide automated control of the movable device to reposition the particle beam output device for additional treatment of the irradiation target with the particle beam in the second beam field;

wherein the first beam field and the second beam field overlap at least partly in an overlap area; and wherein the control system is configured to provide automated control of a particle accelerator to control intensities of the particle beam when the particle beam is applied in the first beam field and when the particle beam is applied in the second beam field so that cumulative intensities of the particle beam in the overlap area reach a target beam intensity.

35. The particle therapy system of claim 34, wherein the particle beam is applied at lower intensities in the overlap area than outside the overlap area.

36. The particle therapy system of claim 34, wherein the particle beam output device comprises the particle accelerator, the particle accelerator comprising a synchrocyclotron; and wherein the synchrocyclotron is mounted on the movable device to move the synchrocyclotron at least part-way around the treatment couch, the movable device comprising a gantry.

37. The particle therapy system of claim 34, wherein, in the overlap area, the particle beam is applied from different angles.

38. The particle therapy system of claim 34, wherein the overlap area comprises an intersection of at least two planes.

39. A particle therapy system comprising:

a particle beam output device to direct output of a particle beam;

a treatment couch to support a patient containing an irradiation target, the treatment couch being configured for movement;

a movable device on which the particle beam output device is mounted for movement relative to the treatment couch, where different positions of the particle beam output device define beam fields for the particle beam including a first beam field and a second beam field, where each beam field comprises a plane that defines a maximum extent that the particle beam can move relative to the irradiation target; and a control system to provide automated control of the movable device to position the particle beam output device for treatment of the irradiation target with the particle beam in the first beam field and, following the treatment of the irradiation target with the particle beam, to provide automated control of the movable device to reposition the particle beam output device for additional treatment of the irradiation target with the particle beam in the second beam field;

wherein the first beam field and the second beam field overlap at least partly in an overlap area; and wherein the control system is configured to provide automated control of a particle accelerator to control intensities of the particle beam when the particle beam is applied in the first beam field and when the particle beam is applied in the second beam field so that cumulative intensities of the particle beam in the overlap area do not deviate from a target beam intensity by more than a defined amount.

40. The particle therapy system of claim 39, wherein, in the overlap area, the particle beam is applied from different angles.

41. The particle therapy system of claim 39, wherein the overlap area comprises an intersection of at least two planes.

42. The particle therapy system of claim 34 or 39, wherein the particle beam output device comprises at least part of a scanning system, the at least part of the scanning system comprising one or more components to move the particle beam relative to the irradiation target.

43. The particle therapy system of claim 42, wherein the one or more components comprise one or more scanning magnets.

44. The particle therapy system of claim 42, wherein the scanning system comprises an energy degrader, the energy degrader comprising one or more structures that are movable into, and out of, a path of the particle beam.

45. The particle therapy system of claim 34 or 39, wherein the control system is configured to provide automated control of the treatment couch, the automated control comprising: moving the treatment couch to treat a first part of the irradiation target with the particle beam and, following treatment of the first part of the irradiation target with the particle beam, moving the treatment couch to treat a second part of the irradiation target with the particle beam.

46. The particle therapy system of claim 34 or 39, wherein the control system is configured to control the treatment couch to implement translational motion.

47. The particle therapy system of claim 34 or 39, wherein the control system is configured to control the treatment couch to implement rotational motion.

48. The particle therapy system of claim 34 or 39, further comprising:

an imaging system to capture images of the irradiation target;

wherein the control system is configured to provide automated control of the imaging system to perform the following operations: the imaging system capturing one or more first images of the patient after positioning the particle beam output device for treatment of the irradiation target with the particle beam in the first beam field and before the particle beam output device applies the particle beam to the irradiation target in the first beam field, and the imaging system capturing one or more second images of the patient after repositioning the particle beam output device for treatment of the irradiation target with the particle beam in the second beam field and before the particle beam output device applies the particle beam to the irradiation target in the second beam field.

49. The particle therapy system of claim 48, wherein the control system is configured to use the one or more first images to identify a first location of the irradiation target in a treatment space of the particle therapy system, and the control system is configured to use the one or more second images to identify a second location of the irradiation target in the treatment space.

50. The particle therapy system of claim 34 or 39, wherein the control system is configured to receive a treatment plan from a treatment planning system, and to interpret the treatment plan to implement the automated control of at least the movable device, the treatment plan containing information identifying positions of the movable device.

51. The particle therapy system of claim 34 or 39, wherein the control system is configured to provide automated control of at least one of the movable device or the treatment couch independent of an isocenter defined in the particle therapy system.

52. The particle therapy system of claim 51, wherein automated control of the treatment couch is implemented absent human intervention.

53. The particle therapy system of claim 34 or 39, wherein the automated control of at least the movable device is triggered by a single user action.

54. The particle therapy system of claim 34 or 39, wherein the particle accelerator comprises a synchrocyclotron having a superconducting electromagnetic structure.

55. The particle therapy system of claim 34 or 39, wherein the particle accelerator comprises a variable-energy synchrocyclotron having a superconducting electromagnetic structure.

56. The particle therapy system of claim 34 or 39, wherein the particle beam output device comprises a beam spreader.

57. The particle therapy system of claim 34 or 39, wherein the particle beam output device comprises one or more scanning magnets or one or more scattering foils.

58. The particle therapy system of claim 34 or 39, wherein the particle beam is a proton beam, and wherein the control system is configured to control the particle beam output device to provide intensity-modulated proton therapy to the irradiation target.

59. The particle therapy system of claim 1, 4, 34, or 39, wherein the control system is configured to provide automated control of the particle accelerator to control intensities of the particle beam when the particle beam is applied in the first beam field and when the particle beam is applied in the second beam field so as to produce a same distribution of particles in the overlap area as in a non-overlapping area of the first beam field and the second beam field.

60. The method of claim 6, 12, 23, or 15, wherein the control system provides automated control of the particle accelerator to control intensities of the particle beam when the particle beam is applied in the first beam field and when the particle beam is applied in the second beam field so as to produce a same distribution of particles in the overlap area as in a non-overlapping area of the first beam field and the second beam field.

61. The particle therapy system of claim 1, 4, 34, or 39, wherein the particle beam output device comprises a nozzle.

62. The method of claim 6, 12, 23, or 15, wherein the particle beam output device comprises a nozzle.

\* \* \* \* \*